(12) United States Patent
Garcia-Echeverria et al.

(10) Patent No.: US 7,998,972 B2
(45) Date of Patent: Aug. 16, 2011

(54) 1H-IMIDAZO[4,5-C]QUINOLINE DERIVATIVES IN THE TREATMENT OF PROTEIN KINASE DEPENDENT DISEASES

(75) Inventors: Carlos Garcia-Echeverria, Basel (CH); Hans-Georg Capraro, Rheinfelden (CH); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 1714 days.

(21) Appl. No.: 10/515,126

(22) PCT Filed: May 20, 2003

(86) PCT No.: PCT/EP03/05291

§ 371 (c)(1),
(2), (4) Date: Jun. 3, 2005

(87) PCT Pub. No.: WO03/097641

PCT Pub. Date: Nov. 27, 2003

(65) Prior Publication Data

US 2005/0245562 A1     Nov. 3, 2005

(30) Foreign Application Priority Data

May 21, 2002 (GB) .................................. 0211649.9

(51) Int. Cl.
*A61K 31/4166* (2006.01)
*A61K 31/4188* (2006.01)
*C07D 471/04* (2006.01)

(52) U.S. Cl. .......................................... 514/293; 546/81
(58) Field of Classification Search ................... 546/81; 514/293

See application file for complete search history.

(56) References Cited

U.S. PATENT DOCUMENTS

| | | | |
|---|---|---|---|
| 4,689,338 A | 8/1987 | Gerster |
| 4,698,348 A | 10/1987 | Gerster |
| 5,525,612 A | 6/1996 | Gerster |
| 5,605,899 A | 2/1997 | Gerster |

FOREIGN PATENT DOCUMENTS

| EP | 145340 | 6/1985 |
|---|---|---|
| EP | 0145340 | 6/1985 |
| EP | 307078 | 3/1989 |
| EP | 0310950 | 4/1989 |
| EP | 386722 | 9/1990 |
| EP | 0389302 | 9/1990 |
| EP | 441036 | 12/1990 |
| EP | 1104764 | 6/2001 |
| EP | 1256582 | 11/2002 |
| JP | 11080156 | 9/1997 |
| WO | WO 9215582 | 9/1992 |
| WO | WO 99/09029 | 2/1999 |
| WO | WO 0009506 | 2/2000 |
| WO | WO 0055154 | 9/2000 |
| WO | WO 0076519 | 12/2000 |
| WO | WO 0146190 | 6/2001 |
| WO | WO 01/97795 | 12/2001 |
| WO | WO 0246188 | 6/2002 |

OTHER PUBLICATIONS

Brown, T.H. et al., Journal of Medicinal Chemistry, American Chemical Society, 33, pp. 527-533 (1990).*
U.S. Appl. No. 10/579,867, commonly assigned to Novartis.*
U.S. Appl. No. 11/913,788, commonly assigned to Novartis.*
Kato, et al. (Document No: 132: 180573) retrieved from Caplus on Jun. 7, 2010.*
Brown, et al. J. Med. Chem. 1990, 33, 527-533.*
Isomers [online], [retrieved on Mar. 11, 2007]. Retrieved from the Internet, URL; http ://chemed.chem.purdue.edu/genchem/topicreview/bp/ I organic/isomers.html>.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Megyeri, K. et al., Molecular and Cellular Biology, 15, No. 4, pp. 2207-2218 (Apr. 1, 1995).
Lee, J.C. et al., Nature, 372, pp. 739-746 (Dec. 22, 1994).
Brown, T.H. et al., Journal of medicinal Chemistry, American Chemical Society, 33, pp. 527-533 (1990).
R.L.A. Bottrel et al., Antimicrobial Agents and Chemotherapy, American Society for Microbiology, 43, No. 4., pp. 856-861 (Apr. 1999).
G.A. Bishop et al., The Journal of Immunology, 165, No. 10, pp. 5552-5557 (2000).

* cited by examiner

*Primary Examiner* — Shawquia Young
(74) *Attorney, Agent, or Firm* — Michael G. Smith; Steve Gilholm

(57) ABSTRACT

The invention relates to the use of imidazoquinolines and salts thereof in the treatment of protein kinase dependent diseases and for the manufacture of pharmaceutical preparations for the treatment of said diseases, imidazoquinolines for use in the treatment of protein kinase dependent diseases, a method of treatment against said diseases, comprising administering the imidazoloquinolines to a warm-blooded animal, especially a human, pharmaceutical preparations comprising an imidazoquinoline, especially for the treatment of a protein kinase dependent disease, novel imidazoquinolines, and a process for the preparation of the novel imidazoquinolines.

9 Claims, No Drawings

1H-IMIDAZO[4,5-C]QUINOLINE DERIVATIVES IN THE TREATMENT OF PROTEIN KINASE DEPENDENT DISEASES

SUMMARY OF THE INVENTION

The invention relates to the use of imidazoquinolines and salts thereof in the treatment of protein kinase dependent diseases and for the manufacture of pharmaceutical preparations for the treatment of said diseases, imidazoquinolines for use in the treatment of protein kinase dependent diseases, a method of treatment against said diseases, comprising administering the imidazoloquinolines to a warm-blooded animal, especially a human, pharmaceutical preparations comprising an imidazoquinoline, especially for the treatment of a protein kinase dependent disease, novel imidazoquinolines, and a process for the preparation of the novel imidazoquinolines.

BACKGROUND OF THE INVENTION

Recently, the concept of treating proliferative diseases by using drugs designed specifically against abnormally active protein kinases has been definitely proven in the treatment of CML (Chronic Myeloic Leukemia) where a first product has now been approved for successful treatment: Clinical studies showed that the drug (N-{5-[4-(4-methyl-piperazino-methyl)-benzoylamido]-2-methylphenyl}-4-(3-pyridyl)-2-pyrimidine-amine, especially in the form of the methane sulfonate (monomesylate) salt called STI571, which is sold e.g. under the tradename Gleevec®, has impressive activity against chronic phase CML. Typical for CML is a characteristic t(9;22) translocation that juxtaposes the 5' end of the bcr gene with the 3' end of the abl gene, resulting in a unique 210 kDa fusion protein $p210^{bcr/abl}$ with constitutive activity. The result is a $p210^{bcr/abl}$-induced transformation ultimately leading to CML. STI571 is a reversible inhibitor that occupies the ATP binding pocket of $p210^{bcr/abl}$ and stabilizes the kinase in an inactive conformation. This inhibitory action appears to be the basis for its action against CML.

Overexpression or constitutive expression (activity) of protein kinases appears to be a general principle for transformations that finally lead to proliferative growth of cells and thus cancer, psoriasis or other proliferative diseases.

Overexpression or constitutive activation of the hepatocyte growth factor receptor c-Met has been observed in multiple cases of human cancer (see Fujita O S, Sugano K: Expression of c-met proto-oncogene in primary colorectal cancer and liver metastases. Jpn. J. Clin. Oncol. 1997; 27:378-383; and Liu C, Tsao M-S: In vitro and in vivo expressions of transforming growth factor-α and tyrosine kinase receptors in human non-small-cell lung carcinomas. Am. J. Pathol. 1993; 142:1155-1162). The MET receptor is overexpressed in tumors of specific histotypes, including thyroid and pancreatic carcinomas, or is acttivated through autocrine mechanisms. Moreover, the MET gene is amplified in liver metastasis of colorectal carcinomas. Receptor activation of the MET proto-oncogene triggers a unique process of differentiation called "branching morphogenesis" that involves the promotion of cell growth, protection from apoptosis and control of cell dissociation and migration into extracellular matrices. Hence c-Met had been selected as a target for cancer therapy.

The c-met gene had been sub-cloned to result in a protein fragment comprising the cytoplasmic part of the entire protein (Chan A M-L, King H W S, Tempest P R, Deakin E A, Cooper C S, Brookes P. Primary structure of the met protein tyrosine kinase domain. Oncogene 1987; 12:229-233). This construct, after hooking to a GST tag, was cloned into baculovirus and expressed in Sf9 cells. The expressed protein consists of 646 amino acids, of which the C-terminal 422 amino acids contain the kinase domain and the C-terminus of the c-Met protein and the N-terminal 224 amino acids are derived from GST and the fusion of the two proteins. The protein was partially purified by affinity chromatography on GST agarose resulting in a >90% pure preparation (SDS-PAGE).

Various other protein kinases that are involved in signal transmission mediated by trophic factors can be involved in proliferative (e.g. tumor) growth, as representative examples for protein tyrosine kinases, abl kinase, especially v-abl or c-abl kinase, kinases from the family of the src kinases, especially c-src kinase, lck, fyn; epidermal growth factor (EGF) receptor kinase or other kinases of the EGF family, for example c-erbB2 kinase (HER-2), c-erbB3 kinase, c-erbB4 kinase; members of the family of the platelet-derived growth factor (PDGF) receptor tyrosine protein kinases, for example PDGF-receptor kinase, CSF-1 receptor kinase, Kit-receptor kinase, vascular endothelial growth factor (VEGF) receptor kinase (e.g. KDR and Flt-1) and fibroblast growth factor (FGF) receptor kinase; the Insulin-like growth factor I receptor (IGF-IR) kinase, and/or serine/threonine kinases, for example protein kinase C (PK-C), PK-B, EK-B or cyclin-dependent kinases, such as CDK1, may be mentioned, all of which play a part in growth regulation and transformation in mammalian cells, including human cells.

What is desirable from the point of view of possible treatments of proliferative diseases is to have a plethora of compound classes each tailored to specific protein kinases or protein kinase classes, thus allowing to come to specific treatments. Therefore, a strong need exists to find new classes of compounds allowing for such specific inhibitory effects.

GENERAL DESCRIPTION OF THE INVENTION

The class of imidazoquinoline compounds described herein, especially novel compounds falling under this class, has surprisingly been found to have pharmaceutically advantageous properties, inter alia allowing for the inhibition of specific types or classes or groups of protein kinases, especially c-Met, CDK1, KDR, c-abl ("Abl") or PKB/Akt, or any combinations of two or more of these.

In addition to this established activity, the imidazoquinolines have the advantage that their backbone in addition allows for a plethora of substitution patterns that offer a broad possibility to achieve a fine tuning for specific interaction with the ATP binding site of the kinases, thus opening a new perspective and providing kinase inhibitors of various degrees of specificity.

DETAILED DESCRIPTION OF THE INVENTION

The invention in particular relates to the use of imidazoloquinolines, especially compounds of the formula I

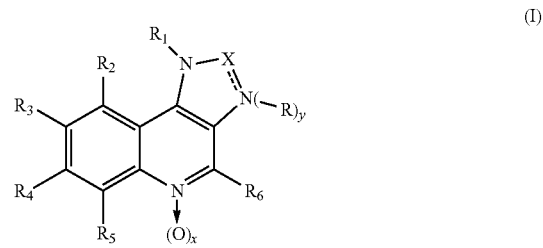

wherein
each of x and y is, independently of the other, 0 or 1,
$R_1$ is an organic moiety that can be bound to nitrogen,
X is C=O or C=S with the proviso that then the dashed line bonding X to N is absent, so that X is bound to the adjacent N via a single bond and with the proviso that then y is 1 and R is hydrogen or an organic moiety that can be bound to nitrogen;

or X is ($CR_7$) wherein $R_7$ is hydrogen or an organic or inorganic moiety with the proviso that then the dashed line bonding X to N is a bond, so that X is bound to the adjacent N via a double bond, and with the proviso that then y is zero or y is 1 and then —R is →O;

and each of $R_2$, $R_3$, R, $R_5$ and $R_6$, independently of the others, is an organic moiety or hydrogen or an inorganic moiety;

or (especially pharmaceutically acceptable) salts thereof, in the treatment of protein kinase dependent diseases or for the manufacture of pharmaceutical preparations for the treatment of protein kinase dependent diseases, the imidazoquinoline compounds of the formula I for use in the treatment of protein kinase dependent diseases, a method of treatment against said diseases, comprising administering imidazoloquinolines compounds of the formula I to a warm-blooded animal, especially a human, pharmaceutical preparations comprising an imidazoline compound of the formula I, especially for the treatment of a protein kinase dependent disease, novel imidazoquinoline compounds of the formula I, a process for the manufacture of the novel imidazoquinoline compounds of the formula I, and novel starting materials and intermediates for their manufacture.

The general terms used hereinbefore and hereinafter preferably have within the context of this disclosure the following meanings, unless otherwise indicated:

The prefix "lower" denotes a radical having 1 up to and including a maximum of 7, especially 1 up to and including a maximum of 4 carbon atoms, the radicals in question being either linear or branched with single or multiple branching. Lower alkyl, for example, is methyl, ethyl, n-propyl, sec-propyl, n-butyl, isobutyl, sec-butyl, tert-butyl, n-pentyl, n-hexyl or n-heptyl.

Where the plural form is used for compounds, salts, pharmaceutical preparations, diseases and the like, this is intended to mean also a single compound, salt, or the like.

In view of the close relationship between the novel compounds in free form and in the form of their salts, including those salts that can be used as intermediates, for example in the purification or identification of the novel compounds, tautomers or tautomeric mixtures and their salts, any reference hereinbefore and hereinafter to compounds of the formula I is to be understood as referring also to the corresponding tautomers of compounds of the formula I or their N-oxides, tautomeric mixtures of compounds of the formula I or their N-oxides, or salts of any of these, as appropriate and expedient and if not mentioned otherwise. Tautomers can, e.g., be present in cases where amino or hydroxy, each with a least one bound hydrogen, are bound to carbon atoms that are bound to adjacent atoms by double bonds (e.g. keto-enol or inine-enamine tautomerism).

Any asymmetric carbon atom may be present in the (R)-, (S)- or (R,S)-configuration, preferably in the (R)- or (S)-configuration. Substituents at a double bond or a ring may be present in cis-(=Z-) or trans (=E-) form. The compounds may thus be present as mixtures of isomers or preferably as pure isomers, preferably as enantiomer-pure diastereomers or pure enantiomers.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

An organic moiety that can be bound to nitrogen is preferably unsubstituted or substituted alkyl, unsubstituted or substituted alkenyl, unsubstituted or substituted alkinyl, unsubstituted or substituted aryl, unsubstituted or substituted heterocyclyl, unsubstituted or substituted cycloalkyl or unsubstituted or substituted cycloalkenyl.

An organic moiety is preferably unsubstituted or substituted alkyl, unsubstituted or substituted alkenyl, unsubstituted or substituted alkinyl, unsubstituted or substituted aryl, unsubstituted or substituted heterocyclyl, unsubstituted or substituted cycloalkyl or unsubstituted or substituted cycloalkenyl, unsubstituted or substituted arylcarbonylamino, amino substituted by one or two moieties selected from the group consisting of lower alkyl, substituted lower alkyl moieties, aryl, cycloalkyl and mercapto-lower alkyl, alkyloxy or cyano.

"Substituted", wherever used for a moiety, means that one or more hydrogen atoms in the respective moiety, especially up to 5, more especially up to three, of the hydrogen atoms are replaced independently of each other by the corresponding number of substituents which preferably are independently selected from the group consisting of lower alkyl, for example methyl, ethyl or propyl, halo-lower alkyl, for example trifluoromethyl, $C_6$-$C_{16}$-aryl, especially phenyl or naphthyl (where $C_6$-$C_{16}$-aryl, especially phenyl or napthyl, is unsubstituted or substituted by one or more, especially up to three moieties selected from halogen, carboxy, lower alkoxycarbonyl, hydroxy, lower alkoxy (especially methoxy), phenyl-lower alkoxy, lower alkanoyloxy, lower alkanoyl, amino, N-lower alkylamino, N,N-di-lower alkylamino, N-phenyl-lower alkylamino, N,N-bis(phenyl-lower alkyl)-amino, lower alkanoylamino, halo, halo-lower alkyl, e.g. trifluoromethyl, sulfo, cyano, cyano-lower alkyl and nitro), $C_3$-$C_{10}$-cycloalkyl, especially cyclopropyl or cyclohexyl, hydroxy-$C_3$-$C_8$-cycloalkyl, such as hydroxy-cyclohexyl, heteroaryl with 5 or 6 ring atoms and 1 to 3 ring heteroatoms selected from O, N and S, especially furyl, hydroxy, lower alkoxy, for example methoxy, phenyl-lower alkoxy, lower alkanoyloxy, hydroxy-lower alkyl, such as hydroxymethyl or 2-hydroxyethyl, amino, N-lower alkylamino, N,N-di-lower alkylamino, N-phenyl-lower alkylamino, N,N-bis(phenyl-lower alkyl)-amino, lower alkanoylamino, benzoylamino, carbamoyl-lower alkoxy, N-lower alkylcarbamoyl-lower alkoxy or N,N-di-lower alkylcarbamoyl-lower alkoxy, amidino, N-hydroxy-amidino, guanidino, amino-lower alkyl, such as aminomethyl or 2-aminoethyl, amidino-lower alkyl, such as 2-amidinoethyl, N-hydroxyamidino-lower alkyl, such as N-hydroxy-amidino-methyl or -2-ethyl, halogen, for example fluoro, chloro, bromo or iodo, carboxy, lower alkoxycarbonyl, phenyl-, naphthyl- or fluorenyl-lower alkoxycarbonyl, such as benzyloxycarbonyl, lower alkanoyl, sulfo, lower alkanesulfonyl, for example methanesulfonyl ($CH_3$—$S(O)_2$—), phosphono (—$P(=O)(OH)_2$), hydroxy-lower alkoxy phosphoryl or di-lower alkoxyphosphoryl, carbamoyl, mono- or di-lower alkylcarbamoyl, sulfamoyl, mono- or di-lower alkylaminosulfonyl, nitro cyano-lower alkyl, such as cyanomethyl, and cyano. It goes without saying that substitutents are only at positions where they are chemically possible, the person skilled in the art being able to decide (either experimentally or theoretically) without inappropriate effort which substitutions are possible and which are not. For example, amino or hydroxy groups with free hydrogen may be unstable if bound to carbon atoms with unsaturated (e.g. olefinic) bonds.

Halo or Halogen is preferably fluoro, chloro, bromo or iodo, most preferably fluoro, chloro or bromo.

Alkyl preferably has up to 20, more preferably up to 12 carbon atoms and is linear or branched one or more times;

preferred is lower alkyl, especially $C_1$-$C_4$-Alkyl. Alkyl is unsubstituted or substituted, preferably by one or more substituents independently selected from those mentioned above under "Substituted". Unsubstituted alkyl, preferably lower alkyl, or hydroxyalkyl, especially hydroxy-lower alky, e.g. 2-hydroxyethyl, is especially preferred as an organic moiety that can be bound to nitrogen.

Among the moieties corresponding to substituted alkyl, unsubstituted or substituted aryl-lower alkyl (especially preferred), heterocyclyl-lower alkyl, or cycloalkyl-lower alkyl are also preferred.

Aryl-lower alkyl is preferably lower alkyl that is substituted (preferably terminally or in 1-position) by unsubstituted or substituted aryl as defined below, especially phenyl-lower alkyl, such as benzyl or phenylethyl, especially 1-phenyl-ethyl.

Heterocyclyl-lower alkyl is preferably lower alkyl that is substituted (preferably terminally) by unsubstituted or substituted heterocyclyl as defined below.

Cycloalkyl-lower alkyl is preferably lower alkyl that is substituted (preferably terminally) by unsubstituted or substituted cycloalkyl as defined below.

Alkenyl is preferably a moiety with one or more double bonds and preferably has 2 to 20, more preferably up to 12, carbon atoms; it is linear or branched one or more times (as far as possible in view of the number of carbon atoms). Preferred is $C_2$-$C_7$-alkenyl, especially $C_3$-$C_4$-alkenyl, such as allyl or crotyl. Alkenyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a double bond, and also other substituents that are not sufficiently stable are preferably excluded. Unsubstituted alkenyl, in particular $C_2$-$C_7$-alkenyl, is preferred.

Alkinyl is preferably a moiety with one or more triple bonds and preferably has 2 to 20, more preferably up to 12, carbon atoms; it is linear of branched one or more times (as far as possible in view of the number of carbon atoms). Preferred is $C_2$-$C_7$alkinyl, especially $C_3$-$C_4$-alkinyl, such as ethinyl or propin-2-yl. Alkinyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a triple bond, and also other substituents that are not sufficiently stable are preferably excluded. Unsubstituted alkinyl, in particular $C_2$-$C_7$-alkinyl, is preferred.

Aryl preferably has a ring system of not more than 20 carbon atoms, especially not more than 16 carbon atoms, is preferably mono-, bi- or tric-cyclic, and is unsubstituted or substituted preferably as defined above under "Substituted". For example, aryl is selected from phenyl, naphthyl, indenyl, azulenyl and anthryl, and is preferably in each case unsubstituted or halo (especially fluoro, chloro, bromo or iodo), halo-lower alkyl (especially trifluoromethyl), hydroxy, amino, lower alkoxy (especially methoxy), hydroxy-lower alkyl (especially hydroxymethyl or 2-hydroxyethyl), amino-lower alkyl (especially aminomethyl or 2-aminoethyl), lower alkyl (especially methyl or ethyl), cyano, cyano-lower alkyl (especially 2-cyanoethyl), amidino, N-hydroxyamidino, amidino-lower alkyl (especially 2-amidino-ethyl) or N-hydroxyamidino-lower alkyl (especially 2-(N-hydroxyamidino)-ethyl) substituted phenyl or (especially 1- or 2-) naphthyl. Unsubstituted or substituted aryl, preferably phenyl, hydroxyphenyl, such as 4-hydroxyphenyl, or methoxyphenyl, such as 2-, 3- or 4-methoxyphenyl; or lower alkyl, especially methyl or ethyl; is especially preferred as organic moiety that can be bound to nitrogen or as organic moiety $R_2$ to $R_7$.

In arylcarbonylamino, aryl is preferably aryl as defined in the last paragraph, especially benzoylamino.

Heterocyclyl is preferably a heterocyclic radical that is unsaturated, saturated or partially saturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted"; especially being a heteroaryl radical selected from the group consisting of oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, O-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro. Unsubstituted heterocyclyl is preferred.

Cycloalkyl is preferably $C_3$-$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1 to 3, substitutents independently selected from the group consisting of the substituents defined above under "Substituted".

Cycloalkenyl is preferably $C_5$-$C_{10}$-cycloalkenyl, especially cyclopentenyl, cyclohexenyl or cycloheptenyl, cycloalkenyl being unsubstituted or substituted by one or more, especially 1 to 3, substitutents independently selected from the group consisting of the substituents defined above under "Substituted".

An inorganic moiety $R_2$ to $R_7$ is preferably halogen, especially fluoro, chloro, bromo or iodo, hydroxy, amino, or nitro.

An organic moiety $R_2$ to $R_7$ is selected from the organic moieties mentioned above for organic moieties that can be bound to nitrogen (for $R_1$) or is alternatively selected from the group consisting of unsubstituted or substituted alkoxy, especially lower alkoxy or phenyl-lower alkoxy, such as methoxy, or lower alkanoyloxy, such as acetoxy, amino substituted by one or two moieties selected from the group consisting of lower alkyl, such as methyl or n-butyl, hydroxy-lower alkyl, such as 2-hydroxyethyl, mercapto-lower alkyl, such as 2-mercaptoethyl, unsubstituted or substituted aryl as defined above, especially phenyl, cycloalkyl as defined above, especially $C_3$-$C_6$-cycloalkyl, lower alkanoyl (preferably as single amino substituent or in combination with another of the non-acyl moiety just mentioned) and benzoyl or phenyl-lower alkanoyl (preferably as single amino substituent or in combination with another of the non-acyl moiety just mentioned), cyano, cyano-lower alkyl, such as cyanomethyl, amidino, N-hydroxyamidino, amidino-lower alkyl, such as -methyl, or N-hydroxyamidino-lower alkyl, such as -methyl.

Preferably, only up to 2, more preferably up to one of $R_2$, $R_3$, $R_4$, $R_5$, $R_6$, and $R_7$ are/is other than hydrogen (that is, an inorganic or organic moiety).

A very preferred group of compounds of formula I are those wherein $R_3$ is one of the organic moieties other than hydrogen, especially those mentioned as being preferred above.

Salts are preferably the pharmaceutically acceptable salts of compounds of formula I if they are carrying salt-forming groups.

Salt-forming groups in a compound of formula I are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or polyacid addition salts may be formed.

Compounds of formula I having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds of formula I having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Owing to the close relationship between the novel compounds in free form and in the form of their salts, including those salts that can be used as intermediates, for example in the purification of the novel compounds or for the identification thereof, any reference hereinbefore and hereinafter to the free compounds shall be understood as including the corresponding salts, where appropriate and expedient.

The compounds of formula I have valuable pharmacological properties and are useful in the treatment of protein kinase dependent diseases, for example, as drugs to treat proliferative diseases.

Compounds of the formula I, for example, are able to inhibit c-Met kinase as mentioned already in the introduction. Using the sequence disclosed by Chan et al. (see Chan, A M-L, King H W S, Tempest P R, Deakin E A, Cooper C S, Brookes P. Primary structure of the met protein tyrosine kinase domain. *Oncogene* 1987; 12:229-233), a construct with this sequence, after hooking to a GST tag, was cloned into baculovirus and expressed in Sf9 cells. After partial purification by affinity chromatography on GST agarose resulting in a >90% pure preparation (SDS-PAGE), the kinase activity of this construct is used for inhibition assays using the compounds of formula I. The quality of the purified kinase preparations is highly reproducible: 9 batches of c-Met gives an average specific activity of 32.3±5.7 nmol/mg·min.

For inhibition studies, the following experimental protocol is used:

Solutions, Materials:

| | |
|---|---|
| 3 × kinase buffer | 60 mM Tris · HCl pH 7.6, 30 µM $Na_3VO_4$, 3 mM DTT |
| 3 × substrate buffer | 10 mM $MnCl_2$, 30 mM $MgCl_2$ |
| $H_3PO_4$ | 0.5% in $H_2O$ |
| ATP unlabelled | 0.3 mM in $H_2O$ pH 7, stored in aliquots at −70° C. |
| ATP (γ-$^{33}$P-labelled) | Amersham AH9968, 10 mCi/ml, 3 Ci/µMol, 0.1 µCi/well |
| Inhibitors | 1 mM in DMSO (= stock solution), dilute 1:33 with $H_2O$, further dilutions with 3% DMSO/$H_2O$ |
| Trapping membranes | Immobilon$^P$ (Millipore), cut into size of 96-well plates |
| Filtration manifold | Convertible filtration manifold (Gibco) connected to house vacuum (ca 800 mbar) |
| Microtiter plates | 96-well Microtec 96 K-V (PE-LD) |
| Scintillation counter | Canberra-Packard TopCount |
| Enzyme | c-Met cytoplasmic domain (amino acids 969 to C-terminus). The purified protein has an apparent molecular weight of 80,000. The protein band is detectable on Western blots with anti-phosphotyrosine (4G10, Tom Roberts, DFCI, Boston, MA) and with anti-Met antibodies (Santa Cruz sc-161 rabbit polyclonal). The purified enzyme protein is stored in aliquots at approximately 1 mg protein/ml at −70° C. (25 mM Tris · HCl pH 8, 1 mM EDTA, 1 mM DTT, 10% glycerol, 1 mM PMSF, 10 µg/ml leupeptin, 10 µg/ml pepstatin, 1 µg/ml aprotinin). Immediately prior to use, c-Met is diluted with 3 × kinase buffer to 0.3-10 ng/µl. |
| Substrate | poly(EY), 10 mg/ml stored in aliquots at −70° C. |
| Assay mix | 3 × conc. (3 µg/ml poly(EY), 3 µM ATP, 0.1 µCi/10 µl mix of $^{33}$P-ATP in 3 × substrate buffer) |

Kinase Assay:

In vitro protein kinase assays are performed in 96-well plates. The amount of enzyme used in kinase assays and the incubation time for the kinase reaction are adjusted so that maximally 25% (in routine experiments <10%) of the substrate ATP are consumed.

Test compounds of the formula I are first dissolved in DMSO at a concentration of 1-10 mM (stock solution) and then further diluted with water/3% DMSO as required so that the final DMSO concentration in the assay is 1%.

The assay components are mixed in the following order:
10 µl 3×compound (in 3% DMSO)
10 µl 3×assay mix (MgCl$_2$/MnCl$_2$/ATP/$^{33}$P-ATP/poly (EY))
10 µl 3×enzyme dilution Assays are incubated for 15 min (in special cases up to 60 min) at ambient temperature, reactions terminated by addition of 10 µl 0.25 M EDTA pH 7, then 20 µl transferred to a Millipore Immobilon$^P$ membrane (previously soaked for 5 min with methanol, rinsed with water, then soaked for 5 min with 0.5% H$_3$PO$_4$ and mounted on vacuum manifold) with disconnected vacuum source. After spotting all samples, vacuum is connected and each well rinsed with 200 µl 0.5% H$_3$PO$_4$. Membranes are removed and washed 4× on shaker with 0.5% H$_3$PO$_4$, once with methanol. Membranes are counted after drying at ambient temperature, mounting in Packard TopCount 96-well frame, and addition of 10 µl/well of the scintillator Microscint™ (Packard).

IC$_{50}$ Calculations

| input | 3 × 4 µl stopped assay on Immobilon membrane, not washed |
|---|---|
| background (3 wells) | assay with H$_2$O instead of enzyme. |
| positive control (4 wells) | 3% DMSO instead of compound |
| bath control (1 well) | no reaction mix |

IC$_{50}$ values are calculated by logarithmic regression analysis of the percentage inhibition of each compound at 4 concentrations (usually 3- or 10-fold dilution series starting at 10 µM). In each experiment, the actual inhibition by reference compound is used for normalization of IC$_{50}$ values to the basis of an average value of the reference inhibitor:

Normalized IC$_{50}$=measured IC$_{50}$·average ref. IC$_{50}$/measured ref. IC$_{50}$ Example:
Reference inhibitor in experiment 0.4 µM, average 0.3 µM
Test compound in experiment 1.0 µM, normalization:

1.0·0.3/0.4=0.75 µM

For example, staurosporine or a synthetic staurosporine derivative are used as reference compounds.

Using this protocol, the compounds of the formula I are found to show IC$_{50}$ values for c-Met inhibition in the range from 0.001 to 20 µM, preferably in the range from 0.01 to 2 µM.

In addition, compounds of the formula I also show activity in the inhibition of CDK1 in detail, the inhibition of the enzyme p34$^{cdc2}$/cyclin B$^{cdc13}$ kinase can be demonstrated by the following experiment:

Starfish oocytes are induced into the M phase with 10 µM 1-methyl-adenine, frozen in liquid nitrogen and stored at −80° C. The ooctyes are homogenized and centrifuged, as described in D. Arlon et al., Cell 55, 371-378 (1988) and V. Rialet und L. Meijer, Anticancer Res. 11, 1581-1590 (1991), as required. For purification of the p34$^{cdc2}$/cyclin B$^{cdc13}$ kinase, the supernatant of the oocytes is introduced onto p9$^{CKShs}$ Sepharose grains produced from recombinant human protein p9$^{CKShs}$, as described in L. Azzi et al., Eur. J. Biochem. 203, 353-360 (1992). After 30 minutes at 4° C. under constant rotation, the grains are washed thoroughly and the active p34$^{cdc2}$/cyclin B$^{cdc13}$ kinase is eluted with free protein p9$^{CKShs}$ (3 mg/ml). The kinase eluted is tested as described in L. Meijer et al., EMBO J. 8, 2275-2282 (1989) and EMBO J. 10, 1545-1554 (1991), using histone H1 as the substrate. In this test, the compounds of the formula I and their pharmaceutically acceptable salts have an inhibiting concentration IC$_{50}$ [µmol/l] of 0.01 to 10, usually of 0.05 to 1.

As can already be expected on the basis of the inhibiting action on the enzyme p34$^{cdc2}$/cyclin B$^{cdc13}$ kinase described above, the compounds of the formula I and their pharmaceutically acceptable salts have antiproliferative properties which can be demonstrated directly in another test as follows: here, the inhibiting action of the compounds of the formula I on the growth of human T24 bladder carcinoma cells is determined. These cells are incubated in "Eagle's minimal essential medium", to which 5% (v/v) of foetal calf serum is added, in a humidified incubator at 37° C. and 5 percent by volume CO$_2$ in air. The carcinoma cells (1000-1500) are seeded into 96-well microtitre plates and incubated overnight under the abovementioned conditions. The test substance is added in serial dilutions on day 1. The plates are incubated under the abovementioned conditions for 5 days. During this period of time, the control cultures pass through at least 4 cell divisions. After the incubation, the cells are fixed with 3.3% (W/V) aqueous glutaraldehyde solution, washed with water and stained with 0.05% (weight/volume) aqueous methylene blue solution. After washing, the dye is eluted with 3% (W/V) aqueous hydrochloric acid. Thereafter, the optical density (OD) per well, which is directly proportional to the cell count, is measured with a photometer (Titertek multiskan) at 665 nm. The IC$_{50}$ values are calculated with a computer system using the formula $$\frac{OD_{665}(\text{Test})\text{minus } OD_{665}(\text{Initial})}{OD_{665}(\text{Control})\text{minus } OD_{665}(\text{Initial})} \times 100.$$

The IC$_{50}$ values are defined as that concentration of active compound at which the number of cells per well at the end of the incubation period is only 50% of the cell count in the control cultures. IC$_{50}$ values in the micromolar range can be found with compounds of the formula I.

The efficacy of the compounds of the invention as inhibitors of c-abl protein-tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris.HCl, pH 7.5, 10 mM MgCl$_2$, 10 µM Na$_3$VO$_4$, 1 mM DTT and 0.06 µCi/assay [γ$^{33}$ P]-ATP (5 µM ATP) using 30 µg/mL poly-Ala,Glu,Lys,Tyr-6:2:5:1 (Poly-AEKY, Sigma P1152) in the presence of 1% DMSO. Reactions are terminated by adding 10 μL of 250 mM EDTA and 30 μL of the reaction mixture is transferred on to Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 μL/well of Microscint™ (Packard).

Using this test system, compounds of the formula I show $IC_{50}$ values of inhibition in the range of 0.005 to 50 μM, usually between 0.05 and 5 μM.

Inhibition of the enzyme activity of KDR protein tyrosine kinase can be determined as follows: The kinase domain of KDR is expressed as GST-fusion protein using the baculovirus system. The in vitro kinase assay is performed in 96-well plates using the recombinant GST-fused kinase domains expressed in baculovirus and purified over glutathione-Sepharose. $^{33}P$-ATP (Amersham) is used as the phosphate donor, and the polyGluTyr(4:1) peptide (Sigma) is used as acceptor. The buffer is composed as follows: 29 mM Tris-HCl, pH 7.5; 10 mM $MgCl_2$, 1 μM $MnCl_2$, 8 μM ATP, 0.2 μCi $^{33}P$-ATP, 8 μg/ml polyGluTyr. The reaction os carried out in a volume of 30 μl for 10 min at room temperature in the presence of either 1% DMSO or the test compound of formula I at the required concentration in 1% DMSO or the compound of formula I at the required concentration in 1% DMSO. The reaction is stopped by the addition of ethylenediaminetetraacetic acid to a final concentration of 60 mM. The assay mixture is then transferred onto a Immobilon-PVF membrane (Millipore), which is subsequently washed four times with 0.05% $H_3PO_4$ and once with ethanol. After drying, 10 td/well of Microscint Cocktail (Packard) is added and scintillation counting is performed (Hewlett-Packard Top Count). $IC_{50}$ values are calculated by linear regression analysis of the percentage inhibition of each test compound in duplicate, at three concentrations (usually 0.01, 0.1 and 1 μM or 0.1, 1 and 10 μM). $IC_{50}$ values obtained with compounds of the formula I usually are in the range from 0.005 to 100 μM, preferably from 0.01 to 10 μM.

The inhibition of VEGF-induced KDR-receptor autophosphorylation can be confirmed with a further in vitro experiment in cells: transfected CHO cells, which permanently express human VEGF receptor (KDR), are seeded in complete culture medium (with 10% fetal calf serum =FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours' incubation at 37° C., recombinant VEGF is added; the final VEGF concentration is 20 ng/ml). After a further five minutes' incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an antiphosphotyrosine antibody coupled with alkaline phosphatase (PY20: AP from Transduction Laboratories). The (plates are washed again and the) binding of the antiphosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the $ED_{50}$ (effective dose for 50% inhibition). Compounds of the formula I here show an $ED_{50}$ in the range of 0.005 to 50 μM, usually between 0.05 and 5 M.

The activity as inhibitor of PKB can be determined as follows:

To fully activate PKB, the enzyme is exposed to catalytic amounts of PDK1. GST-PKB (100 ng, Specific Activity: 0.2 nmoles/mg/mins) is incubated for 30 min at room temperature (rt) with purified recombinant GST-PDK1 (1 ng, SA: 2 nmoles/min/mg). The activation is performed as follows: 0.1 μg of GST-PDK1 (0.05 μl) and 10 μg of GST-PKB (0.45 μl) are mixed in a total volume of 0.75 μl containing 15 μM ATP, 3 mM $MgCl_2$, 20 mM Hepes (pH 7.6) for 30 mins at rt. The reaction is subsequently stopped by adding 0.25 μl containing 30% glycerol (w/w) and 0.06 μl of 500 mM EDTA. 100-500 ng (0.01-0.05 μl) activated GST-PKB is incubated in a final volume of 30 μl with 10 μM of the LRRPRTRSFS peptide, 10 mM Mg-acetate, 50 mM MOPS (PH 7.5), 1 mM DTT and 300 μg/ml BSA, 20 μM ATP (0.1 μCi gamma-$^{33}P$-ATP). The reaction is carried out for 30 min at rt in the presence of either 1% DMSO or the text compound of the formula I at the required concentration in 1% DMSO. The reaction is terminated by the addition of 20 μl 125 mM EDTA. 30 ill of each sample is spotted onto P81 Whatman and the paper squares processed as described in Ferrari, S. and Thomas, G. (1991) Meth. Enzymol. 200, 159-169. $IC_{50}$ values are calculated by linear regression analysis of the percentage inhibition of each compound in duplicate. $IC_{50}$ values for compounds of the formula I are in the range from 0.005 to 100 μM, for preferred compounds between 0.01 and 5 μM.

In addition to or instead of inhibiting the above-mentioned protein kinases, the compounds of formula I also inhibit other tyrosine protein kinases that are involved in the signal transmission mediated by trophic factors, for example kinases of the src kinase family, such as especially the c-src kinase, lck and fyn; kinases of the EGF family, for example the c-erbB2 kinase (HER-2), the c-erbB3 kinase, the c-erbB4 kinase; members of the PDGF tyrosine protein kinase family, for example the PDGF receptor, CSF-1, c-Kit, VEGF-R and FGF-R; and the insulin-like growth factor I receptor (IGF-R) kinase, and also serine/threonine kinases, for example protein kinase C, all of which play a part in growth regulation and transformation in mammal cells, including human cells.

The inhibition of the c-erbB2 tyrosine kinase (HER-2) can be determined, for example, analogously to the method used for EGF-R-PTK (see C. House et al., Europ. J. Biochem. 140, 363-367 (1984)). The c-erbB2 kinase can be isolated and its activity determined in accordance with protocols known per se, for example according to T. Akiyama et al., Science 232, 1644 (1986).

The compounds of formula I that inhibit the protein kinase activities mentioned, especially tyrosine and/or the serine/threonine protein kinases mentioned above, can therefore be used in the treatment of protein kinase dependent diseases, especially diseases depending on c-MET, CDK-1, KDR, c-abl or PKB, or any combination of two or more of the mentioned kinases. Protein kinase dependent diseases are especially proliferative diseases, preferably a benign or especially malignant tumour, more preferably carcinoma of the brain, kidney, liver, adrenal gland, bladder, breast, stomach (especially gastric tumors), ovaries, colon, rectum, prostate, pancreas, lung, vagina, thyroid, sarcoma, glioblastomas, multiple myeloma or gastrointestinal cancer, especially colon carcinoma or colorectal adenoma, or a tumour of the neck and head, an epidermal hyperproliferation, especially psoriasis, prostate hyperplasia, a neoplasia, especially of epithelial character, preferably mammary carcinoma, or a leukaemia, especially as far as c-Met is involved. They are able to bring about the regression of tumours and to prevent the formation of tumour metastases and the growth of (also micro)metastases. In addition they can be used in epidermal hyperproliferation (e.g. psoriasis), in prostate hyperplasia, in the treatment of neoplasias, especially of epithelial character, for example mammary carcinoma, and in leukaemias. It is also possible to use the compounds of formula I in the treatment of diseases of the immune system insofar as several or, especially, individual tyrosine protein kinases and/or (further) serine/threonine protein kinases are involved; furthermore, the compounds of formula I can be used also in the treatment of diseases of the central or peripheral nervous system where signal transmission by at least one tyrosine protein kinase and/or (further) serine/threonine protein kinase is involved.

Especially compounds of formula I that show inhibition of c-Met are useful in the treatment of colon cancer, including metastases, e.g. in the liver, and of non-small-cell lung carcinoma. A compound of formula I may also be used in the treatment of hereditary papillary renal carcinoma (Schmidt, L. et al. Nat. Genet. 16, 68-73, 1997) and other proliferative diseases in wich c-MET is overexpressed or constitutively activated by mutations (Jeffers, M. and Vande Woude, G. Oncogene 18, 5120-5125, 1999; and reference cited therein) or chromosomal rearrangements (e.g. TPR-MET; Cooper, C. S. et al. Nature 311, 29-33, 1984; Park, M. et al. Cell 45, 895-904, 1986).

There are also experiments to demonstrate the antitumor activity of compounds of the formula I in vivo:

Female Balb/c hairless mice with s.c. transplanted human bladder tumours T24 can be used to determine the anti-tumour activity. On day 0, with the animals under peroral forene narcosis, approximately 25 mg of a solid tumour are placed under the skin on the animals' left flank and the small incised wound is closed by means of suture clips. On day 6 after the transplantation, the mice are divided at random into groups of 6 animals and treatment commences. The treatment is carried out for 15 days with peroral, intravenous or intraperitoneal administration once daily (or less frequently) of a compound of formula I in dimethyl sulfoxide/Tween80/sodium chloride solution in the various doses. The tumours are measured twice a week with a slide gauge and the volume of the tumours is calculated.

As an alternative to cell line A-431, other cell lines may also be used in the same manner, for example:

the MDA-MB 468 breast adenocarcinoma cell line (ATCC No. HTB 132; see also In Vitro 14, 911-15 [1978]);
the MDA-MB 231 breast carcinoma cell line (ATCC No. HTB-26; see also In Vitro 12, 331 [1976]);
the Colo 205 colon carcinoma cell line (ATCC No. CCL 222; see also Cancer Res. 38, 1345-55 [1978]);
the DU145 prostate carcinoma cell line DU 145 (ATCC No. HTB 81; see also Cancer Res. 37, 4049-58 [1978]); and
the PC-3 prostate carcinoma cell line PC-3 (especially preferred; ATCC No. CRL 1435; see also Cancer Res. 40, 524-34 [1980]).
the A549 human lung adenocarcinoma (ATCC No. CCL 185; see also Int. J. Cancer 17, 62-70 [1976]),
the NCl—H596 cell line (ATCC No. HTB 178; see also Science 246, 4914 [1989]);
the pancreatic cancer cell line SUIT-2 (see Tomioka et al., Cancer Res. 61, 7518-24 [2001]).

The compounds of the formula I can be prepared according to methods that are, in principle, known in the art.

Preferably, they are prepared by reacting a compound of the formula II

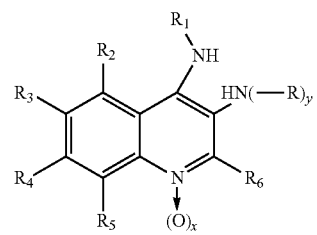

(II)

wherein x, y, $R_1$, $R_2$, $R_3$, $R_4$, $R_5$ and $R_6$ are as mentioned for a compound of the formula I and y and R are as defined below under a), b) or c), respectively, a) for the manufacture of a compound of the formula I wherein X is C=O and the dashed line in formula I bonding X to N is absent, y is 1 and R is hydrogen or an organic moiety that can be bound to nitrogen, with an active derivative of a compound of the formula III

 A-X-A (III)

wherein X is C=O and wherein each A, independently of the other, is a carbonyl-activating group;

b) for the manufacture of a compound of the formula I wherein X is C=S and the dashed line in formula I bonding X to N is absent, y is 1 and R is hydrogen or an organic moiety that can be bound to nitrogen, with $CS_2$ or Cl—C(=S)—Cl; or c) for the manufacture of a compound of the formula I wherein X is ($CR_7$) wherein $R_7$ is hydrogen or an organic or inorganic moiety with the proviso that then the dashed line bonding X to N is a bond, so that X is bound to the adjacent N via a double bond, and with the proviso that then y is zero, or y is 1 and then —R is –0, with an activated derivative of a compound of the formula IV

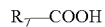 $R_7$—COOH (IV)

wherein $R_7$ is hydrogen or an organic or inorganic moiety; wherein functional groups which are present in the starting compounds in processes a) to c) and are not intended to take part in the reaction, are present in protected form if necessary, and protecting groups that are present are cleaved, wherein said starting compounds may also exist in the form of salts provided that a salt-forming group is present and a reaction in salt form is possible;

and, if desired, transforming an obtainable compound of formula I into a different compound of formula I, transforming a salt of an obtainable compound of formula I into the free compound or a different salt, or an obtainable free compound of formula I into a salt; and/or separating an obtainable mixture of isomers of compounds of formula I into the individual isomers.

In the following, more detailed description of the preferred process conditions, x, y, $R_1$, $R_2$, $R_3$, $R_4$, $R_5$, $R_7$, X, $C_{act}$ and R have the meanings given for compounds of the formula I, if not indicated otherwise.

Detailed Description of Preferred Reaction Conditions

The reaction described under (a) preferably takes place under conditions known in the art, especially in an appropriate solvent, such as a halo-lower alkane, e.g. dichloromethane, or a lower alkylnitrile, such as acetonitrile, and under elevated temperatures, preferably in the range from 40° C. to the reflux temperature of the reaction mixture, especially under reflux. In the compound of the formula III, each A is, independently of the other, preferably halo, trichloromethyl, succinimido or 1-imidazolo. For example, if the compound of the formula III is trichloromethyl chloroformate, the reaction preferably takes place under anhydrous conditions in an appropriate aprotic solvent, e.g. a halogenated hydrocarbon, such as dichloromethane, at preferred temperatures between 0 and 50° C., e.g. at room temperature.

The reaction under (b) with $CS_2$ or Cl—C(=S)—Cl preferably takes place in the presence of a base, especially a tertiary amine, such as tri-lower alkylamine, preferably triethylamine, or pyridine, an alkalimetal carbonate or -bicarbonate, e.g. sodium bicarbonate, or a metal hydroxide, especially an alkali metal hydroxide, such as sodium- or potassium hydroxide, in a polar organic solvent, especially an alcohol, at temperatures between 10° C. and the reflux temperature, more preferably between 20° C. and 100° C.

The reaction described under (c) preferably takes place in the presence of an active derivative of a compound of the formula IV ($C_{act}$=activated COOH; or CHO) as solvent or other appropriate solvents or solvent mixtures at preferred temperatures between 30° C. and the reflux temperature of the reaction mixture, more preferably under reflux. An activated derivative of a compound of the formula IV is especially a tri-lower alkyl orthoester of the carbonic acid of formula IV, especially a tri-ethyl derivative, such as triethylorthoformate ($R_7$=H), or a succinimide ($R_7$=succinimido) or imidazolide ($R_7$=1-imidazolo). Alternatively, the respective reactive derivative of an acid of the formula IV is formed in situ, e.g. in the presence of polyphosphoric acid (also as solvent) at elevated temperatures, e.g. between 100 and 140° C.

Compounds of formula I can be transformed into different compounds of formula I.

Especially, the following transformations are of interest:

In compounds of the formula I wherein $R_1$ carries a cyano or cyano-lower alkyl substituent, this substituent can be converted into an aminomethyl or aminomethyl-lower alkyl group, respectively, by hydrogenation, e.g. with hydrogen in the presence of an appropriate catalyst, such as a Raney catalyst, especially Raney-Ni, in an appropriate solvent, such as an alcohol, especially methanol or ethanol, or a cyclic ether, such as tetrahydrofurane, or a mixture thereof, in the presence of ammonia, preferably at temperatures between 0° C. and 50° C., e.g. at room temperature.

In compounds of the formula I wherein $R_1$ carries a cyano or cyano-lower alkyl substitutent or $R_7$ is any one of these substituents, this substituent can be converted into a N-hydroxyamidino or N-hydroxyamidino-lower alkyl group, respectively, by reaction with a hydroxylamine salt of an organic or inorganic acid, e.g. a hydroxylamine halogenide, in a polar solvent, e.g. a di-lower alkyl lower alkanoylamide, especially dimethyl formamide, in the presence of water at preferred temperatures between 10 and 100° C., e.g. at 20 to 75° C., in the presence of a base, especially an alkali metal carbonate, such as sodium carbonate.

In compounds of the formula I wherein $R_1$ is 2-haloaryl, e.g. 2-chlorophenyl, the halogen can be removed by hydrogenation with hydrogen in an appropriate solvent, e.g. in an alcohol, such as methanol, or a N,N-di-lower alkyl-loweralkanoylamide, such as dimethylformamide, or a mixture thereof, and a catalyst, such as a noble metal on a carrier material, e.g. palladium on charcoal (Pd—C), at preferred temperatures between 0 and 50° C., e.g. at room temperature, to the corresponding compound wherein $R_1$ is aryl, e.g. phenyl.

In a compound of the formula I wherein a hydroxyamidino substituent is present (e.g. as mentioned in the last paragraph), this substituent can be converted into the corresponding amidino substituent by hydrogenation in the presence of an acid, such as hydrochloric acid, and a catalyst, preferably a Raney metal catalyst, such as Raney-Ni, preferably at elevated temperatures, e.g. between 30 and 70° C., e.g. at 50° C.

Compounds of the formula I wherein x and y or one of them are zero can be converted into the corresponding N-oxide compounds (x, y or both=1, R=→O) by oxidation in the presence of a peroxide, especially a peroxybenzoic acid derivative, such as 3-chloroperoxybenzoic acid, in the presence of a base, e.g. an alkali metal carbonate, such as sodium carbonate, and in an appropriate solvent, e.g. a halogenated hydrocarbon, such as chloroform or methylene chloride.

A compound of the formula I wherein x is 1 and $R_6$ is hydrogen can be transformed into the corresponding compound wherein x is zero an $R_6$ is arylcarbonylamino by reaction with the corresponding aryl isocyanate, especially benzoyl isocyanate, in an appropriate solvent, e.g. a halogenated hydrocarbon, such as methylene chloride or chloroform, preferably at elevated temperatures, e.g. under reflux.

A compound of the formula I wherein $R_6$ is arylcarbonylamino can be converted into the corresponding compound of the formula I wherein $R_6$ is amino by reaction with an alkali metal alcoholate in the corresponding alcohol, e.g. sodium methanolate in methanol, at elevated temperatures, e.g. under reflux.

A compound of the formula I wherein x is 1 and $R_6$ is hydrogen can be transformed into the corresponding compound wherein x is zero an $R_6$ is cyano by reaction with an metal cyanide, e.g. an alkali metal cyanide, especially potassium cyanide, in the presence of a base, e.g. a tertiary nitrogen base, such as a tri-lower alkylamine, e.g. triethylamine, in a polar solvent, e.g. a di-lower alkyl alkanoylamide, such as dimethylformamide, at elevated temperatures, e.g. between 80 and 120° C., for example between 100 and 110° C.

A compound of the formula I wherein x is 1 and $R_6$ is hydrogen can be transformed into the corresponding compound wherein x is zero an $R_6$ is halo by reaction with an inorganic halogenide, e.g. $POCl_3$, in an appropriate solvent, e.g. a mixture of a di-lower alkyl alkanoylamide, such as dimethylformamide, and an aromatic hydrocarbon, e.g. toluene, at elevated temperatures, e.g. between 50 and 90° C.

A compound of the formula I wherein $R_6$ is halo can be converted into a compound of the formula I wherein $R_6$ is amino substituted by one or two moieties selected from the group consisting of lower alkyl, substituted lower alkyl moieties, aryl, cycloalkyl and mercapto-lower alkyl by reaction with the corresponding primary or secondary amine, respectively, in an appropriate solvent, e.g. an alcohol, especially methanol or 2-ethoxyethanol, at temperatures between 100 and 130° C. (if necessary in a sealed reaction vessel, e.g. a sealed tube).

A compound of the formula I wherein X is ($CR_7$) and $R_7$ is halogen can be obtained from the corresponding compound wherein $R_7$ is hydrogen by reaction with the corresponding halogen succinimide, especially N-bromosuccinimide, in the presence of the corresponding iron(III)halogenide, especially $FeBr_3$, in the absence or presence of an appropriate solvent at elevated temperatures, preferably under reflux.

A compound of the formula I wherein X is ($CR_7$) and $R_7$ is cyano can be obtained from the corresponding compound wherein $R_7$ is —$CONH_2$ by reaction with an inorganic acid halogenide, especially $POCl_3$, in an appropriate tertiary amine, especially pyridine, preferably at elevated temperatures, more preferably between 25 and 80° C. Alternatively, the compound can be obtained from a compound of the formula I wherein $R_7$ is bromo (as obtainable in the last paragraph) by reaction in the presence of CuCN and a catalyst, especially), tris(dibenzylideneacetone)dipalladium chloroform adduct and 1,1'-bis(diphenylphosphino)ferrocene, and of tetraethylammonium canide in an appropriate solvent, e.g. a cyclic ether, such as dioxane, at preferred temperatures (if necessary in a sealed tube) between 100 and 150° C., e.g. at 140° C.

A compound of the formula I wherein X is C=O, y is 1 and R is unsubstituted or substituted alkyl, especially lower alkyl, can be obtained by converting the corresponding compound of the formula I wherein R is H with a halogenide, especially iodide, such as lower alkyl iodide, in the presence of a strong base, especially an alkali metal hydride, e.g. sodium hydride, in an appropriate aprotic solvent, e.g. a N,N-di-lower alkyl-lower alkanoylamide, at preferred temperatures in the range from 0 to 50° C., e.g. at room temperature, into said compound.

A compound of the formula I wherein X is C=O, y is 1 and R is aryl, especially phenyl, can be obtained by converting the corresponding compound of the formula I wherein R is H with an arylboronic acid, especially phenylboronic acid, in the presence of anhydrous cupric acetate and a tertiary amine, e.g. a tri-lower alkylamine, such as triethylamine, in an appropriate aprotic solvent, especially a halogenated hydrocarbon, such as dichloromethylene, at preferred temperatures between 0 and 50° C., e.g. at room temperature, into said compound.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-)crystallization, and the like.

Starting Materials

The starting materials of the formulae II, III and IV are known, commercially available and/or can be prepared according to methods known in the art.

A compound of the formula II wherein R is hydrogen and y is 1 is preferably prepared by hydrogenation of a compound of the formula V

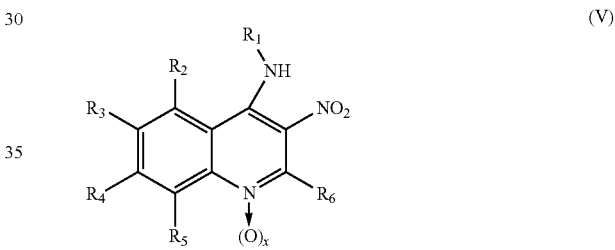

(V)

wherein the substitutents and symbols are defined as for compounds of the formula I (x is preferably zero), in the presence of an appropriate catalyst, e.g. a skeleton based catalyst, such as Raney-Ni, with hydrogen in an appropriate solvent, e.g. an alcohol, such as methanol, at preferred temperatures between 0 and 50° C., e.g. at room temperature.

The corresponding compounds of the formula II wherein R is an organic moiety that can be bound to nitrogen, especially a carbon-bound one, can be prepared by reaction of a compound of formula II wherein R is hydrogen and y is 1 (see preceding paragraph) with a compound of the formula VI

R-L   (VI)

wherein R is an organic moiety bound to L via a carbon atom and L is a leaving group, especially halo, such as chloro, bromo or iodo, or arylsulfonyl, e.g. toluenesulfonyl, in an appropriate solvent, preferably in the presence of a tertiary nitrogen base, such as pyridine or triethylamine. Alternatively, a compound of the formula II wherein R is hydrogen and y is 1 can be reacted with an aldehyde of the formula VI*

R*—CHO   (VI*)

wherein R* is as an organic moiety bound to the moiety —CHO via a carbon atom, followed by reduction of the resulting enamine with an appropriate reductant, e.g. a complex hydride, such as an alkalimetal cyanoborohydride, e.g. sodium-cyanoborohydride, e.g. in the same solvent and at temperatures between −10 and 40° C., e.g. at 10° C., the total reaction summing up to reductive amination.

A compound of formula V is preferably prepared by reacting a compound of the formula VII

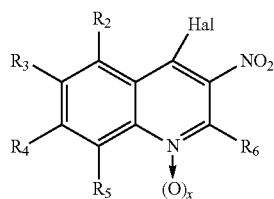
(VII)

wherein Hal is halo, especially chloro, and the other moieties and symbols have the meanings indicated for compounds of the formula I (x is preferably zero), with a compound of the formula VIII

R₁—NH₂ (VIII)

wherein $R_1$ is as defined for a compound of the formula I, in an appropriate solvent, preferably a lower alkylcarboxylic acid, such as acetic acid, at preferred temperatures between 10° C. and reflux temperature of the reaction mixture, e.g. between 20 and 140° C.

A compound of the formula VII can be prepared by reacting a compound of the formula IX

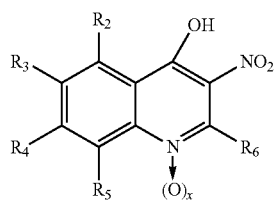
(IX)

wherein the moieties and symbols have the meanings indicated for a compound of the formula I (x is preferably zero), with an inorganic acid halogenide, especially POCl₃ (preferably without solvent) at elevated temperatures, e.g. between 100 and 150° C. or under reflux.

A compound of the formula IX is known in the art, can be synthesized according to methods known in the art and/or is commercially available. For example, it can be synthesized by reacting a compound of the formula X

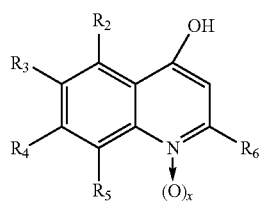
(X)

wherein the moieties and symbols have the meanings indicated for a compound of the formula I (x is preferably zero) with nitric acid (aqueous) at a preferred temperature between 50 and 100° C., e.g. at 85° C.

A compound of the formula IX, especially wherein $R_3$ has one of the meanings given for a compound of the formula I other than hydrogen, especially halo, especially fluoro, alkoxy, especially lower alkoxy, substituted or preferably unsubstituted aryl, especially phenyl, or substituted or preferably unsubstituted alkyl, especially lower alkyl, and the other moieties and symbols are as defined for a compound of the formula I but x is zero can alternatively be synthesized by reacting a compound of the formula XI

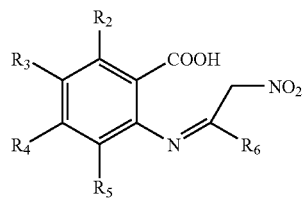
(XI)

wherein the moieties and symbols have the meanings indicated for a compound of the formula I, with an anhydride of a carbonic acid, especially acetic anhydride, preferably in the presence of an alkali metal salt of a carboxylic acid, e.g. potassium acetate, at a preferred temperature between 50 and 150° C., e.g. at ca. 100 to 140° C.

A compound of the formula XI wherein $R_3$ is substituted or preferably unsubstituted alkyl and the other symbols have the meanings indicated for a compound of the formula XI can be obtained, for example, by reacting a compound of the formula XII

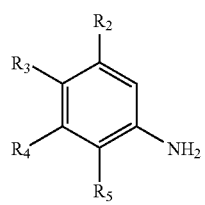
(XII)

wherein $R_2$, $R_4$ and $R_5$ are as indicated for a compound of the formula I, especially each is hydrogen, and $R_3$ is substituted or preferably unsubstituted alkyl, with chloralhydrate in the presence of an alkali metal sulfate, e.g. sodium sulfate, in an aqueous solvent with subsequent addition of a hydroxylamine salt, e.g. the hydrochloride salt, and treatment with conc. sulphuric acid. The result is a compound of the formula XIII

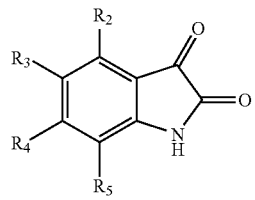
(XIII)

wherein the moieties have the meanings indicated for a compound of the formula XII. This compound is then reacted with a peroxide, preferably hydrogen peroxide, in the presence of a base, e.g. an alkali metal hydroxide, in an aqueous medium, to yield a compound of the formula XIV

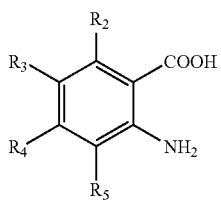

wherein the symbols have the meanings indicated for a compound of the formula XII. The compound of the formula XIV is then reacted to the corresponding compound of the formula XI by reacting nitromethane in the presence of an alkali metal hydroxide, especially sodium hydroxide, at preferred temperatures between approximately 0 and 30° C., e.g. between 0° C. and room temperature, then pouring the product under cooling to approximately 0° C. into conc. HCl and adding the compound of the formula XIV and further conc. HCl, subsequently allowing for further reaction at preferred temperatures between 0° C. and room temperature.

A compound of the formula XI wherein % is unsubstituted or substituted aryl, especially phenyl, and the other moieties have the meanings given under formula XI, can, for example, be synthesized by reacting a compound of the formula XIV given above wherein $R_3$ is unsubstituted or substituted aryl. This class of compounds of formula XIV is known or can be prepared according to methods known in the art. For example, the compound of formula XIV wherein $R_3$ is phenyl can be prepared by reacting a compound of the formula XV

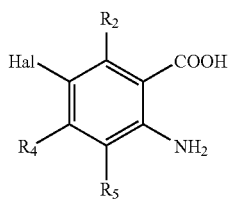

wherein Hal is halo, especially bromo, and the other symbols have the meanings given for compounds of the formula I, in an appropriate solvent, e.g. a di-lower alkyl-lower alkanoylamide, especially dimethylformamide, under an inert gas, e.g. argon, in the presence of a base, e.g. an alkali metal carbonate, preferably potassium carbonate, with tetrakis-triphenyl-phosphin-palladium at preferred temperatures between 50 and 100° C., e.g. about 80° C.

A compound of the formula XI wherein $R_3$ is alkoxy, especially lower alkoxy, can be prepared by reacting a compound of the formula XVI

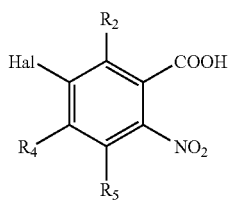

wherein Hal is halo, preferably chloro, and the other symbols have the meanings indicated for compounds of the formula I, with a hydroxide base, e.g. an alkali metal hydroxide, such as sodium hydroxide, in an aqueous medium at elevated temperatures, e.g. under reflux, to the corresponding compound wherein instead of "Hal" a hydroxy group is present. This hydroxy compound is then, by reaction with an alkyl halogenide or alkyl arylsulfonate, e.g. an alkyl iodide, in an appropriate solvent, e.g. a di-lower alkyl-lower alkanoylamide, such as dimethylformamide, in the presence of a base, e.g. an alkali metal carbonate, at preferred temperatures between 40 and 90° C., e.g. at approximately 75° C., transformed into a compound of the formula XVII

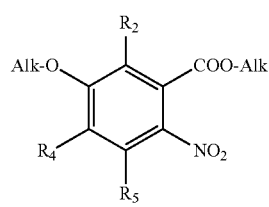

wherein Alk is alkyl and $R_2$, $R_4$ and $R_5$ are as defined for a compound of the formula I. The compound of formula XVII is then hydrolyzed to the free carbonic acid (COOH instead of COO-Alk in formula XVII) by reaction with a base, such as an alkali metal hydroxide, e.g. sodium hydroxide, in an appropriate solvent, e.g. an alcohol, such as ethanol, at preferred temperatures between 0 and 50° C., e.g. at room temperature. The nitro group in the resulting carboxylic acid is then reduced to an amino group, preferably by hydrogenation in the presence of a carrier-based catalyst, e.g. Pd on charcoal, in an appropriate solvent, e.g. an alcohol, such as ethanol, at preferred temperatures between 0 and 50° C., e.g. at room temperature, and the result is a compound of the formula XIV given above wherein $R_3$ is alkoxy and the other moieties are as defined for a compound of the formula I. This compound can then be transformed into the corresponding compound of the formula XI by reaction with nitromethane etc. in analogy to the method described for reaction of a compound of the formula XIV to the corresponding compound of formula XI.

A compound of the formula XI wherein $R_3$ is halo, especially fluoro, and the other symbols have the meanings indicated for a compound of the formula XI can be obtained, for example, by converting a compound of the formula XV, wherein $R_3$ is halo and the other symbols have the meanings given under formula XV, by reaction with nitromethane etc. in analogy to the method described for reaction of a compound of the formula XIV to the corresponding compound of formula XI, to result in the corresponding compound of formula XI.

Other starting materials are either known in the art, can be prepared according to methods that are known in the art, e.g. in analogy to the methods described hereinabove or in the examples, and/or are commercially available.

The present invention relates also to novel starting materials and/or intermediates and to processes for their preparation. The starting materials used and the reaction conditions selected are preferably those that result in the compounds described as being preferred.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods.

Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I may however also contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

General Process Conditions

The following applies in general to all processes mentioned hereinbefore and hereinafter, while reaction conditions specifically mentioned above or below are preferred:

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralising agents, for example ion exchangers, such as cation exchangers, e.g. in the H⁺ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitrites, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in new compounds of formula I described at the beginning as being especially valuable. Special preference is given to reaction conditions that are analogous to those mentioned in the Examples.

PREFERRED EMBODIMENTS OF THE INVENTION

The invention relates especially to the use of a compound of the formula I, wherein
each of x and y is, independently of the other, 0 or 1,
$R_1$ is an organic moiety that can be bound to nitrogen,
X is C=O (especially preferred) or C=S with the proviso that then the dashed line bonding X to N is absent, so that X is bound to the adjacent N via a single bond and with the proviso that then y is 1 and R is hydrogen or an organic moiety that can be bound to nitrogen;
or X is ($CR_7$) wherein $R_7$ is hydrogen or an organic or inorganic moiety with the proviso that then the dashed line bonding X to N is a bond, so that X is bound to the adjacent N via a double bond, and with the proviso that then y is zero or y is 1 and then —R is →O;
and each of $R_2$, $R_3$, $R_4$; $R_5$ and $R_6$ independently of the others, is an organic moiety or hydrogen or an inorganic moiety;
or a pharmaceutically acceptable salt thereof,
in the treatment of a protein kinase dependent disease or for the manufacture of a pharmaceutical preparation for the treatment of a protein kinase dependent disease, or a method of treatment against said disease, comprising administering a compound of the formula I to a warm-blooded animal, especially a human, in need of such treatment. A tyrosine kinase dependent disease is preferably one depending on an (especially aberrantly highly expressed) c-MET-, CDK1-, KDR-, AbI- or PKB/Akt (=PKB)-dependent disease or a disease dependent on any two or more of the kinases just mentioned.

More preferred is the use or method according to the preceding paragraph where in the compound of the formula I, or a pharmaceutically acceptable salt thereof,
each of x and y is, independently of the other, 0 or 1,
$R_1$ is phenyl or phenyl-lower alkyl, each of which, in the phenyl moiety, is unsubstituted or substituted by up to three moieties independently selected from halogen, especially fluoro, chloro, bromo or iodo, lower alkyl, especially methyl or ethyl, halo-lower alkyl, especially trifluoromethyl, hydroxy, lower alkoxy, especially methoxy, $C_6$-$C_{14}$-aryl, especially phenyl, hydroxy-lower alkyl, especially 2-hydroxyethyl or hydroxymethyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;

or is $C_3$-$C_8$-cycloalkyl, especially cyclohexyl, or hydroxy-$C_3$-$C_8$-cycloalkyl, especially hydroxycyclohexyl;

X is C=O or C=S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethylpropyl or 2-ethyl-n-butyl; mono- or di-hydroxy-lower alkyl, especially 2,3-dihydroxy-propyl or 3-hydroxy-2,2-dimethyl-propyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;

or X is ($CR_7$) wherein $R_7$ is hydrogen or an organic or inorganic moiety that can be bound to nitrogen with the proviso that then the dashed line bonding X to N is a bond, so that X is bound to the adjacent N via a double bond, and with the proviso that then y is zero, or y is 1 and then —R is →O;

$R_2$ is hydrogen, $R_3$ is hydrogen, lower alky, especially ethyl, halo, especially fluoro, chloro or bromo, lower alkoxy, especially methoxy, or unsubstituted or substituted $C_6$-$C_{14}$-aryl, especially phenyl, hydroxyphenyl or methoxyphenyl;

$R_4$ is hydrogen or halo, especially chloro, $R_5$ is hydrogen or lower alkoxy, especially n-lower hexyloxy, and $R_6$ is hydrogen, halo, especially chloro, $C_6$-$C_{14}$-aryl, especially phenyl, $C_3$-$C_8$-cycloalkyl, especially cyclopropyl, amino, lower alkyl-amino, especially methylamino or n-butylamino, hydroxy-lower alkylamino, especially 2-hydroxyethyl-amino or $C_6$-$C_{14}$-arylcarbonylamino, especially benzoylamino.

Also preferred is a compound of the formula I, or a pharmaceutically acceptable salt thereof, as shown in the preceding two paragraphs for use in the treatment of a protein kinase dependent disease, especially one depending on an (especially aberrantly highly expressed) c-MET-, CDK1-, KDR-, Abl- or PKB/Akt (=PKB)-dependent disease or disease dependent on any two or more of the kinases just mentioned.

Especially preferred is a compound of the formula I, or a pharmaceutically acceptable salt thereof, wherein X is C=O and the other moieties are as defined under formula I, for use in the diagnostic or therapeutic treatment of a warm-blooded animal, especially a human.

More preferred is a compound of formula I, or a pharmaceutically acceptable salt therof, wherein each of x and y is, independently of the other, 0 or 1, $R_1$ is phenyl or phenyl-lower alkyl, each of which, in the phenyl moiety, is substituted by up to three moieties independently selected from halo-lower alkyl, especially trifluoromethyl, hydroxy, $C_6$-$C_{14}$-aryl, especially phenyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;

or is $C_3$-$C_8$-cycloalkyl, especially cyclohexyl, or hydroxy-$C_3$-$C_8$-cycloalkyl, especially hydroxy-cyclohexyl;

X is C=O or C=S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethyl-propyl or 2-ethyl-n-butyl; mono- or di-hydroxy-lower alkyl, especially 2,3-dihydroxy-propyl or 3-hydroxy-2,2-dimethyl-propyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;

or X is ($CR_7$) wherein $R_7$ is hydrogen or an organic or inorganic moiety that can be bound to nitrogen with the proviso that then the dashed line bonding X to N is a bond, so that X is bound to the adjacent N via a double bond, and with the proviso that then y is zero, or y is 1 and then —R is →O;

$R_2$ is hydrogen, $R_3$ is hydrogen, lower alkyl, especially ethyl, halo, especially fluoro, chloro or bromo, lower alkoxy, especially methoxy, or unsubstituted or substituted $C_6$-$C_{14}$-aryl, especially phenyl, hydroxyphenyl or methoxyphenyl;

$R_4$ is hydrogen or halo, especially chloro, $R_5$ is hydrogen or lower alkoxy, especially n-lower hexyloxy, and $R_6$ is hydrogen, halo, especially chloro, $C_6$-$C_{14}$-aryl, especially phenyl, $C_3$-$C_8$-cycloalkyl, especially cyclopropyl, amino, lower alkyl-amino, especially methylamino or n-butylamino, hydroxy-lower alkylamino, especially 2-hydroxyethyl-amino or $C_6$-$C_{14}$-arylcarbonylamino, especially benzoylamino; or a pharmaceutically acceptable salt thereof; as such or especially for use in the diagnostic or therapeutic treatment of a warm-blooded animal, especially a human.

Also more preferred is a compound of the formula I, or a pharmaceutically acceptable salt thereof, wherein each of x and y is, independently of the other, 0 or 1, $R_1$ is phenyl or phenyl-lower alkyl, each of which, in the phenyl moiety, is unsubstituted or substituted by up to three moieties independently selected from halogen, especially fluoro, chloro, bromo or iodo, lower alkyl, especially methyl or ethyl, halo-lower alkyl, especially trifluoromethyl, hydroxy, lower alkoxy, especially methoxy, $C_6$-$C_{14}$-aryl, especially phenyl, hydroxy-lower alkyl, especially 2-hydroxyethyl or hydroxymethyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;

or is $C_3$-$C_8$-cycloalkyl, especially cyclohexyl, or hydroxy-$C_3$-$C_8$-cycloalkyl, especially hydroxy-cyclohexyl;

X is C=O or C=S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethylpropyl or 2-ethyl-n-butyl; mono- or di-hydroxy-lower alkyl, especially 2,3-dihydroxy-propyl or 3-hydroxy-2,2-dimethyl-propyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;

or X is (CR$_7$) wherein R$_7$ is hydrogen or an organic or inorganic moiety that can be bound to nitrogen with the proviso that then the dashed line bonding X to N is a bond, so that X is bound to the adjacent N via a double bond, and with the proviso that then y is zero, or y is 1 and then —R is →O;

R$_2$ is hydrogen,

R$_3$ is hydrogen, lower alky, especially ethyl, halo, especially fluoro, chloro or bromo, lower alkoxy, especially methoxy, or unsubstituted or substituted C$_6$-C$_{14}$-aryl, especially phenyl, hydroxyphenyl or methoxyphenyl;

R$_4$ is hydrogen or halo, especially chloro,

R$_5$ is hydrogen or lower alkoxy, especially n-lower hexyloxy, and

R$_6$ is hydrogen, halo, especially chloro, C$_6$-C$_{14}$-aryl, especially phenyl, C$_3$-C$_8$-cycloalkyl, especially cyclopropyl, amino, lower alkyl-amino, especially methylamino or n-butylamino, hydroxy-lower alkylamino, especially 2-hydroxyethyl-amino or C$_6$-C$_{14}$-arylcarbonylamino, especially benzoylamino, for use in the treatment of a protein kinase dependent disease.

Very preferred is a compound of the formula I, or a (especially pharmaceutically acceptable) salt thereof, wherein X is C=O and the remaining radicals and symbols x, y, R, R$_1$ to R$_6$, are as defined under formula I.

Very preferred is the use according to the first or second paragraph under "Preferred Embodiments of the Invention" or the compounds according to any one of the third and fourth paragraph under "Preferred Embodiments of the Invention" or of the preceding three paragraphs where the disease to be treated is a proliferative disease, preferably a benign or especially malignant tumour, more preferably carcinoma of the brain, kidney, liver, adrenal gland, bladder, breast, stomach (especially gastric tumors), ovaries, colon, rectum, prostate, pancreas, lung, vagina, thyroid, sarcoma, glioblastomas, multiple myeloma or gastrointestinal cancer, especially colon carcinoma or colorectal adenoma, or a tumour of the neck and head, an epidermal hyperproliferation, especially psoriasis, prostate hyperplasia, a neoplasia, especially of epithelial character, preferably mammary carcinoma, or a leukaemia, especially as far as c-Met is involved.

Most preferred is the use in accordance with the present invention of a compound of the formula I, or a pharmaceutically acceptable salt thereof, as exemplified hereinbelow under 'Examples'.

Especially preferred is a novel compound of formula I, or a pharmaceutically acceptable salt thereof, for use in the therapeutic or diagnostic treatment of a warm-blooded animal, especially a human; or the use of such a novel compound of formula I, or a pharmaceutically acceptable salt thereof, in the treatment of a protein kinase dependent disease or for the manufacture of a pharmaceutical preparation for the treatment of said disease.

Especially preferred is also the use of a compound of the formula I selected from the group consisting of 1-(4-fluorophenyl)-1H-imidazo[4,5-c]quinoline and 1-n-butyl-1H-imidazo[4,5-c]quinoline, or a pharmaceutically acceptable salt thereof, for the preparation of a pharmaceutical composition for the treatment of a protein kinase dependent disease, especially a proliferative disease.

Most special preference is further given to the novel compounds of formula I mentioned in the Examples below, or a salt, especially a pharmaceutically acceptable salt, thereof.

Pharmaceutical Compositions

The invention relates also to pharmaceutical compositions comprising a compound of formula I, to their use in the therapeutic (in a broader aspect of the invention also prophylactic) treatment or a method of treatment of a protein kinase dependent disease, especially the preferred diseases mentioned above, to the compounds for said use and to the preparation of pharmaceutical preparations, especially for said uses.

The pharmacologically acceptable compounds of the present invention may be used, for example, for the preparation of pharmaceutical compositions that comprise an effective amount of a compound of the formula I, or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention of (=prophylaxis against) a disease that responds to inhibition of protein kinase activity, comprising an amount of a compound of formula I or a pharmaceutically acceptable salt thereof, which is effective for said inhibition, especially the in, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase; which comprises administering an (against the mentioned disease) prophylactically or especially therapeutically effective amount of a compound of formula I according to the invention, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, is preferably from approximately 3 mg to approximately 10 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be produced prior to use. The pharmaceutical compositions may be sterilised and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, for example for identification purposes or to indicate different doses of active ingredient.

A compound of the formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659, 516 or it can be administered, e.g., in the form as it is marketed, e.g. under the trademark FASLODEX™.

The term "topoisomerase I inhibitors" as used herein includes, but is not limited to topotecan, irinotecan, 9-nitro-camptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., In the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the Insulin-like Growth Factor I Receptor (IGF-IR) and the Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00137502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632, KRN-633 and SU5416;

anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having antiproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, for example the administration of hormones or especially radiation. A compound of formula I may in particular be used as a radiosensitizer, especially for the treatment of tumors which exhibit poor sensitivity to radiotherapy.

EXAMPLES

The following examples serve to illustrate the invention without limiting the scope thereof:

Abbreviations
conc. concentrated
dec. under decomposition
DMF dimethyl formamide
ES-MS electrospray mass spectrometry
h hour(s)
l litre(s)
min minute(s)
mp melting point in ° Celsius
MS mass spectrum
rt room temperature
$t_{ret}$ HPLC retention time in min
TFA trifluoroacetic acid
THF tetrahydrofurane
tlc thin layer chromatography Where no temperatures are given, the reaction takes place at ambient (room) temperature. Ratios of solvents (e.g. in eluents or solvent mixtures) are given in volume by volume (v/v).

Avicel is microcrystalline cellulose (FMC, Philadelphia, USA).
PVPPXL is polyvinylpolypyrrolidone, cross-linked (BASF, Germany).
Aerosil is silcium dioxide (Degussa, Germany).
Grad 1 20% B→100% B in 13 min+5 min 100% B
Grad 2 Linear gradient over 7 min of acetonitrile/0.09 TFA from 1:49 to 1:0 and 3 min at 1:0, flow rate 2.0 ml/min.
Grad3 5% B→40% B in 7.5 min+7 min 40% B
solvent A: water+0.1% TFA
solvent B: acetonitrile+0.1% TFA Detection is in both cases at 215 nm, flow rate 1.0 ml/min if not indicated otherwise. Column: Nucleosil C18 reversed phase column (250×4.6 nm, 5 µm, 100 Å; Macherey & Nagel, Düren, FRG).

Example 1

1-(4-Fluoro-phenyl)-1H-imidazo[4,5-c]quinoline

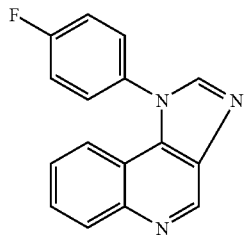

0.5 g (1.97 mmol) N+(4-fluoro-phenyl)-quinoline-3,4-diamine (Example 1d) in 20 ml triethylorthoformate are heated at reflux for 3 h. The solvent is evaporated, the residue dissolved in ethylacetate and treated once with charcoal. The charcoal is filtered on Hyflo® Super Cel diatomaceous earth, and the solution is concentrated in vacuo. After adding diethyl ether-hexane to the above solution and cooling with ice-water, the title compound separated from the solution as crystalline solid. mp: 161-162° C.; MS: 264 (M⁺+1); HPLC: $t_{ret}$=6.83 min (Grad 1).

Example 1a

3-Nitro-quinolin-4-ol

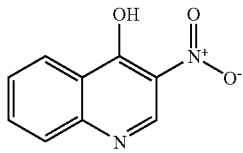

5 g (34 mmol) 4-hydroxyquinoline are added in small portions to nitric acid (66%) heated at 85° C. The reaction mixture is stirred for 50 min at this temperature. 150 ml water are heated to 100° C. and the reaction mixture is added slowly through a dropping funnel to the boiling water. The yellow precipitate which is formed is filtered off and washed with hot and cold water and acetone to become almost colorless. The title compound is dried at 60° C. under vacuum. mp: 357-358° C.; MS: 191 ($M^+$+1); HPLC: $t_{ret}$=8.73 min (Grad 3).

Example 1b

4-Chloro-3-nitro-quinoline

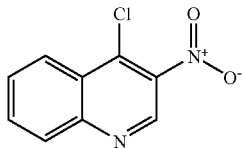

5.5 g (29 mmol) 3-nitro-quinolin-4-ol (Example 1a) in 25 ml $POCl_3$ are heated for 2 h to keep at 130° C. The mixture is cooled to rt and poured into ice-water. The precipitate is filtered off, washed with ice-cold water, and dissolved in $CH_2Cl_2$. The organic phase is washed with cold 0.1N NaOH (1×) and with cold water (2×). After drying over $MgSO_4$, the solvent is evaporated to dryness. The residue is stirred in hexane. The title compound is isolated as a powder and is dried at 60° C. under vacuum. mp: 121-122° C.; NMR ($CDCl_3$): 9.26/s (1H), 8.44/d and 8.21/d (2H), 7.95/t and 7.82/t (2H); HPLC: $t_{ret}$=1.64 min (Grad 1).

Example 1c

(4-Fluoro-phenyl)-3-nitro-quinolin-4-yl)-amine

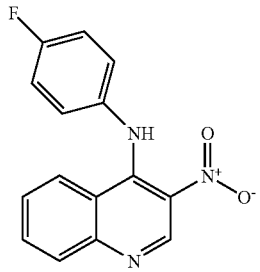

To 0.48 g (4.8 mmol) 4-fluoroaniline (Fluka) in 8 ml acetic acid, 1 g (4.8 mmol) 4-chloro-3-nitro-quinoline (Example 1b) is added at rt in one portion. The mixture is heated to keep at 1300 (reflux) and stirred for 10 min. To this mixture, ca. 30 ml water are added at rt (under stirring). A yellow precipitate is formed, which is filtered off. The filtrate is further diluted with water, and more of the title compound separates out from the reaction mixture. The precipitates are pooled, dissolved in $CH_2Cl_2$, and the organic phase is washed with 5% $NaHCO_3$ (1×) and water (3×). After drying over $MgSO_4$, the solvent is partially evaporated, and hexane is added to the solution. The title compound precipitates and is isolated as yellow crystals. mp: 153-154° C., MS: 284 ($M^+$+1); HPLC: $t_{ret}$=7.94 min (Grad 1).

Example 1d

N-4-(4-Fluoro-phenyl)-quinoline-3,4-diamine

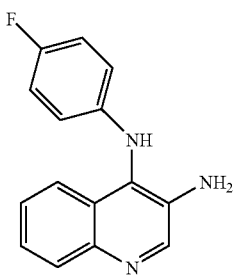

0.12 g (0.42 mmol) (4-fluoro-phenyl)-(3-nitro-quinolinyl)-amine (Example 1c) and 0.1 g Raney-Ni in 10 ml methanol are hydrogenated for about 1 h at rt and 1,013 bar. The catalyst is filtered off and washed with methanol. The solvent is evaporated on the rotary evaporator and dissolved in acetone. By adding a mixture of diethyl ether-hexane, the title compound precipitates under cooling with ice-cold water. The crystals are filtered off, washed with hexane and dried at 70° C. under vacuum. mp: 193-194° C., MS: 254 ($M^+$+1); HPLC: $t_{ret}$=7.47 min (Grad 1).

In analogy to Example 1, and starting from the common intermediate 4-chloro-3-nitro-quinoline (Example 1b) the following compounds are synthesized:

TABLE 1

| Example | Compound name | M/e$_o$ | t$_{ret}$ | mp [° C.] |
|---|---|---|---|---|
| 2 | 1-(3-Trifluoromethyl-phenyl)-1H-imidazo[4,5-c]quinoline | 314 | 7.99[3] | 183-184 |
| 3 | 4-Imidazo[4,5-c]quinolin-1-yl-phenol | 262 | 5.57[3] | n.d. |
| 4 | 1-(3,4-Dimethoxy-phenyl)-1H-imidazo[4,5-c]quinoline | 306 | 6.52[3] | 201-202 |
| 5 | 1-(4-Iodo-phenyl)-1H-imidazo[4,5-c]quinoline | 372 | 8.42[3] | 215-216 |
| 6 | 1-Biphenyl-4-yl-1H-imidazo[4,5-c]quinoline | 322 | 9.62[3] | 212-213 |
| 7 | 2-(4-Imidazo[4,5-c]quinolin-1-yl-phenyl)-ethanol | 290 | 5.58[3] | 278-279 |
| 8 | (4-Imidazo[4,5-c]quinolin-1-yl-phenyl)-acetonitrile | 285 | 6.40[3] | 163-164 |
| 9 | 2-Imidazo[4,5-c]quinolin-1-yl-ethanol[1,2] | 214 | 6.91[4] | 287-288 |
| 10 | 4-Imidazo[4,5-c]quinolin-1-yl-cyclohexanol (cis-compound)[1,2] | 268 | 9.19[4] | 273-274 |
| 11 | 1-n-Butyl-1H-imidazo[4,5-c]quinoline | 226 | 6.40[3] | n.d. |

TABLE 1-continued

| Example | Compound name | M/e$_o$ | t$_{ret}$ | mp [° C.] |
|---|---|---|---|---|
| 12 | 4-Imidazo[4,5-c]quinolin-1-yl-cyclohexanol (cis/trans mixture)[2] | 268 | 8.15[4] | 298-299 |
| 13 | 4-Imidazo[4,5-c]quinolin-1-yl-phenylamine[1] | 261 | 8.25[4] | 310-311 |

[1]The title compounds are obtained by treating a CH$_2$Cl$_2$-solution of the primary reaction product with ca. 0.5 ml of conc. HCl
[2]Isolated as a hydrochloride
[3]Grad 1
[4]Grad 3

Example 14

2-(4-Imidazo[4,5-c]quinolin-1-yl-phenyl)-ethylamine

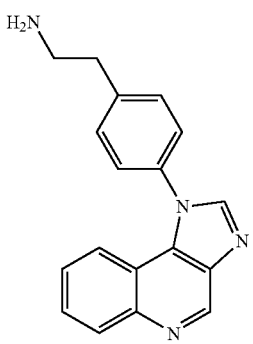

1.3 g (4.6 mmol) of (4-imidazo[4,5-c]quinolin-1-yl-phenyl)-acetonitrile (Example 8) and 0.7 g Raney-Ni in 220 ml 10% NH$_3$ in methanol/THF 1:1 are hydrogenated for 6 h at 45° C. and 1.012 bar. The catalyst is filtered off and washed with methanol. The solvent is partially evaporated and diethyl ether is added. The precipitated material is filtered off and discarded. The mother liquor is concentrated to dryness and the title compound is isolated as colorless crystals. MS: 289 (M$^+$+1); HPLC: t$_{ret}$=7.57 min (Grad 3).

Example 15

7-Chloro-1-(4-fluoro-phenyl)-1H-imidazo[4,5-c]quinoline

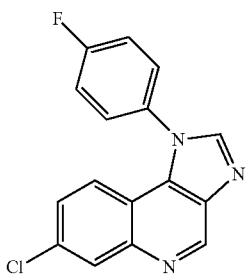

0.72 g (2.5 mmol) 7-chloro-N-4-(4-fluoro-phenyl)-quinoline-3,4-diamine (Example 15d) in 25 ml triethylorthoformate are heated under reflux for 3.5 h. The reaction mixture is cooled with ice-water for 30 min. The crystals which are formed are filtered off, washed with hexane, and dried at 70° C. for 16 hrs under high vacuum. mp: 273-274° C., MS: 298 (M$^+$+1); HPLC: t$_{ret}$=8.46 min (Grad 1).

Example 15a

7-Chloro-3-nitro-quinolin-4-ol

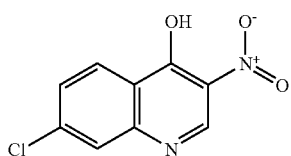

20 g (0.111 mol) 7-chloro-quinolin-4-ol (Aldrich) are added during 5 min to 200 ml nitric acid (66%) heated at 85-90° C. After 4.5 h the title compound starts to precipitate as a crystalline solid. The reaction mixture is stirred for a total of 5.5 h. The hot mixture is filtered off, and the residue washed first with conc. nitric acid, then with boiling water followed by acetone. Additional material can be isolated from the mother liquors. The solid materials are combined and heated in boiling methanol for 3 h to dissolve some un-reacted starting material. The insoluble title compound is filtered off and dried for 16 h at 70° C. (high vacuum). mp: >300° C., MS: 225 (M$^+$+1); HPLC: t$_{ret}$=7.30 min (Grad 1).

Example 15b 4,7-Dichloro-3-nitro-quinoline

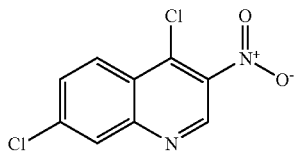

8.5 g 7-chloro-3-nitro-quinolin-4-ol (Example 15a) are heated for 7 h in 80 ml POCl$_3$ under reflux. After standing over night, light yellow needles have formed, which are filtered off and washed with water. The POCl$_3$-filtrate is poured into 1 l of ice-water; additional compound precipitates and is filtered off. The solid materials are dissolved in 300 ml CH$_2$Cl$_2$ and washed first with aqueous sodium hydroxide (300 ml water and 30 ml 2N NaOH), then again with pure water. The organic phase is dried over MgSO$_4$ and evaporated. Colorless needles are formed which are filtered off, washed with hexane, and dried for 16 h at 60° C. (high vacuum). mp: 165-167° C.; MS: 244 (M$^+$+1); HPLC: t$_{ret}$=12.88 min (Grad 1).

Example 15c (7-Chloro-3-nitro-quinolin-4-yl)-(4-fluoro-phenyl)-amine

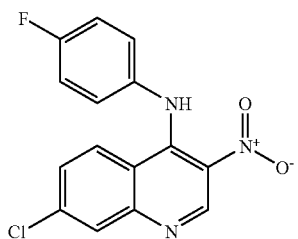

1.3 g (5.3 mmol) 4,7-dichloro-3-nitro-quinoline (Example 15b) and 0.525 g (5.3 mmol) 4-fluoroaniline are stirred at rt for 1 h. The reaction mixture is poured into 150 ml of water, and the resulting crystals are filtered off. After washing with water, the solid is dissolved in ca. 170 ml of ethanol and then concentrated to ca. 30 ml. The solution is cooled in ice-water. The crystals which precipitate are filtered off and dried overnight at 70° C. (high vacuum). mp: 198-200° C.; MS: 318 (M$^+$+1); HPLC: t$_{ret}$=10.92 min (Grad 1).

Example 15d

7-Chloro-N4-(4-fluoro-phenyl)-quinoline-3,4-diamine

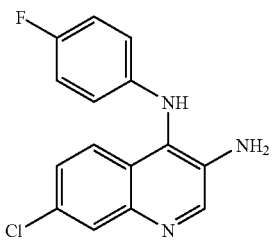

1.3 g (4.09 mmol) (7-chloro-3-nitro-quinolinyl)-(4-fluoro-phenyl)-amine (Example 15c) in 60 ml THF/MeOH 2:1 and 0.6 g Raney-Ni are hydrogenated at rt for 2 h. The reaction solution is filtered on Hyflo® Super Cel diatomaceous earth and is evaporated to dryness. The raw product is dissolved in 30 ml ethyl acetate, and ca. 400 ml hexane are added. The title compound precipitates and is collected by filtration. Drying follows at 65° C. over night. mp: 198-200° C.; MS: 288 (M$^+$+1); HPLC: t$_{ret}$=8.38 min (Grad 1).

In analogy to Example 15, the following 7-chloro-imidazoquinoline derivatives are synthesized:

TABLE 2

| Example | Compound name | M/e$_o$ | t$_{ret}$ | mp [° C.] |
|---|---|---|---|---|
| 16 | 7-Chloro-1-(3-trifluoromethyl-phenyl)-1H-imidazo[4,5-c]quinoline | 348 | 9.70 (Grad 1) | 202-203 |
| 17 | 4-(7-Chloro-imidazo[4,5-c]quinolin-1-yl)-phenol | 296 | 6.79 (Grad 1) | 308-310 |
| 18 | 7-Chloro-1-(3,4-dimethoxy-phenyl)-1H-imidazo[4,5-c]quinoline | 340 | 7.95 (Grad 1) | 226-227 |

Example 19

8-Fluoro-1-(2-fluoro-phenyl)-1H-imidazo[4,5-c]quinoline

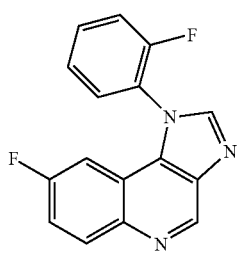

200 mg (0.74 mmol) 6-fluoro-N4-(2-fluoro-phenyl)-quinoline-3,4-diamine (Example 19e) in 8 ml triethylorthoformate are heated at 160° C. for 3 h. The cold solution is evaporated to dryness, and the residue is dissolved in hot ethyl acetate. By adding hexane to this solution, the title compound precipitates. The compound is filtered off and dried overnight at 60° C. (high vacuum). mp: 162-163° C.; MS: 282 (M*+1); HPLC: t$_{ret}$=7.26 min (Grad 1).

Example 19a

5-Fluoro-2-[2-nitro-ethylideneamino]-benzoic acid

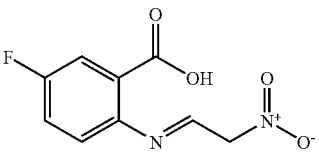

Example 19a and 19b are prepared following procedures reported in J. Med. Chem., 1989, 32, pg 2474 and in references therein. In detail: To 4 g (100 mmol) sodium hydroxide in 8.58 g crushed ice, 3.78 ml (70.9 mmol) of nitromethane are added at 0° C. dropwise and while stirring. After the addition of the nitromethane, the cooling bath is removed and the temperature is allowed to reach rt; stirring is continued for additional 30 min. The violet solution is poured into conc. HCl (11 ml) and crushed ice (11 g), and 5 g (32.3 mmol) 5-fluoro-2-amino benzoic acid (Aldrich) in 277 ml water, and 83 ml conc. HCl are added. After 10 min the solution becomes yellow. Stirring is continued overnight. The yellow precipitate which is formed is filtered off, washed with water and dried. mp: 212° C. The product, 5-fluoro-2-[2-nitro-ethylideneamino]-benzoic acid, is used in the next step without further purification. MS: 225 (M$^+$−1); HPLC: t$_{ret}$=8.56 min (Grad 1).

Example 19b

6-Fluoro-3-nitro-quinolin-4-ol

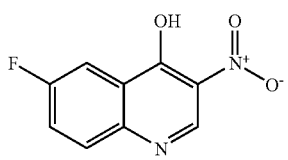

4 g (17.6 mmol) of 5-fluoro-2-[2-nitro-ethylideneamino]-benzoic acid (Example 19a) in 35 ml acetic anhydride are heated (ca. 100° C.) until a clear solution is obtained. 2 g (21.2 mmol) of potassium acetate are added and stirring is continued for 30 min (tlc-control). The reaction mixture is cooled to rt and the formed crystals are filtered off and washed several times with acetic acid and water. mp: 313° C.; MS: 207 (M$^+$−1); HPLC: t$_{ret}$=9.94 min (Grad 3).

Example 19c

4-Chloro-6-fluoro-3-nitro-quinoline

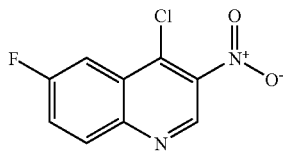

2.3 g (11 mmol) of 6-fluoro-3-nitro-quinolin-4-ol (Example 19b) in 12 ml POCl₃ are heated kept at 130° C. for 4 h. The reaction mixture is cooled to 0° C. and poured into ice-water. A precipitate is formed, which is filtered off and washed with water. The solid material is dissolved in CH₂Cl₂ and washed with 0.1N NaOH and water. After drying the organic phase over MgSO4, the solvent is evaporated to dryness. The residue is dissolved in a few ml of CH₂Cl₂ and hexane is added. The title compound precipitates and is filtered off. Drying is done at 60° C. (high-vacuum) overnight. NMR (DMSO-d6): 9.38/s (1H), 8.32/d×d (1H), 8.18/d×d (1H) and 8.02/d×t (1H); HPLC: $t_{ret}$=11.82 min (Grad 1).

Example 19d (6-Fluoro-3-nitro-quinolin-4-yl)-(2-fluoro-phenyl)-amine

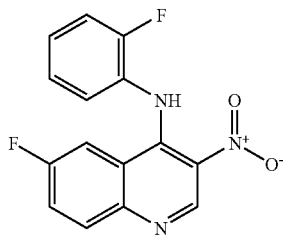

0.4 g (1.8 mmol) of 4-chloro-6-fluoro-3-nitro-quinoline (Example 19c) and 0.17 ml (1.98 mmol) 2-fluoroaniline in 5 ml acetic acid are stirred overnight at rt. Crystals are formed. The mixture is poured into water, the solid material is filtered off and washed with water. The residue is dissolved in CH₂Cl₂ and washed twice with water. The organic phase is dried over MgSO4 and most of the solvent is evaporated. The title compound is obtained from this solution as yellow crystals by adding hexane. The compound is filtered off, washed with hexane and dried (70° C., high-vacuum). mp: 161-162° C.; MS: 302 (M⁺+1); HPLC: $t_{ret}$=10.24 min (Grad 1).

Example 19e

6-Fluoro-N-4-(2-fluoro-phenyl)-quinoline-3,4-diamine

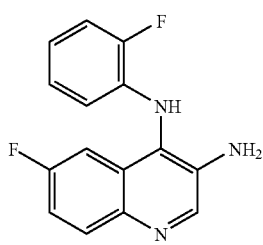

0.38 g (1.3 mmol) (6-fluoro-3-nitro-quinolin-4-yl)-(2-fluoro-phenyl)-amine (Example 19d) in 40 ml methanol-tetrahydrofurane 2:1 and 0.2 g Raney-Ni are hydrogenated during 1 h at rt. After completion of the reaction, the catalyst is filtered off and the solvent is evaporated. The residue is dissolved in CH₂Cl₂, and hexane added. The crystals which separate are collected and dried at 60° C. (high-vacuum). mp: 152-153*C; MS: 272 (M⁺+1); HPLC: $t_{ret}$=7.71 min (Grad 1).

In analogy to Example 19, the following 8-fluoro-imidazoquinoline derivatives are synthesized:

TABLE 3

| Example | Compound name | M/e₀ | $t_{ret}$ | mp [° C.] |
|---|---|---|---|---|
| 20 | 1-(2-Chloro-phenyl)-8-fluoro-1H-imidazo[4,5-c]quinoline | 298 | 7.74 (Grad 1) | 150-151 |
| 21 | 8-Fluoro-1-(2-iodo-phenyl)-1H-imidazo[4,5-c]quinoline | 390 | 8.28 (Grad 1) | 190-191 |
| 22 | [2-(8-Fluoro-imidazo[4,5-c]quinolin-1-yl)-phenyl]-acetonitrile | 303 | 6.83 (Grad 1) | 172-173 |

Example 23

8-Chloro-1-phenyl-1H-imidazo[4,5-c]quinoline

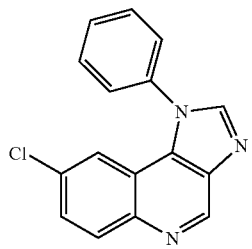

0.3 g (1.11 mmol) of 6-chloro-N-4-phenyl-quinoline-3,4-diamine (Example 23e) in 9 ml triethylorthoformate are heated under reflux for 4.5 h. The solvent is evaporated to 2 ml and hexane is added to the mixture. The desired title compound precipitates and is filtered off. The compound is dried for 16 h at 60° C. (high-vacuum). mp: 240-242° C.; MS: 280 (M⁺+1); HPLC: $t_{ret}$=8.08 min (Grad 1).

Example 23a

5-Chloro-2-[2-nitro-ethylideneamino]-benzoic acid

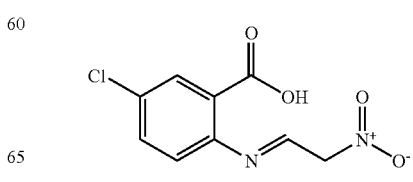

Example 23a and 23b are prepared in analogy to Example 19a and 19b and follow procedures reported in J. Med. Chem., 1989, 32, p 2474 and in references therein. 50 g (0.29 mol) 2-amino-5-chlorobenzoic acid (Fluka) are dissolved in 2.5 l water and 750 ml conc. HCl. Insoluble material is filtered off (solution A). A second solution B is prepared as follows: to 38.5 g (0.96 mol) NaOH and 80 g crushed ice, 34.3 ml (0.638 mol) nitromethane are added slowly (50 min) while cooling with ice-water. During the addition of nitromethane, the temperature is not exceeding 15° C. A colorless emulsion is formed. As the reaction is exothermic, the warm-up of the mixture is carefully monitored and the temperature never exceeds 30° C. When rt is reached, the solution is stirred for additional 30 min. After that time, it is poured slowly to a mixture of 100 ml conc. HCL and 100 g crushed ice (use cooling bath). Solution B and solution A are combined and after 10 min yellow crystals start to precipitate. After standing overnight, the mixture is filtered off and the residue washed with water. The solid is dried at 90° C. over blue-indicating silicagel. mp: 227-229° C. MS: 243 ($M^+$+1); HPLC: $t_{ret}$=9.30 min (Grad 1).

Example 23b

6-Chloro-3-nitro-quinolin-4-ol

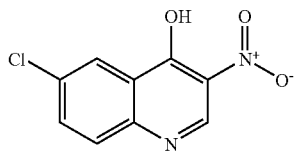

26.5 g (0.109 mol) of 5-chloro-2-[2-nitro-ethylidene-amino]-benzoic acid (Example 23a) in 116 ml acetic anhydride are heated and kept at 110° C. 12.92 g (0.131 mol) potassium acetate are added in 2 min and heating is continued for 40 min at 130-135° C. After 10 min, the title compound starts to crystallize. The reaction vessel is cooled to rt and the solid filtered off and washed with acetic acid and water. Drying follows at 95° C. for 16 h (high vacuum). mp: 341-342° C. (dec.). MS: 225 ($M^+$+1); HPLC: $t_{ret}$=7.33 min (Grad 1).

Example 23c 4,6-Dichloro-3-nitro-quinoline

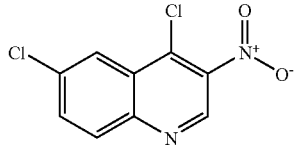

11 g (48.97 mmol) 6-chloro-3-nitro-quinolin-4-ol (Example 23b) in 80 ml POCl$_3$ are heated and kept under reflux for 5 h (tlc-control). The cool reaction mixture is poured slowly into 1.5 l ice-water. The title compound separates as a solid. The mixture is stirred for 15 min. the temperature not exceeding 0-5° C. The solid is filtered off, washed with water and dissolved in 200 ml ethylacetate. The organic phase is washed with a mixture of 200 ml water and 38 ml 2N sodium hydroxide solution and again water. After drying over MgSO$_4$, the solvent is evaporated almost to dryness; to the residue hexane is added and the product is isolated by filtration as a dark-grey powder. This material is used in the next step without further purification. mp: 118-120° C.; NMR (DMSO-d6): 9.43/s (1H); 8.43/d (1H), 8.25/d (1H), 8.10/dxd (1H); HPLC: $t_{ret}$=12.84 min (Grad 1).

Example 23d (6-Chloro-3-nitro-quinolin-4-yl)-phenyl-amine

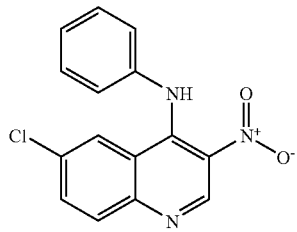

0.6 g (2.46 mmol) 4,6-dichloro-3-nitro-quinoline (Example 23c) and 0.247 ml (2.71 mmol) aniline in 4 ml acetic acid are stirred at rt for 4 h (tlc-control). A precipitate is formed. The reaction mixture is poured into 150 ml water. The solid is filtered off and washed with water and hexane. The filtrate is dissolved in ca. 50 ml diethylether, filtered from insoluble material, and the solvent is evaporated. The residue, yellow crystals, is dried at 60° C. over night. mp: 174-175° C. MS: 300 ($M^+$+1); HPLC: $t_{ret}$=10.53 min (Grad 1).

Example 23e

6-Chloro-N-4-phenyl-quinoline-3,4-damine

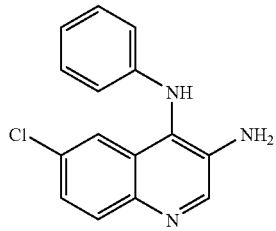

530 mg (1.7 mmol) of (6-chloro-3-nitro-quinolin-4-yl)-phenyl-amine (Example 23d) in 50 ml methanol and 0.3 g Raney-Ni are hydrogenated at rt for 30 min. The reaction solution is filtered on Hyflo® Super Cel diatomaceous earth and is evaporated to dryness. The residue is solved in 15 ml acetone and hexane is added. The title compound separates as a crystalline solid and is filtered off and dried at 60° C. overnight (high vacuum). mp: 198-199° C. MS: 270 ($M^+$+1); HPLC: $t_{ret}$=8.25 min (Grad 1).

In analogy to Example 23, the following 8-chloro-imidazoquinoline derivatives are synthesized:

TABLE 4

| Example | Compound name | M/e$_o$ (M$^+$ + 1) | t$_{ret}$ | mp [° C.] |
|---|---|---|---|---|
| 24 | 8-Chloro-1-o-tolyl-1H-imidazo[4,5-c]quinoline | 294 | 8.80 (Grad 1) | 170-171 |
| 25 | 8-Chloro-1-(2-chloro-phenyl)-1H-imidazo[4,5-c]quinoline | 314 | 9.09 (Grad 1) | 187-188 |
| 26 | 1-(2-Bromo-phenyl)-8-chloro-1H-imidazo[4,5-c]quinoline | 358 (M$^+$) | 8.91 (Grad 1) | 194-195 |
| 27 | 8-Chloro-1-(2-iodo-phenyl)-1H-imidazo[4,5-c]quinoline | 406 | 9.20 (Grad 1) | 190-192 |
| 28 | 2-(8-Chloro-imidazo[4,5-c]quinolin-1-yl)-benzonitrile | 305 | 7.59 (Grad 1) | 193-195 |
| 29 | 8-Chloro-1-(2-methoxy-phenyl)-1H-imidazo[4,5-c]quinoline | 310 | 8.22 (Grad 1) | 152-154 |
| 30 | 8-Chloro-1-(2-ethyl-phenyl)-1H-imidazo[4,5-c]quinoline | 308 | 9.54 (Grad 1) | 108-109 |
| 31[1] | [2-(8-Chloro-imidazo[4,5-c]quinolin-1-yl)-phenyl]-acetonitrile | 319 | 7.62 (Grad 1) | 176-178 |
| 32 | [3-(8-Chloro-imidazo[4,5-c]quinolin-1-yl)-2-methyl-phenyl]-methanol | 324 | 6.49 (Grad 1) | 243-245 |
| 33 | 8-Chloro-1-((S)-1-phenyl-ethyl)-1H-imidazo[4,5-c]quinoline | 308 | 8.62 (Grad 1) | 187-188 |
| 34 | 8-Chloro-1-((R)-1-phenyl-ethyl)-1H-imidazo[4,5-c]quinoline | 308 | 8.73 (Grad 1) | 187-188 |
| 35 | 3-(8-Chloro-imidazo[4,5-c]quinolin-1-yl)-benzonitrile | 305 | 7.80 (Grad 1) | 247-248 |
| 36 | 3-(8-Chloro-imidazo[4,5-c]quinolin-1-yl)-phenylamine | 295 | 6.33 (Grad 1) | 264-265 |
| 37[1] | 2-[4-(8-Chloro-imidazo[4,5-c]quinolin-1-yl)-phenyl]-ethanol | 324 | 6.43 (Grad 1) | 194-195 |
| 38[1] | [4-(8-Chloro-imidazo[4,5-c]quinolin-1-yl)-phenyl]-methanol | 310 | 6.05 (Grad 1) | 239-240 |
| 39 | [4-(8-Chloro-imidazo[4,5-c]quinolin-1-yl)-phenyl]-acetonitrile | 319 | 7.36 (Grad 1) | 224-226 |
| 40[1] | [3-(8-Chloro-imidazo[4,5-c]quinolin-1-yl)-phenyl]-methanol | 310 | 6.26 (Grad 1) | 205-506 |
| 41 | 8-Chloro-1-(2-fluoro-phenyl)-1H-imidazo[4,5-c]quinoline | 298 | 8.09 (Grad 1) | 176-177 |

[1]As a side reaction of the formation of all compounds bearing a hydroxy function, the formation of a certain amount of orthoester on the hydroxy group can be observed. By treating the raw material with a few drops of conc. HCl in CH$_2$Cl$_2$ at rt, the desired title compounds can be obtained.

Example 42

3-(8-Chloro-imidazo[4,5-c]quinolin-1-yl)-benzylamine

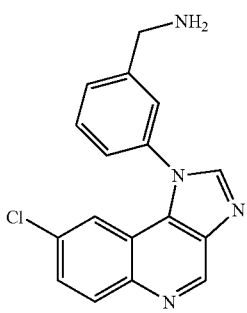

300 mg (0.98 mmol) of 3-(8-chloro-imidazo[4,5-c]quinolin-1-yl)-benzonitrile (Example 35) in 20 ml methanol/NH$_3$ 10% and 250 mg Raney-Ni are hydrogenated at rt for 5 h. The reaction solution is filtered on Hyflo® Super Cel diatomaceous earth and is evaporated to dryness. The title compound is crystallized from ethyl acetate-hexane to yield a grey powder. Drying is done for 16 h at 60° C. (high-vacuum). mp: 148-149° C.; MS: 309 (M$^+$+1); HPLC: t$_{ret}$=8.87 min (Grad 3).

Example 43

2-[4-(8-Chloro-imidazo[4,5-c]quinolin-1-yl)-phenyl]-ethylamine

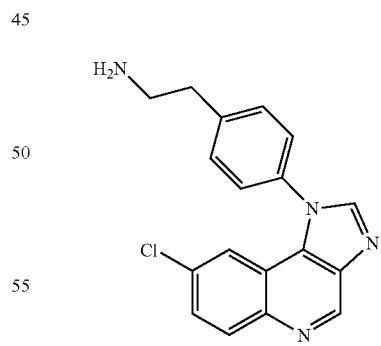

In analogy to Example 42, the title compound is prepared from 400 mg (1.25 mmol) [4-(8-chloro-imidazo[4,5-c]quinolin-1-yl)phenyl]-acetonitrile (Example 39) in 65 ml methanol/HN$_3$ aqu. 10% and 250 mg Raney-Ni. mp: 140-141° C.; MS: 323 (M$^+$+1); HPLC: t$_{ret}$=8.98 min (Grad 3).

Example 44

1-(2-Chloro-phenyl)-8-methoxy-1H-imidazo[4,5-c]quinoline

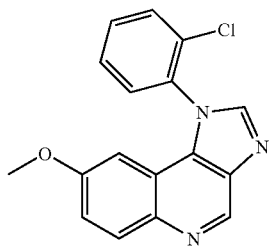

0.2 g (0.66 mmol) of N4-(2-chloro-phenyl)-6-methoxy-quinoline-3,4-diamine (Example 44i) in 6 ml triethylorthoformate are heated under reflux for 4 h. The solvent is evaporated almost to dryness, the dark residue is dissolved in ca. 1 ml ethyl acetate and the compound is precipitated by adding ca. 30 ml of hexane. The desired title compound is filtered off, and is dried for 16 h at 60° C. (high-vacuum). mp: 202-205° C.; MS: 310 ($M^+$+1); HPLC: $t_{ret}$=70.56 min (Grad 1).

Example 44a

5-Hydroxy-2-nitro-benzoic acid 124.6 g (0.618 mol) of 5-chloro-2-nitro-benzoic acid (Fluka Buchs, Switzerland) are heated under reflux in an aqueous sodium hydroxide solution [197.8 g (4.94 mol) of NaOH in 1.23 l water] for 18 h. The cold reaction mixture is extracted several times with ether-ethyl acetate, washed with brine and dried over sodium sulfate. The raw material is crystallized from isopropyl ether-hexane. The crystals are filtered off and dried at 50° C. (high-vacuum). mp: 167-171° C.; MS: 182 ($M^+$−1); HPLC: W-=6.315 min (Grad 1).

Example 44b

5-Methoxy-2-nitro-benzoic acid methyl ester 20 g (0.109 mol) of 5-hydroxy-2-nitro-benzoic acid (Example 44a) and 32.7 g (0.247 mol) potassium carbonate are stirred for 15 min in 163 ml of DMF. 23.8 ml (0.383 mol) of methyl iodide are added and the reaction mixture is stirred for 4 h at 75° C. The cold reaction mixture is diluted with water and is extracted with ether. After drying the organic phase with sodium sulfate, the solvent is evaporated to dryness. The residue, a yellow oil, is used in the next step without further purification. HPLC: $t_{ret}$=1.07 min (Grad 1); NMR (DMSO-d6): 8.15/d (1H), 7.29/s (1H), 7.26/dxd (1H), 3.92/s (3H) and 3.85/s (3H).

Example 44c

5-Methoxy-2-nitro-benzoic acid

The crude material from Example 44b (23.3 g) is dissolved in 110 ml ethanol and 44 ml of 4N NaOH. The mixture is stirred at rt for 18 h. After that time, the ethanol is evaporated. To the residue, water is added and the mixture is washed twice with dichloromethane. To the water phase, conc. HCl is added until pH=1 is reached. The title compound is obtained by extraction with ether. Purification follows by crystallization from ethyl acetate-hexane. mp: 131-134° C.; MS: 196 ($M^+$−1); HPLC: $t_{ret}$=7.90 min (Grad 1).

Example 44d

2-Amino-5-methoxy-benzoic acid 17 g (86 mmol) of 5-methoxy-2-nitro-benzoic acid (Example 44c) in 170 ml ethanol are hydrogenated (1.013 bar) over 0.85 g Pd—C 10% for 8 h at ambient temperature. The catalyst is filtered off and ca. 50 ml 1N HCl are added. By evaporating the solvent, crystals start to precipitate. Crystallization is done from ethanol-diethyl ether. The compound is collected by filtration and dried at 50° C. (high vacuum). mp: 143-148° C.; MS: 166 ($M^+$−1); HPLC: $t_{ret}$=7.42 min (Grad 3).

Example 44e

5-Methoxy-2-[2-nitro-ethylideneamino]-benzoic acid

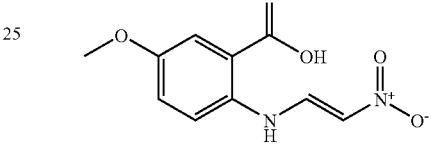

The synthesis of the title compound is done in analogy to Example 19a: 2-Amino-5-methoxy-benzoic acid (8.8 g; 52.6 mmol; Example 44d) is dissolved in 700 ml water and 135 ml conc. HCl (solution A). A second solution B is prepared by adding 6.4 ml (0.115 mol) of nitromethane to 6.95 g (0.173 mol) NaOH dissolved in 15 g ice (ice-water cooling, T≦15° C.). The ice bath is removed, stirring is continued for 1 h. The reaction is exothermic, additional cooling may be necessary (T≦30° C.). This solution B is then poured into 18.5 ml conc. HCl in 19 g ice, giving solution C. Solution A and C are combined. After 10 min, yellow crystals start to separate. Stirring is continued for ca. 2¾ h, the last 30 min by cooling with ice-water. The crystals are filtered off, washed with water and hexane, and dried at 85° C. for 16 h (high vacuum). mp: 194-196° C.; MS: 239 ($M^+$+1); HPLC: $t_{ret}$=8.37 min (Grad 1).

Example 44f

6-Methoxy-3-nitro-quinolin-4-ol

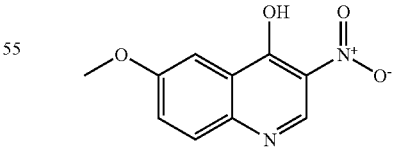

The title compound is prepared in analogy to Example 19b starting from 7.15 g (0.029 mol) of 5-methoxy-2-[2-nitro-ethylidenamino]-benzoic acid (Example 44e), 32 ml acetic anhydride, and 3.52 g (0.035 mol) potassium acetate. The title compound which precipitates from the solution, is filtered off, washed with acetic acid, and dried overnight at 85° C. mp: 278-281° C.; MS: 221 ($M^+$+1); HPLC: $t_{ret}$=10.23 min (Grad 1).

Example 44g

4-Chloro-6-methoxy-3-nitro-quinoline

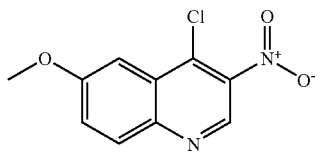

The title compound is prepared in analogy to Example 19c starting from 3.5 g (15.89 mmol) 6-methoxy-3-nitro-quinolin-4-ol (Example 44f) and 24 ml POCl$_3$. mp: 281-283° C.; MS: 239 (M$^+$+1); HPLC: t-=12.29 min (Grad 1).

Example 44h

(2-Chloro-phenyl)-(6-methoxy-3-nitro-quinolin-4-yl)-amine

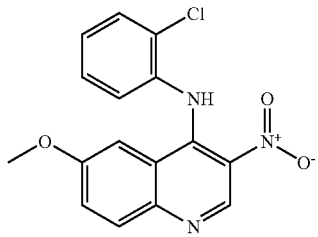

The title compound is obtained in analogy to Example 19d starting from 0.7 g (2.93 mmol) 4-chloro-6-methoxy-3-nitro-quinoline (Example 44g), 0.34 ml (3.23 mmol) 2-chloroaniline and 3 ml acetic acid. mp: 163-165° C.; MS: 330 (M$^+$+1); HPLC: t$_{ret}$=9.73 min (Grad 1).

Example 44i

N4-(2-Chloro-phenyl)-6-methoxy-quinoline-3,4-diamine

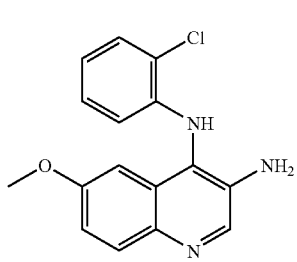

The title compound is prepared in analogy to Example 19e, starting from 0.8 g (2.4 mmol) of (2-chloro-phenyl)-(6-methoxy-3-nitro-quinolin-4-yl)-amine (Example 44h) and 0.4 g Raney-Ni in 30 ml methanol. Time of hydrogenation: 1 h at rt. Crystallization of the product from ethyl acetate-hexane. mp: 120-123° C.; MS: 300 (M$^+$+1); HPLC: t$_{ret}$=8.41 min (Grad 1).

In analogy to Example 44 and starting from the common intermediate 4-chloro-6-methoxy-3 nitro-quinoline (Example 44g), the following compounds are synthesized:

TABLE 5

| Example | Compound name | M/e$_o$ (M$^+$+1) | t$_{ret}$ | mp [° C.] |
|---|---|---|---|---|
| 45 | 1-(2-Fluoro-phenyl)-8-methoxy-1H-imidazo[4,5-c]quinoline | 294 | 7.17 (Grad 1) | 180-182 |
| 46 | 8-Methoxy-1-o-tolyl-1H-imidazo[4,5-c]quinoline | 290 | 7.69 (Grad 1) | 179-180 |
| 47 | 3-(8-Methoxy-imidazo[4,5-c]quinolin-1-yl)-phenylamine[1)2)] | 291 | 5.87 (Grad 1) | 222-223 |

[1)]prepared from 44 g) and 3-nitro-aniline.
[2)]As a side reaction in the formation of all compounds bearing an amino function, the formation of a certain amount of enolether on the amino group can be observed. By treating the raw material with a few drops of conc. HCl in CH$_2$Cl$_2$ at rt, the desired title compounds are obtained.

Example 48

8-Methoxy-1-phenyl-1H-imidazo[4,5-]quinoline

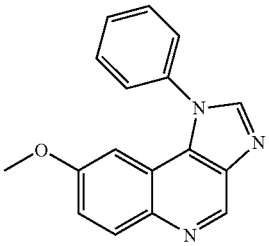

The title compound is obtained by hydrogenation of 1-(2-chloro-phenyl)-8-methoxy-1H-imidazo[4,5-c]quinoline (Example 44) in MeOH/DMF (2:1, v/v) and Pd—C 10%. MS: 276.1; HPLC: t$_r$=5.22 min.

Example 49

1-(2-Chloro-phenyl)-ethyl-1H-imidazo[4,5-c]quinoline

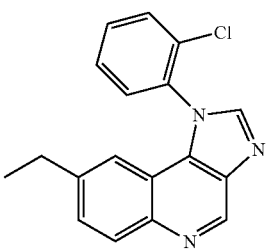

The title compound is prepared in analogy to Example 19, starting from 200 mg (0.671 mol) of N-4-(2-chloro-phenyl)-6-ethyl-quinoline-3,4-diamine (Example 49g) and 6 ml triethylorthoformate. mp: 156-158° C.; MS: 308 (M⁺+1); HPLC: $t_{ret}$=8.51 min (Grad 1).

Example 49a

5-Ethyl-1H-indole-2,3-dione

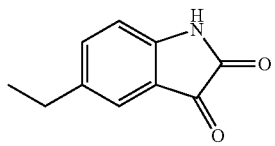

The title compound is prepared starting from 30 g (0.248 mol) of p-ethylaniline (Fluka, Buchs, Switzerland), 54 g (0.326 mol) chloral hydrate, and 750 g sodium sulfate in 800 ml water followed by the addition of 60 g (0.863 mol) NH₂OH—HCl in water. By treating the intermediate with conc. H₂SO₄, the final product is obtained. (For the procedure, see Ng. Ph. Buu-Hoi et. al. in J. Chem. Soc., 4867 (1952)). The crude compound is used in the next step without further purification. Only a small sample is crystallized from methanol for analytical purposes. mp: 135-137° C. (Lit.: 135° C.); MS: 174 (M⁺⁻+1); HPLC: $t_{ret}$=8.74 min (Grad 1).

Example 49b

2-Amino-5-ethyl-benzoic acid

The title compound is prepared by treating 24.7 g (0.141 mol) 5-ethyl-1H-indole-2,3-dione (Example 49a) with 40 ml of 30% H₂O₂ in 226 ml 5% sodium hydroxide solution following a procedure given by A. Baruffini et. al. in *Il Farmaco, Ed. Sc.*, 23, 3 (1968). mp: 128-129° C. (Lit.: 126° C.); MS: 166 (M⁺+1); HPLC: $t_{ret}$=7.00 min (Grad 1).

Example 49c

5-Ethyl-2-((E)-2-nitro-vinylamino)-benzoic acid

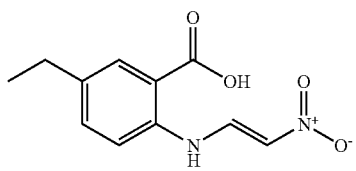

The title compound is prepared in analogy to Example 19a starting from 9.7 g (58.71 mmol) 2-amino-5-ethyl-benzoic acid (Example 49b) and 7.12 ml nitromethane. mp: 190-191° C.; MS: 237 (M⁺+1); HPLC: $t_{ret}$=9.90 min (Grad 1).

Example 49d

6-Ethyl-3-nitro-quinolin-4-ol

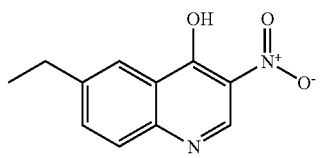

The title compound is prepared in analogy to Example 19b starting from 11.2 g (47.4 mmol) of 5-ethyl-2-((E)-2-nitro-vinylamino)benzoic acid (Example 49c) and 5.58 g (56.8 mmol) potassium acetate in 50 ml acetic anhydride. mp: 308-310° C. (dec.); MS: 219 (M⁺+1); HPLC: $t_{ret}$=12.48 min (Grad 3).

Example 49e

4-Chloro-6-ethyl-3-nitro-quinoline

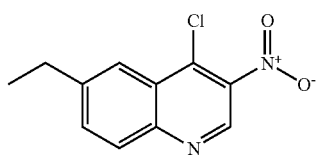

The title compound is prepared in analogy to Example 19c starting from 3.6 g (16.49 mmol) 6-ethyl-3-nitro-quinolin-4-ol (Example 49d) and 24 ml POCl₃. mp: 290-295° C.; MS: 237 (M⁺+1); HPLC: $t_{ret}$=13.72 min (Grad 1).

Example 49f (2-Chloro-phenyl)-(6-ethyl-3-nitro-quinolin-4-yl)-amine

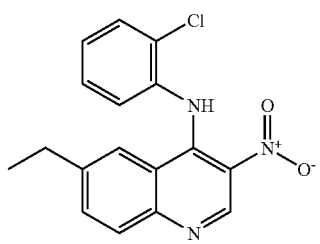

The title compound is prepared in analogy to Example 19d starting from 0.7 g (2.957 mmol) of 4-chloro-6-ethyl-3-nitro-quinoline (Example 49e) and 0.37 g (3.55 mmol) 2-chloroaniline in 3 ml acetic acid. Crystallization from ethyl acetate-hexane. mp: 134-136° C.; MS: 328 (M⁺+1); HPLC: $t_{ret}$=10.61 min (Grad 1).

Example 49g

N-4-(2-Chloro-phenyl)-6-ethyl-quinoline-3,4-di-amine

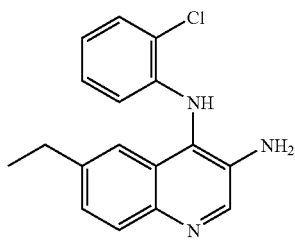

The title compound is prepared by hydrogenation in analogy to Example 19e starting from 720 mg (2.4 mmol) of (2-chloro-phenyl)-(6-ethyl-3-nitro-quinolin-4-yl)-amine (Example 49o and 4000 mg Raney-Ni in 30 ml methanol. mp: 105-108° C.; MS: 298 (M$^+$+1); HPLC: t$_{ret}$=9.34 min (Grad 1).

In analogy to Example 49 and starting from the common intermediate 4-chloro-6-ethyl-3 nitro-quinoline (Example 49e), the following compounds are synthesized:

TABLE 6

| Example | Compound name | M/e$_o$ (M$^+$+ 1) | t$_{ret}$ | mp [° C.] |
|---|---|---|---|---|
| 50 | 8-Ethyl-1-(2-fluoro-phenyl)-1H-imidazo[4,5-c]quinoline | 292 | 8.01 (Grad 1) | 151-152 |
| 51 | 8-Ethyl-1-o-tolyl-1H-imidazo[4,5-c]quinoline | 288 | 8.62 (Grad 1) | 136-137 |
| 52 | 3-(8-Ethyl-imidazo[4,5-c]quinolin-1-yl)-phenylamine[1)] | 289 | 6.71 (Grad 1) | 225-227 |

[1)] see footnote 1 and 2 in Table 5.

Example 53

1-(2-Bromo-phenyl)-8-Phenyl-1H-imidazo[4,5-c]quinoline

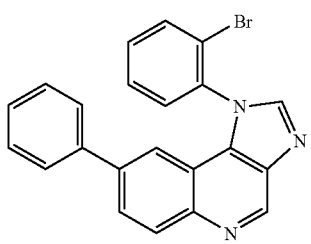

The title compound and the compounds in the following Table 7 are prepared in analogy to Example 19 by boiling the respective quinoline 3,4-diamine derivatives (e.g. Example 53f) in triethylorthoformate. The reaction is controlled by tlc. The purification of the products is achieved by direct crystallization of the raw material after having evaporated the solvent, or by chromatography on silica gel, followed by crystallization. mp: 128-129° C.; MS: 400 (M$^+$+1); HPLC: t$_{ret}$=9.76 min (Grad 1).

Example 53a

4-Amino-biphenyl-3-carboxylic acid

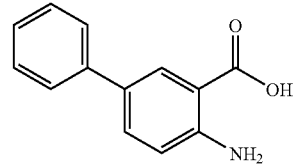

1 g (4.62 mmol) of 5-bromoanthranilic acid (Fluka Buchs, Switzerland) and 6.94 ml 1M K$_2$CO$_3$ are stirred in 10 ml DMF. Argon gas is bubbled through the solution. 50 mg tetrakis-triphenylphosphin-palladium (Fluka) and 846 mg (6.94 mmol) phenylboronic acid (Fluka, Buchs, Switzerland) are added. The reaction mixture is stirred for 15 h at 80° C. (tlc-control). The solvent is evaporated, and 50 ml 4N NaOH are added to the residue. The aqueous phase is washed three times with ethyl acetate. Hydrochloric acid is added to the water phase until pH=7 is reached and the aqueous phase is extracted four times with ethyl acetate. After drying the organic phase with MgSO$_4$, the solvent is evaporated and the residue crystallized from CH$_2$Cl$_2$-methanol-hexane. mp: 245° C. (dec.); MS: 214 (M$^+$+1); HPLC: t$_{ret}$=9.74 min (Grad 1).

Example 53b 4-((E)-2-Nitro-vinylamino)-biphenyl-3-carboxylic acid

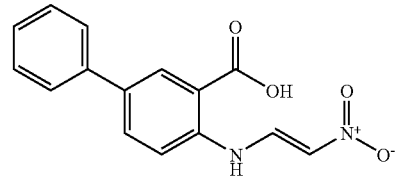

The title compound is prepared in analogy to Example 19a, starting from 5 g (22.6 mmol) of 4-amino-biphenyl-3-carboxylic acid (Example 53a), 2.73 ml (49.72 mmol) nitromethane, and 3.01 g (74.59 mmol) NaOH. The title compound precipitates from the reaction mixture and is filtered off. The raw material is used in the next step without further purification. mp: 150° C. (dec.); MS: 285 (M$^+$+1); HPLC: t$_{ret}$=10.97 min (Grad 1).

Example 53c

3-Nitro-6-phenyl-quinolin-4-ol

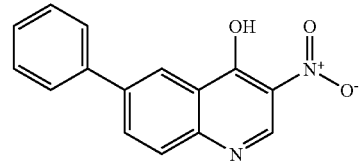

The title compound is prepared in analogy to Example 19b, starting from 1 g (3.518 mmol) of 4-((E)-2-nitro-vinylamino)-biphenyl-3-carboxylic acid (Example 53b), 0.418 g (4.25 mmol) potassium acetate, and 7.8 ml acetic anhydride. mp: 298° C. (dec.); MS: 265 (M$^+$−1); HPLC: t$_{ret}$=8.97 min (Grad 1).

Example 53d

4-Chloro-3-nitro-6-phenyl-quinoline

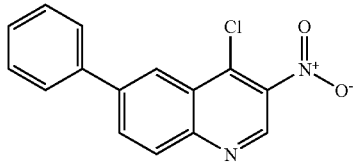

The title compound is prepared in analogy to Example 19e, starting from 900 mg (3.38 mmol) 3-nitro-6-phenyl-quinolin-4-ol (Example 53c) in 10 ml POCl$_3$. The compound is crystallized from ethylacetate-hexane. mp: 144-145° C.; MS: 284 (M$^+$+1); HPLC: t$_{ret}$=140.51 min (Grad 1).

Example 53e

(2-Bromo-phenyl)-(3-nitro-6-phenyl-quinolin-4-yl)-amine

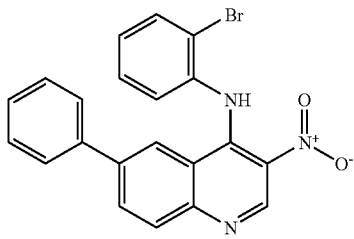

The title compound is prepared in analogy to Example 19d, starting from 0.5 g (1.756 mmol) 4-chloro-3-nitro-6-phenyl-quinoline (Example 53d) and 0.339 g (1.932 mmol) 2-bromoaniline in 3 ml acetic acid. mp: 198-204° C.; MS: 420 (M$^+$+1); HPLC: t$_{ret}$=12.17 min (Grad 1).

Example 53f

N4-(2-Bromo-phenyl)-6-phenyl-quinoline-3,4-diamine

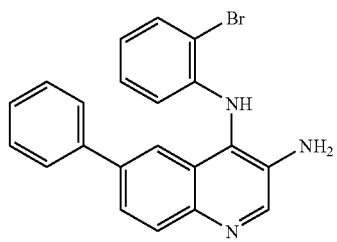

The title compound is prepared in analogy to Example 19e by hydrogenation at 0° C. for 86 min starting from 0.697 g (1.502 mmol) of (2-bromo-phenyl)-(3-nitro-6-phenyl-quinolin-4-yl)-amine (Example 53e) and 0.25 g Raney-Ni in 25 ml methanol-THF 2:1. Purification follows by chromatography on silica gel (ethyl acetate-hexane 1:1). mp: 174-177° C.; MS: 390 (M$^+$+1); HPLC: t$_{ret}$=10.50 min (Grad 1).

In analogy to Example 53 and starting from the common intermediate 4-chloro-3-nitro-6 phenyl-quinoline (Example 53d), the following compounds are synthesized:

TABLE 7

| Example | Compound name | M/e$_o$ | t$_{ret}$[min] | mp [° C.] |
|---|---|---|---|---|
| 54 | 1-(2-Fluoro-phenyl)-8-phenyl-1H-imidazo[4,5-c]quinoline | 340(M$^+$+ 1) | 9.48 (Grad 1) | 139 |
| 55 | 1-(2-Methoxy-phenyl)-8-phenyl-1H-imidazo[4,5-c]quinoline | 352(M$^+$+ 1) | 9.49 (Grad 1) | 115-116 |
| 56 | 8-Phenyl-1-(3-trifluoromethyl-phenyl)-1H-imidazo[4,5-c]quinoline | 390(M$^+$+ 1) | 10.32 (Grad 1) | 181-184 |
| 57 | 8-Phenyl-1-o-tolyl-1H-imidazo[4,5-c]quinoline | 336(M$^+$+ 1) | 9.92 (Grad 1) | 149-150 |
| 58 | 3-(8-Phenyl-imidazo[4,5-c]quinolin-1-yl)-phenylamine[1] | 337(M$^+$+ 1) | 8.44 (Grad 1) | 210-220 |
| 59 | 1-(2-Ethyl-phenyl)-8-phenyl-1H-imidazo[4,5-c]quinoline | 350(M$^+$+ 1) | 10.47 (Grad 1) | 114-115 |
| 60 | 1,8-Diphenyl-1H-imidazo[4,5-c]quinoline | 322(M$^+$+ 1) | 9.64 (Grad 1) | 215 |
| 61 | 1-(2-Chloro-4-methyl-phenyl)-8-phenyl-1H-imidazo[4,5-c]quinoline | 370(M$^+$+ 1) | 10.70 (Grad 1) | 184 |
| 62 | [3-(8-Phenyl-imidazo[4,5-c]quinolin-1-yl)-phenyl]-methanol | 352(M$^+$+ 1) | 7.90 (Grad 1) | 237 |
| 63 | 2-(8-Phenyl-imidazo[4,5-c]quinolin-1-yl)-benzonitrile | 347(M$^+$+ 1) | 8.78 (Grad 1) | 190-192 |
| 64 | [2-(8-Phenyl-imidazo[4,5-c]quinolin-1-yl)-phenyl]-acetonitrile | 359(M$^+$− 1) | 8.97 (Grad 1) | 165-166 |

[1]prepared from 53d and 3-nitroaniline

Example 65

2-(8-Phenyl-imidazo[4,5-c]quinolin-1-yl)-benzylamine

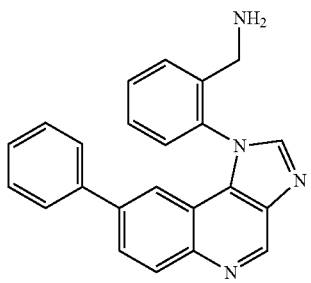

To 100 mg of (0.288 mmol) 2-(8-phenyl-imidazo[4,5-c]quinolin-1-yl)-benzonitrile (Example 63) in 2 ml THF and 6 ml 10% ammonia in methanol are added ca. 50 mg Raney-Ni in ethanol. The solution is hydrogenated at rt for 6 h. The catalyst is filtered off and the raw material is purified by chromatography on silica gel (CH$_2$Cl$_2$-methanol 9:1) and crystallization (ethyl-acetate-hexane). mp: 163-1650° C.; MS: 351 (M$^+$+1); HPLC: t$_{ret}$=6.42 min (Grad 1).

Example 66

2-[2-(8-Phenyl-imidazo[4,5-c]quinolin-1-yl)-phenyl]-ethylamine

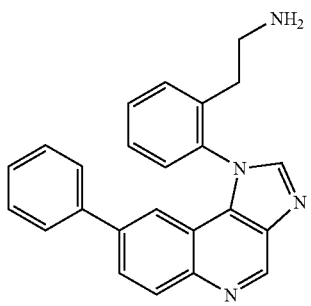

The title compound is prepared in analogy to Example 65, starting from 100 mg [2-(8-phenyl-imidazo[4,5-c]quinolin-1-yl)-phenyl]-acetonitrile (Example 64). The title compound is an amorphous powder. MS: 365 (M$^+$+1); HPLC: t$_{ret}$=6.690 min (Grad 1).

Example 67

N-Hydroxy-2-(8-phenyl-imidazo[4,5-c]quinolin-1-yl)-benzamidine

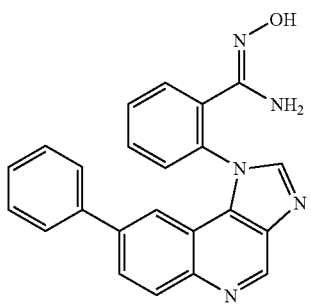

To 300 mg (0.832 mmol) of 2-(8-phenyl-imidazo[4,5-c]quinolin-1-yl)-benzonitrile (Example 63) and 360 mg (5.19 mmol) hydroxylamine hydrochloride in 7 ml DMF, a solution of 490 mg (4.61 mmol) sodium carbonate in 2.6 ml water is added using a syringe within 3 min. After a few minutes, a precipitate starts to appear. Stirring is continued for 4 h at 70° C. (tlc-control). The reaction mixture is cooled to 0° C. and is poured into 100 ml ice-water. The compound is filtered off, washed with water and hexane, and dried at 65° C. for 16 h (high-vacuum). mp: 249-251° C. MS: 380 (M+1); HPLC: t$_{ret}$=6.91 min (Grad 1).

Example 68

N-Hydroxy-2-[2-(8-phenyl-imidazo[4,5-c]quinolin-1-yl)-phenyl]-acetamidine

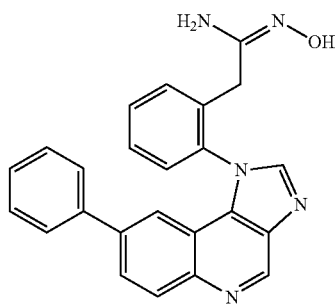

The title compound is prepared in analogy to Example 67 starting from 300 mg (0.832 mmol) of [2-(8-phenyl-imidazo[4,5-c]quinolin-1-yl)phenyl]-acetonitrile (Example 64), 346 mg (0.499 mmol) hydroxylamine hydrochloride in 7 ml DMF, and 465 mg sodium carbonate in 2.5 ml water. The compound is isolated as colorless powder. mp: 253-254° C.; MS: 394 (M+1); HPLC: t$_{ret}$=6.57 min (Grad 1).

Example 69

2-(8-Phenyl-imidazo-4,5-quinolin-1-yl)-benzamidine

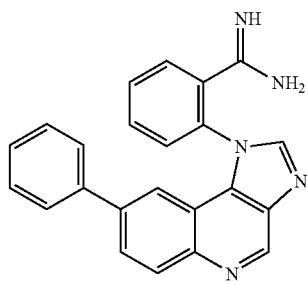

200 mg (0.52 mmol) of N-hydroxy-2-(8-phenyl-imidazo[4,5-c]quinolin-1-yl)benzamidine (Example 67) in 4 ml 0.5N hydrochloric acid and a total of 100 mg Raney-Ni (added in two portions) are hydrogenated at 50° C. for 44 h. The catalyst is filtered off, and the residue is purified by flash-chromatography on silica gel (THF-H$_2$O-1N HCl 90:10:0.25). The compound is crystallized from THF-ethylacetate. mp: 284-285° C.; MS: 364 (M$^+$+1); HPLC: t$_{ret}$=6.18 min (Grad 1).

Example 70

2-[2-(8-Phenyl-imidazo[4,5-c]quinolin-1-yl)-phenyl]-acetamidine

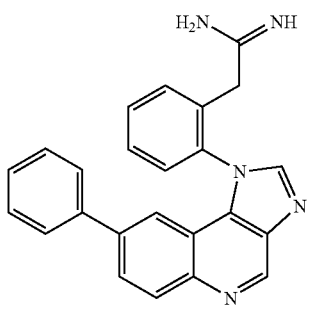

The title compound is prepared in analogy to Example 69 starting from 220 mg (0.559 mmol) N-hydroxy-2-[2-(8-phenyl-imidazo[4,5-c]quinolin-1-yl)-phenyl]-acetamidine (Example 68) and 120 mg Raney-Ni in 6 ml 0.5 N HCl at 50° C. for 9 h. The compound is purified by chromatography (THF-H$_2$O-1N HCl 90:10:0.25) and precipitated from ethyl acetate. mp: 261-263° C.; MS: 378 (M$^+$+1); HPLC: t$_{ret}$=6.66 min (Grad 1).

Example 71

8-Chloro-1-(2-chloro-phenyl)-1H-imidazo[4,5-c] quinoline 5-oxide

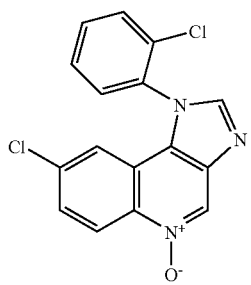

3.01 g (9.508 mmol) 8-chloro-1-(2-chloro-phenyl)-1H-imidazo[4,5-c]quinoline (Example 25), 1.22 g (11.4 mmol) sodium carbonate and 2.6 g (10.45 mmol) 3-chloroperoxybenzoic acid in 75 ml chloroform are stirred at rt for 5 h. After this time, a further amount of 254 mg of sodium carbonate, 472 mg 3-chloroperoxybenzoic acid and 50 ml chloroform are added and stirring is continued for 2 h at 50° C. The cold solution is washed with sat. sodium bicarbonate solution (2×), 0.1 N sodium thiosulfate (2×) and brine (2×). The organic phase is dried over sodium sulfate and the solvent evaporated. Purification of the title compound is achieved by chromatography (CH$_2$Cl$_2$-methanol 95:5→90:10) and crystallization (ethyl acetate-hexane). mp: 247-250° C.; MS: 330 (M$^+$+1); HPLC: t$_{ret}$=11.25 min (Grad 1).

Example 72

N-[8-Chloro-1-(2-chloro-phenyl)-1H-imidazo[4,5-c] quinolin-4-yl]-benzamide

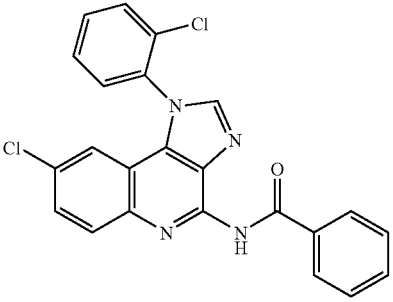

A solution of 0.644 g (3.939 mmol) benzoyl isocyanate in 10 ml CH$_2$Cl$_2$ is added within 10 min to 1 g (3.029 mmol) of 8-chloro-1-(2-chloro-phenyl)-1H-imidazo[4,5-c]quinoline 5-oxide (Example 71) in 10 ml CH$_2$Cl$_2$. The reaction mixture is heated and kept under reflux for 7 h. The solvent is evaporated, and the residue is purified by chromatography (CH$_2$Cl$_2$-methanol 97.5:2.5). The compound is crystallized from ethyl acetate-hexane. mp: 255-258° C.; MS: 433 (M$^+$+1); HPLC: t$_{ret}$=10.91 min (Grad 1).

Example 73

8-Chloro-1-(2-chloro-phenyl)-1H-imidazo[4,5c]-quinolin-4-ylamine

50 µl methanolic NaOCH$_3$-solution 5.4M (Fluka) are added to 1.15 g (2.654 mmol) of N-[8-chloro-1-(2-chloro-phenyl)-1H-imidazo[4,5-c]quinolin-4-yl]-benzamide (Example 72) in 30 ml methanol (dry). The reaction mixture is heated and kept under reflux for 2⅔ h. The solution is cooled to 0-5° C. and ca. 20 ml di-isopropyl ether are added. A crystalline precipitate is formed. Stirring is continued for 1 h. The crystals are filtered off and washed with cold di-isopropyl ether. Additional material is isolated from the mother liquor. Further purification follows by crystallization from methanol-di-isopropyl ether. mp: 262-263° C.; MS: 329 (M$^+$+1); HPLC: t$_{ret}$=8.68 min (Grad 1).

Example 74

8-Chloro-1-(2-chloro-phenyl)-1H-imidazo[4,5-c]quinoline-4-carbonitrile

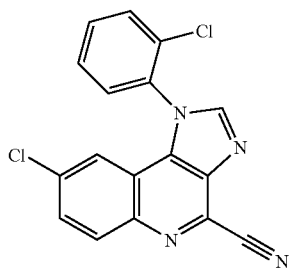

38.1 mg (0.5679 mmol) potassium cyanide and 239 μl (1.704 mmol) triethylamine (dry; Fluka) in 6 ml dry DMF, 182 μl trimethylchlorosilane (Fluka) are added within 10 min to a solution of 100 mg (0.30 mmol) of 8-chloro-1-(2-chloro-phenyl)-1H-imidazo[4,5-c]quinoline 5-oxide (Example 71). The reaction mixture is stirred for 48 h at ca. 100-110° C. bath temperature. The cold solution is filtered, the solvent is evaporated. The residue is purified by chromatography on silica gel ($CH_2Cl_2$-methanol 9:1). The compound can be crystallized from $CH_2Cl_2$-hexane. mp: 248-250° C.; MS: 339 ($M^+$+1); HPLC: $t_{ret}$=13.19 min (Grad 1).

Example 75

4,8-Dichloro-1-(2-chloro-phenyl)-1H-imidazo[4,5-c]quinoline

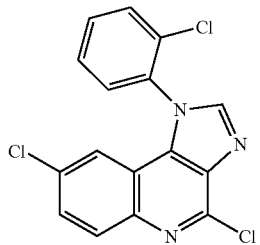

A solution of 100 mg (0.30 mmol) of 8-chloro-1-(2-chloro-phenyl)-1H-imidazo[4,5-c]quinoline 5-oxide (Example 71), 50 μl dry DMF, and 86 μl $POCl_3$ in 2 ml toluene is stirred at 70° C. bath temperature for 3½ h. First, ice is added to the cold reaction mixture, then water and ethyl acetate. The phases are separated and the water phase is extracted with ethyl acetate. The combined organic phases are washed with water and brine, then dried over $Na_2SO_4$. After the solvent is evaporated, the residue is crystallized from ethyl acetate-hexane. mp: 194-200° C.; MS: 348 ($M^+$+1); HPLC: $t_{ret}$=13.54 min (Grad 1).

Example 76

[8-Chloro-1-(2-chloro-phenyl)-1H-imidazo[4,5-c]quinolin-4-yl]-methyl-amine

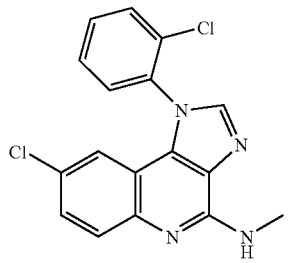

90 mg (0.24 mmol) of 4,8-dichloro-1-(2-chloro-phenyl)-1H-imidazo[4,5-c]quinoline (Example 75) in 2 ml 33% methanolic methylamine-solution (Fluka) are heated in a sealed tube at 120° C. for ca. 4 h. After the solvent is evaporated, the residue is dissolved in hot methanol. A first batch of crystals is obtained after cooling down the methanolic solution. The mother liquor is evaporated and the residue purified by chromatography on silica gel ($CH_2Cl_2$-methanol 97.5:2.5). Additional material is obtained by crystallization from isopropyl alcohol-hexane. mp: 210-212° C.; MS: 343 ($M^+$+1); HPLC: $t_{ret}$=8.88 min (Grad 1).

In analogy to Example 76, and starting from the common intermediate 4,8-dichloro-1-(2-chloro-1H-imidazo[4,5-c]quinoline (Example 75), the following compounds are synthesized (reaction temperature and time see footnotes; the solvent is in all cases 2-ethoxyethanol; temperatures refer to bath temperature):

TABLE 8

| Example | Compound name | $M/e_o$ | $t_{ret}$[min] | mp [° C.] |
|---|---|---|---|---|
| 77 | Butyl-[8-chloro-1-(2-chloro-phenyl)-1H-imidazo[4,5-c]quinolin-4-yl]-amine[1] | 385 ($M^+$+ 1) | 10.72 (Grad 1) | 178-180 |
| 78 | 2-[8-Chloro-1-(2-chloro-phenyl)-1H-imidazo[4,5-c]quinolin-4-ylamino]-ethanol[2] | 373 ($M^+$+ 1) | 8.64 (Grad 1) | 193-195 |
| 79 | [8-Chloro-1-(2-chloro-phenyl)-1H-imidazo[4,5-c]quinolin-4-yl]-phenyl-amine[3] | 405 ($M^+$+ 1) | 10.49 (Grad 1) | 205-206 |
| 80 | [8-Chloro-1-(2-chloro-phenyl)-1H-imidazo[4,5-c]quinolin-4-yl]-cyclopropyl-amine[4] | 369 ($M^+$+ 1) | 9.50 (Grad 1) | 202-206 |
| 81 | 2-[8-Chloro-1-(2-chloro-phenyl)-1H-imidazo[4,5-c]quinolin-4-ylamino]-ethanethiol[5] | 389 ($M^+$+ 1) | 9.74 (Grad 1) | 180-186 |

[1] 20 h at 150° C.
[2] 20 h at 120° C.
[3] 13 h at 120° C., then further 21 h at 150° C.
[4] 12 h at 150° C.
[5] 12 h at 120° C.

Example 82

2-Bromo-8-chloro-1-(2-chloro-phenyl)-1H-imidazo[4,5-c]quinoline

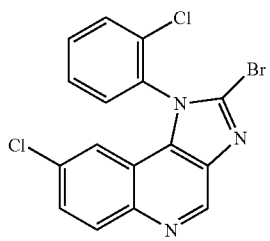

2 g (6.36 mmol) of 8-chloro-1-(2-chloro-phenyl)-1H-imidazo[4,5-c]quinoline (Example 25), 6.6 g (37 mmol) N-bromosuccinimide, and 1.32 g (4.45 mmol) FeBr$_3$ (98%; Aldrich) are heated and kept under reflux during 2½ h in 50 ml CHCl$_3$. The cold solution is poured on ca. 300 ml ice-water, where a precipitate is formed. Extraction of the water phase with CH$_2$Cl$_2$ and chromatography of the raw material on silicagel (hexane-ethyl acetate 1:1) gives the desired title compound. mp: 183-192° C.; MS: 392 (M$^+$+1); HPLC: t$_{ret}$=12.44 min (Grad 1).

Example 83

8-Chloro-1-(2-chloro-phenyl)-1H-imidazo[4,5-c]quinoline-2-carboxylic acid amide

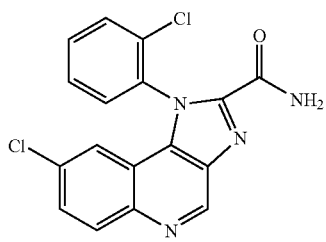

1 g (3.287 mmol) of 6-chloro-N-4-(2-chloro-phenyl)-quinoline-3,4-diamine and 0.6 g (0.73 mmol) oxamic acid in 5 g polyphosphoric acid (83%, Fluka) are heated and kept at 125° C. during 5 h. After cooling, 50 ml 25% ammonia solution is added carefully under stirring to the cold reaction medium. The title compound precipitates partially and is filtered off, washed with water and diethyl ether and dried at 60° C. for 16 h. mp: 194-195° C.; MS: 357 (M$^+$+1); HPLC: t$_{ret}$=8.96 min (Grad 1). Additional material can be obtained from the inorganic phase by extraction with ethyl acetate and purification by chromatography (ethyl acetate-hexane 4:1).

The starting material is prepared as follows:

a) 6-Chloro-N-4-(2-chloro-phenyl)quinoline-3,4-diamine is an intermediate for the synthesis of Example 25 and is prepared in analogy to Example 23e, from 4,6-dichloro-3-nitro-quinoline (Example 23c) and 2-chloroaniline followed by hydrogenation.

Example 84

8-Chloro-1-(2-chloro-phenyl)-1H-imidazo[4,5-c]quinoline-2-carbonitrile

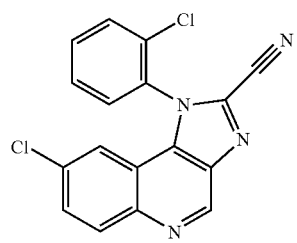

To an ice-cold solution of 546 mg (1.526 mmol) 8-chloro-1-(2-chloro-phenyl)-1H-imidazo-[4,5-c]quinoline-2-carboxylic acid amide (Example 83) dissolved in 18 ml dry pyridine, 1 ml POCl$_3$ is added by syringe during 3 min. The cooling bath is removed, and the reaction mixture heated at 70° C. for 55 min. The solution is cooled to 0° C. and is poured into ice-water and stirred for 15 min. The solid material which has precipitated is filtered off and washed with water and cold ethanol, and dried under high vacuum (16 h at 65° C.). mp: 242-244° C.; MS: 339 (M$^+$+1); HPLC: t$_{ret}$=13.00 min (Grad 1).

In an alternative way, the title compound is prepared from 2-bromo-8-chloro-1-(2-chloro-phenyl)-1H-imidazo[4,5-c]quinoline (50 mg, 0.13 mmol; Example 82), CuCN (68 mg, 0.76 mmol; Fluka, Buchs, Switzerland), tris(dibenzylideneacetone)dipalladium chloroform adduct (Pd$_2$(dba)$_3$.CHCl$_3$; 20 mg, 0.02 mmol; Aldrich), 1,1'-bis(diphenylphosphino)ferrocene (DPPF; 45 mg, 0.08 mmol; Aldrich), and tetraethylammonium cyanide (40 mg, 0.25 mmol; Fluka, Buchs, Switzerland) in 5 ml 1,4-dioxane by heating the reaction mixture for 5 h at 140° C. in a sealed tube.

Example 85

[8-Chloro-1-(2-chloro-phenyl)-1H-imidazo[4,5-c]quinolin-2-yl]-acetonitrile

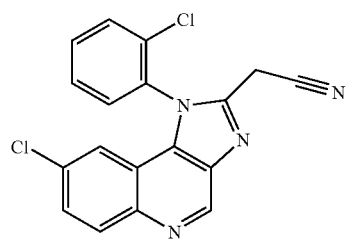

3 g (9.89 mmol) of 6-chloro-N-4-(2-chloro-phenyl)-quinoline-3,4-diamine (Example 83 a)) and 2.6 ml ethyl cyanoacetate (Fluka) are heated at ca. 180° C. for 5 h. Tlc-control indicates an incomplete reaction. 1 ml of ethyl cyanoacetate is added to the reaction mixture and the stirring is continued overnight at 180° C. The cold reaction mixture is purified by chromatography (ethyl acetate-hexane 2:1). MS: 353 (M$^+$+1); HPLC: t$_{ret}$=10.06 min (Grad 1).

Example 86

8-Chloro-1-(2-chloro-phenyl)-N-hydroxy-1H-imidazo[4,5-c]quinoline-2-carboxamidine

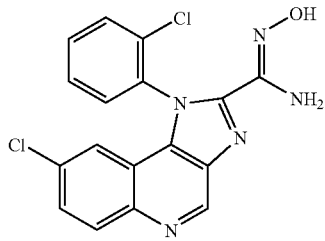

To a mixture of 300 mg of (0.884 mmol) 8-chloro-1-(2-chloro-phenyl)-1H-imidazo[4,5-c]quinoline-2-carbonitrile (Example 84) and 245 mg (3.537 mmol) hydroxylamine hydrochloride in 7.5 ml DMF, a solution of 326 mg (3.08 mmol) sodium carbonate in 1.8 ml water is added by syringe within 2 min. The reaction mixture is heated at 70° C. for 4½ h. The cold solution is poured in ice-water and stirred for 1 h. The precipitate which is formed is filtered off and washed with water and ethanol. The compound is dried over night at 60° C. (high vacuum). mp: 265-267° C.; MS: 372 (M$^+$+1); HPLC: $t_{ret}$=80.43 min (Grad 1).

Example 87

2-[8-Chloro-1-(2-chloro-phenyl)-1H-imidazo[4,5-c]quinolin-2-yl]-N-hydroxy-acetamidine

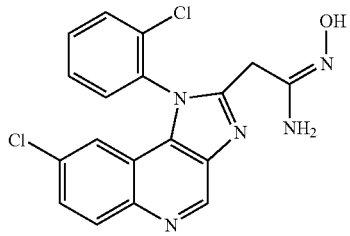

The title compound is prepared in analogy to Example 86, starting from 500 mg (1.415 mmol) of [8-chloro-1-(2-chlorophenyl)-1H-imidazo[4,5-]quinolin-2-yl]-acetonitrile (Example 85), 590 mg (8.5 mmol) hydroxylamin hydrochloride, 495 mg (4.67 mmol) sodium carbonate in 2.8 ml water and 11.5 ml DMF. mp: 114° C.; MS: 386 (M$^+$+1); HPLC: $t_{ret}$=70.40 min (Grad 1).

Example 88

2-[8-Chloro-1-(2-chloro-phenyl)-1H-imidazo[4,5-c]quinolin-2-yl]-acetamidine

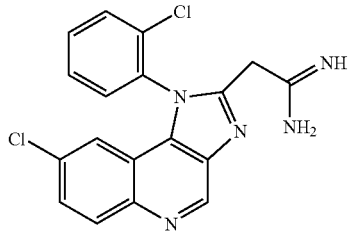

352 mg (0.91 mmol) of 2-[8-chloro-1-(2-chloro-phenyl)-1H-imidazo[4,5-c]quinolin-2-yl]-N-hydroxy-acetamidine (Example 87), 0.91 ml 1N HCl, in 7.1 ml water are hydrogenated at rt (tlc-control) in the presence of ca. 190 mg Raney-Ni. The catalyst is filtered off and washed with methanol. The solvents are evaporated, the residue is dissolved in CH$_2$Cl$_2$-water-methanol. The two phases are separated and evaporated. From the water phase, a yellow oil separates. The oil is dissolved in hot methanol and diethyl ether is added. On stirring at 0-5° C., a solid separates. The solid, which is the title compound, is filtered off and dried for 6 h at 50° C. MS: 370 (M$^+$+1); HPLC: $t_{ret}$=7.38 min (Grad 1).

Example 89

Description of Synthesis of the Compound of Examples 92, 93, 95, 104, 113, 114, 108, 128, 133 and 100, Respectively, Given in the Subsequent Table A) Synthesis of the Compound of Example 92:

8-Chloro-1-(2-chloro-phenyl)-1,3-dihydro-imidazo[4,5-c]quinolin-2-one (Example 92) is synthesized as follows: To a stirred solution of 1.2 g (3.95 mmol) of 6-chloro-N-4-phenyl-quinoline-3,4-diamine (step e) and 0.68 ml (4.85 mmol) of triethylamine in 50 ml of anhydrous dichloromethane at 0° C., dropwise 50 ml of anhydrous dichloromethane containing 0.53 ml (4.42 mmol) of trichloromethylchloroformate (Fluka, Buchs, Switzerland) are added. The solution is stirred for 4 h at room temperature. After this time, the solution is evaporated to dryness and the residue is dissolved in 150 ml of ethyl acetate. The organic phase is washed with 0.1 N HCl and brine, dried with anhydrous Na$_2$SO$_4$ and evaporated to dryness. The crude compound is purified by flash-chromatography (dichloromethane with 2% of methanol) to provide the compound mentioned at the beginning of this paragraph, Example 92. Analytical HPLC: $t_{ret}$=6.34 min (Grad. 2); ES-MS: m/e$_0$=330.0, 332.0.

The starting materials are prepared as follows:

(The compounds of steps a) and b) are prepared in analogy to procedures reported in J. Med. Chem. 32, 2474 (1989), and references cited therein).

Step a)
5-Chloro-2-[2-nitro-ethylideneamino]-benzoic acid 50 g (0.29 mol) of 2-amino-5-chloro-benzoic acid (Fluka, Buchs, Switzerland) are dissolved in 2.5 l of water and 750 ml of conc. HCl. Insoluble material is filtered off (solution A). A second solution (solution B) is prepared as follows: to 38.5 g (0.96 mol) of NaOH and 80 g of crushed ice, 34.3 ml (0.64 mol) of nitromethane are added slowly (50 min) while cooling with ice-water. During the addition of nitromethane, the temperature is not exceeding 15° C. A colorless solution is formed. As the reaction is exothermic, the warm-up of the mixture is carefully monitored and the temperature never exceeds 30° C. When room temperature is reached, the solution is stirred for additional 30 min, and, after that time, it is poured slowly to a mixture of 100 ml of conc. HCl and 100 g of crushed ice (use cooling bath). Solutions A and B are combined and after 10 min, yellow crystals start to separate. After standing overnight, the mixture is filtered off and the residue washed with water. The solid (the title compound) is dried at 90° C. over blue-indicating silica gel. mp: 227-229° C.; ES-MS: m/e$_0$=243.

Step b) 6-Chloro-3-nitro-quinolin-4-ol 26.5 g (0.109 mol) of 5-chloro-2-[2-nitro-ethylidene-amino]-benzoid acid (step a)) in 116 ml of acetic anhydride are heated at 110° C. 12.92 g (0.131 mol) of potassium acetate are added in 2 min and heating is continued for 40 min at 130-135° C. After 10 min, the title compound starts to crystallize. The reaction vessel is cooled to room temperature, and the solid is filtered off and washed with acetic acid and water. Drying follows at 95° C. for 16 h (high vacuum). mp: 341-342° C. (dec.). ES-MS: m/e$_0$=225.

Step c) 4,6-Dichloro-3-nitro-quinoline 11 g (48.97 mmol) of 6-chloro-3-nitro-quinolin-4-ol (step b) in 80 ml of POCl$_3$ are heated under reflux for 5 h (tlc-control). The cool reaction mixture is poured slowly into 1.5 l of ice water. The title compound separates as a solid. The mixture is stirred for 15 min, the temperature not exceeding 0-5° C. The solid is filtered off, washed with water and dissolved in 200 ml ethylacetate. The organic phase is washed with a mixture of 200 ml of water and 38 ml of a 2 N sodium hydroxide solution, then again with water. After drying over MgSO$_4$, the solvent is evaporated almost to dryness; hexane is added to the residue and the title compound is isolated by filtration as a dark-grey powder. This material is used in the next step without further purification.

Step d) (6-Chloro-3-nitro-quinolin-4-yl)-phenyl-amine 0.6 g (2.46 mmol) of 4,6-dichloro-3-nitro-quinoline (step c)) and 0.247 ml (2.71 mmol) of aniline in 4 ml of acetic acid are stirred at room temperature for 4 h (tlc-control). A precipitate is formed. The reaction mixture is poured into 150 ml of water. The solid is filtered off and washed with water and hexane. The filtrate is dissolved in ca. 50 ml of diethylether, filtered from insoluble material, and the solvent is evaporated. The residue (title compound, yellow crystals) is dried at 60° C. overnight. mp: 174-175° C.; ES-MS: m/e$_0$=300.

Step e) 6-Chloro-N-4-phenyl-quinoline-3,4-diamine 530 mg (1.7 mmol) of (6-chloro-3-nitro-quinolin-4-yl)-phenyl-amine (step d)) in 50 ml methanol and 0.3 g of Raney-Ni are hydrogenated at room temperature for 30 min. The reaction solution is filtered over Hyflo® Super Cel diatomaceous earth and is evaporated to dryness. The residue is dissolved in 15 ml of acetone, and hexane is added. The title compound separates as a crystalline solid and is filtered off and dried at 60° C. overnight (high vacuum) to yield the title compound. mp: 198-199° C.; ES-MS: m/e$_0$=270.

B) Synthesis of Example 93:

8-Bromo-1-(2-chloro-phenyl)-1,3-dihydro-imidazo[4,5-c]quinolin-2-one

The title compound is obtained as described for Example 92 [see above under A)] using 6-bromo-N-(2-chloro-phenyl)-quinoline-3,4-diamine, which is obtained as described for Example 92, steps a) to e) using 2-amino-5-bromo-benzoic acid (Fluka, Buchs, Switzerland) as starting material. Title compound: Analytical HPLC: t$_{ret}$=6.18 min (Grad. 2); ES-MS: m/e$_0$=374.0, 376.0.

C) Synthesis of Example 95:

1-(2-Chloro-phenyl)-8-methyl-1,3-dihydro-imidazo[4,5-c]quinolin-2-one

The title compound os obtained as described for Example 92 using N4-(2-chloro-phenyl)-6-methyl-quinoline-3,4-diamine, which is obtained as described for Example 92, steps a=to e) using 2-amino-5-methyl-benzoic acid (Fluka, Buchs, Switzerland) as starting material. Title compound: Analytical HPLC: t$_{ret}$=5.80 min (Grad. 2); ES-MS: m/e$_0$=310.1, 312.1.

D) Synthesis of Example 104:

8-Bromo-1-(2-chloro-phenyl)-3-methyl-1,3-dihydro-imidazo[4,5-c]quinolin-2-one 300 mg (0.8 mmol) of 8-bromo-1-(2-chloro-phenyl)-1,3-dihydro-imidazo[4,5-c]quinolin-2-one [see under B)] are dissolved in 5 ml of anhydrous N,N-dimethylformamide and 35 mg (0.8 mmol) of NaH are added portionwise. The suspension is stirred for 90 min at room temperature and 113 mg (0.8 mmol) of methyl iodide dissolved in 3 ml of N,N-dimethylformamide are added. After stirring for 18 h at room temperature, the solution is cooled at 0° C. and 20 ml of water are added slowly to the stirred suspension. The suspension is extracted with ethyl acetate and the water phase is discarded. The organic phase is washed with brine, dried with Na$_2$SO$_4$ and evaporated to dryness. The crude compound is purified by flash-chromatography (dichloromethane with 2% methanol) to provide the title compound: Analytical HPLC: t$_{ret}$=7.64 min (Grad. 2); ES-MS: m/e$_0$=388.0, 390.0.

E) Synthesis of Example 113:

8-Bromo-1-(2-chloro-phenyl)-3-ethyl-1,3-dihydro-imidazo[4,5-c]quinolin-2-one The title compound is obtained as described under D) using ethyl iodide. Title compound: Analytical HPLC: t$_{ret}$=7.21 min (Grad. 2); ES-MS: m/e$_0$=402.0, 404.0.

F) Synthesis of Example 114:

8-Bromo-1-(2-chloro-phenyl)-3-isopropyl-1,3-dihydro-imidazo[4,5-c]quinolin-2-one The title compound is obtained as described under D) using isopropyl iodide. Title compound: Analytical HPLC: t$_{ret}$=7.94 min (Grad. 2); ES-MS: m/e$_0$=416.0, 418.0.

G) Synthesis of Example 108:

8-Chloro-1-(2-chloro-phenyl)-3-ethyl-1,3-dihydro-imidazo[4,5-c]quinolin-2-one The title compound is obtained as described for Example 92 using 6-chloro-N-4-(2-chlorophenyl)-N-3-ethyl-quinoline-3,4-diamine. Title compound: Analytical HPLC: t$_{ret}$=6.80 min (Grad. 2); ES-MS: m/e$_0$=358.0, 360.0.

The starting material is prepared as follows:

Step a) 6-Chloro-N-4-(2-chloro-phenyl)-N-3-ethyl-quinoline-3,4-diamine

To a stirred solution of 200 mg (0.66 mol) of 6-chloro-N-4-(2-chloro-phenyl)-quinoline-3,4-diamine (which is obtained as described in Example 23) in 3 ml of dichloromethane, 87 mg (1.98 mmol) of acetaldehyde (Fluka, Buchs, Switzerland) and 25 μl (0.44 mmol) of acetic acid are added. After stirring the solution for 5 h at room temperature, the solution is cooled at 10° C. and 146 mg (2.32 mmol) of sodium cyanoborohydride are added. The solution is stirred for 16 h at room temperature and 25 ml of dichloromethane are added. The solution is washed with 5% NaHCO$_3$ and brine, dried with Na$_2$SO$_4$ and evaporated to dryness. The crude compound is further purified by flash-chromatography (dicholomethane) to obtain the title compound: Analytical HPLC: t$_{ret}$=7.96 min (Grad. 2); ES-MS: m/e$_0$=332.1, 334.1,
H) Synthesis of Example 128:

8-chloro-1-(2-chloro-phenyl)-3-cyclopropylmethyl-1,3-dihydro-imidazo[4,5-c]quinolin-2-one The title compound is obtained as described under G) using cyclopropanecarboxaldehyde (Aldrich, Buch, Switzerland).
Analytical HPLC: t$_{ret}$=6.86 min (Grad. 2); ES-MS: m/e$_0$=384.0, 386.0.
I) synthesis of Example 133:

8-chloro-1-(2-chloro-phenyl)-3-furan-3-ylmethyl-1,3-dihydro-imidazo[4,5-c]quinolin-2-one The title compound is obtained as described under G) using 3-furaldehyde (Fluka, Buchs, Switzerland). Analytical HPLC: t$_{ret}$=6.88 min (Grad. 2); ES-MS: m/e$_0$=410.0, 412.0.
J) Synthesis of Example 100:

8-Bromo-1-(2-chloro-phenyl)-3-phenyl-1,3-dihydro-imidazo[4,5-c]quinolin-2-one 50 mg (0.13 mmol) of 8-bromo-1-(2-chloro-phenyl)-1,3-dihydro-imidazo[4,5-c]quinolin-2-one [see under B)], 48.8 mg (0.40 mmol) of phenylboronic acid (Fluka, Buchs, Switzerland), 53 mg (0.27 mmol) of cupric acetate anhydrous (Fluka, Buchs, Switzerland) and 56 µl (0.4 mmol) of triethylamine are dissolved in 1 ml of anhydrous dichloromethane and the suspension is stirred for 16 h at room temperature. After this time, additional phenylboronic acid (24 mg), cupric acetate anhydrous (27 mg) and triethylamine (28 µl) are added and the suspension is stirred at room temperature for 24 h. The suspension is evaporated to dryness and the crude compound is purified by clash chromatography (dichloromethan with 0.5% of methanol) to obtain the title compound: Analytical HPLC: t$_{ret}$=8.22 min (Grad. 2); ES-MS: m/e$_0$=449.9. 451.9.

In analogy or as described in Example 89, and starting from the appropriate starting materials and intermediates, the following compounds are synthesized:

TABLE 9

| Example | Compound name |
|---|---|
| 90 | 1-(2-Fluorophenyl)-1,3-dihydro-imidazo[4,5-c]quinolin-2-one |
| 91 | 1-(2-Fluorophenyl)-1,3-dihydro-imidazo[4,5-c]quinolin-2-one (HCl-salt) |
| 92 | 8-Chloro-1-(2-chloro-phenyl)-1,3-dihydro-imidazo[4,5-c]quinolin-2-one |
| 93 | 8-Bromo-1-(2-chloro-phenyl)-1,3-dihydro-imidazo[4,5-c]quinolin-2-one |
| 94 | 1-(2-Fluoro-phenyl)-8-methyl-1,3-dihydro-imidazo[4,5-c]quinolin-2-one (HCl salt) |
| 95 | 1-(2-Chloro-phenyl)-8-methyl-1,3-dihydro-imidazo[4,5-c]quinolin-2-one |
| 96 | 8-Chloro-1-(2-chloro-phenyl)-3-phenyl-1,3-dihydro-imidazo[4,5-c]quinolin-2-one |
| 97 | 8-Chloro-1-(2-fluoro-phenyl)-1,3-dihydro-imidazo[4,5-c]quinolin-2-one (HCl salt) |
| 98 | 8-Chloro-1-(2-chloro-phenyl)-3-(3-chloro-phenyl)-1,3-dihydro-imidazo[4,5-c]quinolin-2-one |
| 99 | 1-(2-Chloro-phenyl)-8-methyl-3-phenyl-1,3-dihydro-imidazo[4,5-c]quinolin-2-one |
| 100 | 8-Bromo-1-(2-chloro-phenyl)-3-phenyl-1,3-dihydro-imidazo[4,5-c]quinolin-2-one |
| 101 | 1-(2-Chloro-phenyl)-8-methyl-3-(3-chloro-phenyl)-1,3-dihydro-imidazo[4,5-c]quinolin-2-one |
| 102 | 8-Bromo-1-(2-chloro-phenyl)-3-(3-chloro-phenyl)-1,3-dihydro-imidazo[4,5-c]quinolin-2-one |
| 103 | 3-(3-Aminophenyl)-8-chloro-1-(2-chloro-phenyl)-1,3-dihydro-imidazo[4,5-c]quinolin-2-one |
| 104 | 8-Bromo-1-(2-chloro-phenyl)-3-methyl-1,3-dihydro-imidazo[4,5-c]quinolin-2-one |
| 105 | 8-Chloro-1-(2-chloro-phenyl)-3-(3-methoxy-phenyl)-1,3-dihydro-imidazo[4,5-c]quinolin-2-one |
| 106 | 3-(3-Amino-phenyl)-1-(2-chloro-phenyl)-8-methyl-1,3-dihydro-imidazo[4,5-c]quinolin-2-one |
| 107 | 3-(Amino-phenyl)-8-bromo-1-(2-chloro-phenyl)-1,3-dihydro-imidazo[4,5-c]quinolin-2-one |
| 108 | 8-Chloro-1-(2-chloro-phenyl)-3-ethyl-1,3-dihydro-imidazo[4,5-c]quinolin-2-one |
| 109 | 8-Bromo-1-(2-chloro-phenyl)-3-(3-methoxy-phenyl)-1,3-dihydro-imidazo[4,5-c]quinolin-2-one |
| 110 | 1-(2-Chloro-phenyl)-3-(3-methoxy-phenyl)-8-methyl-1,3-dihydro-imidazo[4,5-c]quinolin-2-one |
| 111 | 1-(2-Chloro-phenyl)-8-methyl-3-(3-trifluoromethyl-phenyl)-1,3-dihydro-imidazo[4,5-c]quinolin-2-one |
| 112 | 8-Chloro-1-(2-chloro-phenyl)-3-(3-trifluoromethyl-phenyl)-1,3-dihydro-imidazo[4,5-c]quinolin-2-one |
| 113 | 8-Bromo-1-(2-chloro-phenyl)-3-ethyl-1,3-dihydro-imidazo[4,5-c]quinolin-2-one |
| 114 | 8-Bromo-1-(2-chloro-phenyl)-3-isopropyl-1,3-dihydro-imidazo[4,5-c]quinolin-2-one |
| 115 | 8-Chloro-1-(2-chloro-phenyl)-3-(3-nitrophenyl)-1,3-dihydro-imidazo[4,5-c]quinolin-2-one |
| 116 | 8-Bromo-1-(2-chloro-phenyl)-3-(3-trifluoromethyl-phenyl)-1,3-dihydro-imidazo[4,5-c]quinolin-2-one |
| 117 | 8-Chloro-1-(2-chloro-phenyl)-3-(2-methyl-propyl)-1,3-dihydro-imidazo[4,5-c]quinolin-2-one |
| 118 | 1-Cyclohexyl-6-(n-hexyl)oxy-8-methyl-1,3-dihydro-imidazo[4,5-c]quinolin-2-one |
| 119 | 8-Chloro-1-(2-chloro-phenyl)-3-(2,2-dimethyl-propyl)-1,3-dihydro-imidazo[4,5-c]quinolin-2-one |
| 120 | 3-(3-Acetylamino-phenyl)-8-chloro-1-(2-chloro-phenyl)-1,3-dihydro-imidazo[4,5-c]quinolin-2-one |
| 121 | 3-(n-Butyl)-8-chloro-1-(2-chloro-phenyl)-1,3-dihydro-imidazo[4,5-c]quinolin-2-one |
| 122 | 8-Chloro-1-(2-chloro-phenyl)-3-(3-nitro-phenyl)-1,3-dihydro-imidazo[4,5-c]quinolin-2-one |
| 123 | 8-Chloro-1-(2-chloro-phenyl)-3-(n-(2-ethyl)-butyl)-1,3-dihydro-imidazo[4,5-c]quinolin-2-one |
| 124 | 8-Bromo-1-(2-chloro-phenyl)-3-(3-nitro-phenyl)-1,3-dihydro-imidazo[4,5-c]quinolin-2-one |
| 125 | 8-Chloro-1-(2-chloro-phenyl)-3-(3-hydroxy-2,2-dimethyl)propyl-1,3-dihydro-imidazo[4,5-c]quinolin-2-one |
| 126 | 3-(3-Acetylamino-phenyl)-1-(2-chloro-phenyl)-8-methyl-1,3-dihydro-imidazo[4,5-c]quinolin-2-one |
| 127 | 1-Cyclohexyl-6-(n-hexyl)oxy-3-isopropyl-8-methyl-1,3-dihydro-imidazo[4,5-c]quinolin-2-one |
| 128 | 8-Chloro-1-(2-chloro-phenyl)-3-(cyclopropyl-methyl)-1,3-dihydro-imidazo[4,5-c]quinolin-2-one |
| 129 | 3-(3-Acetylamino-phenyl)-8-bromo-1-(2-chloro-phenyl)-1,3-dihydro-imidazo[4,5-c]quinolin-2-one |
| 130 | 8-Chloro-1-(2-chloro-phenyl)-3-(n-heptyl)-1,3-dihydro-imidazo[4,5-c]quinolin-2-one |
| 131 | 8-Chloro-1-(2-chloro-phenyl)-3-(cyclohexyl-methyl)-1,3-dihydro-imidazo[4,5-c]quinolin-2-one |
| 132 | 8-Chloro-1-(2-chloro-phenyl)-3-(2,3-dihydroxy-propyl)-1,3-dihydro-imidazo[4,5-c]quinolin-2-one |
| 133 | 8-Chloro-1-(2-chloro-phenyl)-3-(3-furyl-methyl)-1,3-dihydro-imidazo[4,5-c]quinolin-2-one |
| 134 | 1-Cyclohexyl-6-(n-hexyl)oxy-8-methyl-3-(n-propyl)-1,3-dihydro-imidazo[4,5-c]quinolin-2-one |

Example 135

8-Bromo-1-(2-chloro-phenyl)-1H-imidazo[4,5-c]quinoline

The title compound is obtained as described in Example 1 using 6-bromo-N-4-(2-chloro-phenyl)-quinoline-3,4-diamine as starting material. 6-Bromo-N-4-(2-chloro-phenyl)quinoline-3,4-diamine is obtained as described in example 1a-1d using 2-amino-5-bromo-benzoic acid (Fluka, Buchs, Switzerland) as starting material. MS: 360.0; HPLC: $t_R$=7.06 min (Grad. 2).

Example 136

8-Chloro-1-(2-chloro-phenyl)-2-methyl-1H-imidazo[4,5-c]quinoline

The title compound is obtained as described in example 85 using 6-chloro-N-4-(2-chloro-phenyl)-quinoline-3,4-diamine (Example 83a) and malonamic acid in 4 N HCl at 120° C. mp: 177.5° C. MS: 328.1, 330.1

Example 137

1-(2-Chloro-phenyl)-8-(4-methoxy-phenyl)-1H-imidazo[4,5-c]quinoline

The title compound is obtained as described in Example 142 using 4-methoxyphenylboronic acid (Aldrich, Buchs, Switzerland). MS: 386.0; HPLC: $t_R$=7.04 min (Grad. 2).

Example 138

4-[1-(2-Fluoro-phenyl)-1H-imidazo[4,5-c]quinolin-8-yl]-phenol

The title compound is obtained as described in Example 140 using 4-hydroxybenzeneboronic acid (Lancaster, Lancashire, UK) and 8-bromo-1-(2-fluoro-phenyl)-1H-imidazo[4,5-c]quinoline, which is obtained as described in Example 19 using 6-bromo-N-4-(2-fluoro-phenyl)-quinoline-3,4-diamine as starting material. MS: 356.4; HPLC: $t_R$=6.67 min (Grad. 2).

Example 139

1,8-Diphenyl-1H-imidazo[4,5-c]quinoline

The title compound is obtained by hydrogenation of 1-(2-chloro-phenyl)-8-phenyl-1H-imidazo[4,5-c]quinoline in MeOH/DMF (1:1, v/v) and Pd/C 10%. 1-(2-Chloro-phenyl-8-phenyl-1H-imidazo[4,5-c]quinoline is obtained as described in Example 53. MS: 322.2; HPLC: $t_R$=6.86 min (Grad. 2).

Example 140

1-(2-Chloro-phenyl)-8-(3-methoxy-phenyl)-1H-imidazo[4,5-c]quinoline

To a solution of 8-bromo-1-(2-chloro-phenyl)-1H-imidazo[4,5-c]quinoline (100 mg, which is obtained as described in Example 1 starting with 2-amino-5-bromo-benzoic acid, in DMF (2 ml) is added 3-methoxyphenylboronic acid (60 mg; Aldrich, Buchs, Switzerland), PdCl$_2$(PPh$_3$) (10 mg) and 1M potassium carbonate (0.7 ml). The reaction is stirred at 100° C. for 1 h. After this time, ethyl acetate (50 ml) is added and the solution is extracted with water. After drying the organic phase with MgSO$_4$, the solvent is evaporated to dryness and the residue is purified by chromatography on silica gel (DCM/MeOH 2%) to provide the title compound (83 mg). MS: 386.0; HPLC: $t_R$=7.05 min (Grad. 2).

Example 141

8-Ethyl-1-phenyl-1H-imidazo[4,5-c]quinoline

The title compound is obtained by hydrogenation of 1-(2-chloro-phenyl)-8-ethyl-1H-imidazo[4,5-c]quinoline (Example 49) in MeOH/DMF (2:1, v/v) and Pd/C 10%. MS: 274.2; HPLC: $t_R$=5.63 min (Grad. 2).

Example 142

1-(2-Chloro-phenyl)-8-(2-methoxy-phenyl)-1H-imidazo[4,5-c]quinoline

The title compound is obtained as described in Example 140 using 2-methoxyphenyl boronic acid (Aldrich, Buchs, Switzerland). MS: 386.0; HPLC: $t_R$=6.84 min.

In the following examples 143 to 147 providing activity determinations of compounds of the preceding examples, the following letters are intended to symbolize the following IC$_{50}$ values (only examples with concrete measurement results are represented):

| Letter | IC$_{50}$ range class |
|---|---|
| A | ≦0.5 µM |
| B | more than 0.5 µM up to 1 µM |
| C | more than 1 µM up to 2 µM. |

Example 143

Inhibition of c-Met by Compounds of the Present Invention

Using the testing method described above, with the following test compounds of formula I the following IC$_{50}$ values for inhibition of c-Met are obtained:

| Compound of Example | IC$_{50}$ range class |
|---|---|
| 25 | A |
| 50 | A |
| 84 | A |
| 87 | B |
| 88 | A |
| 92 | B |
| 93 | A |
| 104 | A |
| 113 | A |
| 114 | B |
| 108 | B |
| 133 | A |
| 102 | C |

Example 144

Inhibition of CDK1 by Compounds of the Present Invention

Using the test system described above, with the following test compounds of formula I the following $IC_{50}$ values for inhibition of CDK1 in vitro are obtained:

| Compound of Example | $IC_{50}$ range class |
|---|---|
| 49 | A |
| 50 | A |
| 104 | C |
| 113 | C |
| 114 | A |
| 108 | A |
| 128 | B |

Example 145

Inhibition of Kdr by Compounds of the Present Invention

Using the test system described above, with the following test compounds of formula I the following $IC_{50}$ values for inhibition of Kdr in vitro are obtained:

| Compound of Example | $IC_{50}$ range class |
|---|---|
| 48 | C |
| 58 | A |
| 62 | A |
| 140 | A |
| 93 | B |
| 113 | C |
| 114 | A |
| 108 | A |

Example 146

Inhibition of Abl by Compounds of the Present Invention

Using the test system described above, with the following test compounds of formula I the following $IC_{50}$ values for inhibition of Abl in vitro are obtained:

| Compound of Example | $IC_{50}$ range class |
|---|---|
| 58 | A |
| 62 | A |
| 140 | A |
| 142 | A |

Example 147

Inhibition of PKB/Akt by Compounds of the Present Invention

Using the test system described above, with the following test compounds of formula I the following $IC_{50}$ values for inhibition of PKB/Akt in vitro are obtained:

| Compound of Example | $IC_{50}$ range class |
|---|---|
| 54 | C |
| 137 | C |

Example 148

Tablets 1 Comprising Compounds of the Formula I

Tablets, comprising, as active ingredient, 50 mg of any one of the compounds of formula I mentioned in the preceding Examples 1 to 142 of the following composition are prepared using routine methods:

Composition:

| | |
|---|---|
| Active Ingredient | 50 mg |
| wheat starch | 60 mg |
| lactose | 50 mg |
| colloidal silica | 5 mg |
| talcum | 9 mg |
| magnesium stearate | 1 mg |
| | 175 mg |

Manufacture: The active ingredient is combined with part of the wheat starch, the lactose and the colloidal silica and the mixture pressed through a sieve. A further part of the wheat starch is mixed with the 5-fold amount of water on a water bath to form a paste and the mixture made first is kneaded with this paste until a weakly plastic mass is formed.

The dry granules are pressed through a sieve having a mesh size of 3 mm, mixed with a pre-sieved mixture (1 mm sieve) of the remaining corn starch, magnesium stearate and talcum and compressed to form slightly biconvex tablets.

Example 149

Tablets 2 Comprising Compounds of the Formula I

Tablets, comprising, as active ingredient, 100 mg of any one of the compounds of formula I of Examples 1 to 142 are prepared with the following composition, following standard procedures:

Composition:

| | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, Stempeldurchmesser 10 mm).

Example 150

Capsules

Capsules, comprising, as active ingredient, 100 mg of any one of the compounds of formula I given in Examples 1 to 142, of the following composition are prepared according to standard procedures:

Composition:

| | |
|---|---|
| Active Ingredient | 100 mg |
| Avicel | 200 mg |
| PVPPXL | 15 mg |
| Aerosil | 2 mg |
| magnesium stearate | 1.5 mg |
| | 318.5 mg |

Manufacturing is done by mixing the components and filling them into hard gelatine capsules, size 1.

What is claimed is:

1. A compound of the formula I

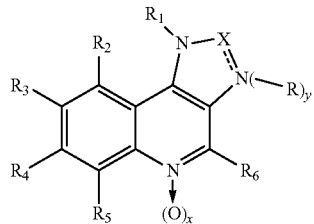

(I)

wherein each of x and y is, independently of the other, 0 or 1, $R_1$ is phenyl or phenyl-lower alkyl, each of which, in the phenyl moiety, is substituted by up to three moieties independently selected from halo-lower alkyl, especially trifluoromethyl, hydroxy, $C_6$-$C_{14}$-aryl, especially phenyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;

or is $C_3$-$C_8$-cycloalkyl, especially cyclohexyl, or hydroxy-$C_3$-$C_8$-cycloalkyl, especially hydroxy-cyclohexyl;

X is C═O or C═S with the proviso that then the dashed line bonding X to N is absent, so that X is bound to the adjacent N via a single bond and with the proviso that then y is 1 and R is hydrogen or an organic moiety that can be bound to nitrogen;

and at least one but not more than two of $R_2$, $R_3$, $R_4$, $R_5$ and $R_6$, independently of the others, is an organic moiety or an inorganic moiety, the remainder being hydrogen;

wherein the organic moiety is selected from an unsubstituted or substituted alkyl, unsubstituted or substituted alkenyl, unsubstituted or substituted alkinyl, unsubstituted or substituted aryl, unsubstituted or substituted heterocyclyl, unsubstituted or substituted cycloalkyl or unsubstituted or substituted cycloalkenyl, unsubstituted or substituted arylcarbonylamino, amino substituted by one or two moieties selected from the group consisting of lower alkyl, substituted lower alkyl moieties, aryl, cycloalkyl and mercapto-lower alkyl, alkyloxy or cyano; and wherein the inorganic moiety is selected from halogen, hydroxy, amino, or nitro;

provided that $R_3$ is hydrogen, lower alkyl, especially ethyl, halo, especially fluoro, chloro or bromo, lower alkoxy, especially methoxy, or unsubstituted or substituted $C_6$-$C_{14}$-aryl, especially phenyl, hydroxyphenyl or methoxyphenyl or a pharmaceutically acceptable salt thereof.

2. A compound according to claim 1 where in the compound of the formula I, or a pharmaceutically acceptable salt thereof, each of x and y is, independently of the other, 0 or 1, $R_1$ is phenyl or phenyl-lower alkyl, each of which, in the phenyl moiety, is substituted by up to three moieties independently selected from halogen, especially fluoro, chloro, bromo or iodo, lower alkyl, especially methyl or ethyl, halo-lower alkyl, especially trifluoromethyl, hydroxy, lower alkoxy, especially methoxy, $C_6$-$C_{14}$-aryl, especially phenyl, hydroxy-lower alkyl, especially 2-hydroxyethyl or hydroxymethyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;

or is $C_3$-$C_8$-cycloalkyl, especially cyclohexyl, or hydroxy-$C_3$-$C_8$-cycloalkyl, especially hydroxycyclohexyl;

X is C═O or C═S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethylpropyl or 2-ethyl-n-butyl; mono- or di-hydroxy-lower alkyl, especially 2,3-dihydroxy-propyl or 3-hydroxy-2,2-dimethylpropyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;

$R_2$ is hydrogen;

$R_3$ is hydrogen, lower alkyl, especially ethyl, halo, especially fluoro, chloro or bromo, lower alkoxy, especially methoxy, or unsubstituted or substituted $C_6$-$C_{14}$-aryl, especially phenyl, hydroxyphenyl or methoxyphenyl;

$R_4$ is hydrogen or halo, especially chloro;

$R_5$ is hydrogen or lower alkoxy, especially n-lower hexyloxy; and $R_6$ is hydrogen, halo, especially chloro, $C_6$-$C_{14}$-aryl, especially phenyl, $C_3$-$C_8$-cycloalkyl, especially cyclopropyl, amino, lower alkyl-amino, especially methylamino or n-butylamino, hydroxy-lower alkylamino, especially 2-hydroxyethyl-amino or C6-C14-arylcarbonylamino, especially benzoylamino;

provided that at least one but not more than two of $R_2$, $R_3$, $R_4$, $R_5$ and $R_6$ is other than hydrogen.

3. A compound of the formula I, or a pharmaceutically acceptable salt thereof, as shown in claim 1, wherein X is C═O and the other moieties are as defined in claim 1.

4. A compound of formula I, or a pharmaceutically acceptable salt thereof, as shown in claim 1 wherein each of x and y is, independently of the other, 0 or 1, $R_1$ is phenyl or phenyl-lower alkyl, each of which, in the phenyl moiety, is substituted by up to three moieties independently selected from halo-lower alkyl, especially trifluoromethyl, hydroxy, $C_6$-$C_{14}$-aryl, especially phenyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;
or is $C_3$-$C_8$-cycloalkyl, especially cyclohexyl, or hydroxy-$C_3$-$C_8$-cycloalkyl, especially hydroxycyclohexyl;
X is C═O or C═S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethyl-propyl or 2-ethyl-n-butyl; mono- or di-hydroxy-lower alkyl, especially 2,3-dihydroxy-propyl or 3-hydroxy-2,2-dimethylpropyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;
$R_2$ is hydrogen;
$R_3$ is hydrogen, lower alky, especially ethyl, halo, especially fluoro, chloro or bromo, lower alkoxy, especially methoxy, or unsubstituted or substituted C6-C14-aryl, especially phenyl, hydroxyphenyl or methoxyphenyl;
$R_4$ is hydrogen or halo, especially chloro;
$R_5$ is hydrogen or lower alkoxy, especially n-lower hexyloxy; and
$R_6$ is hydrogen, halo, especially chloro, $C_6$-$C_{14}$-aryl, especially phenyl, $C_3$-$C_8$-cycloalkyl, especially cyclopropyl, amino, lower alkyl-amino, especially methylamino or n-butylamino, hydroxy-lower alkylamino, especially 2-hydroxyethyl-amino or —$C_6$-$C_{14}$-arylcarbonylamino, especially benzoylamino;
provided that at least one but not more than two of $R_2$, $R_3$, $R_4$, $R_5$ and $R_6$ is other than hydrogen;
or a pharmaceutically acceptable salt thereof.

5. A compound of the formula I, or a pharmaceutically acceptable salt thereof, as shown in claim 1, wherein
each of x and y is, independently of the other, 0 or 1,
$R_1$ is phenyl or phenyl-lower alkyl, each of which, in the phenyl moiety, is substituted by up to three moieties independently selected from halogen, especially fluoro, chloro, bromo or iodo, lower alkyl, especially methyl or ethyl, halo-lower alkyl, especially trifluoromethyl, hydroxy, lower alkoxy, especially methoxy, $C_6$-$C_{14}$-aryl, especially phenyl, hydroxy-lower alkyl, especially 2-hydroxyethyl or hydroxymethyl, amino, amino-lower alkyl, especially aminomethyl or 2-aminoethyl, amidino, N-hydroxy-amidino, amidino-lower alkyl, such as 2-amidinoethyl, N-hydroxyamidino-lower alkyl, especially N-hydroxy-amidino-methyl or -2-ethyl, cyano-lower alkyl, especially cyanomethyl, and cyano;
or is $C_3$-$C_8$-cycloalkyl, especially cyclohexyl, or hydroxy-C3-C8-cycloalkyl, especially hydroxycyclohexyl;
X is C═O or C═S with the proviso that then the dashed line bonding X to N is absent, so that X is bound to the adjacent N via a single bond and with the proviso that then y is 1 and R is hydrogen; lower alkyl, especially methyl, ethyl, n-propyl, isopropyl, n-butyl, isobutyl, 2,2-dimethylpropyl or 2-ethyl-n-butyl; mono- or di-hydroxy-lower alkyl, especially 2,3-dihydroxy-propyl or 3-hydroxy-2,2-dimethylpropyl; $C_6$-$C_{14}$-aryl which is unsubstituted or substituted by one to three substituents selected from lower alkyl, especially methyl or ethyl, halo-lower alkyl, especially trifluoromethyl, halogen, especially chloro, amino, lower alkanoylamino, lower alkoxy, especially methoxy and nitro; $C_3$-$C_8$cycloalkyl, especially cyclopropylmethyl or cyclohexylmethyl; or furanyl-lower alkyl, especially 3-furanyl-methyl;
$R_2$ is hydrogen;
$R_3$ is hydrogen, lower alkyl, especially ethyl, halo, especially fluoro, chloro or bromo, lower alkoxy, especially methoxy, or unsubstituted or substituted $C_6$-$C_{14}$-aryl, especially phenyl, hydroxyphenyl or methoxyphenyl;
$R_4$ is hydrogen or halo, especially chloro;
$R_5$ is hydrogen or lower alkoxy, especially n-lower hexyloxy; and
$R_6$ is hydrogen, halo, especially chloro, $C_6$-$C_{14}$-aryl, especially phenyl, $C_3$-$C_8$-cycloalkyl, especially cyclopropyl, amino, lower alkyl-amino, especially methylamino or n-butylamino, hydroxy-lower alkylamino, especially 2-hydroxyethyl-amino or $C_6$-$C_{14}$-arylcarbonylamino, especially benzoylamino,
provided that at least one but not more than two of $R_2$, $R_3$, $R_4$, $R_5$ and $R_6$ is other than hydrogen.

6. A compound of the formula I as shown in claim 1, selected from the group consisting of: 1-(3-trifluoromethyl-phenyl)-1H-imidazo[4,5-c]quinoline, 4-imidazo[4,5-c]quinolin-1-yl-phenol, 1-(3,4-dimethoxy-phenyl)-1H-imidazo[4,5-c]quinoline, 1-(4-iodo-phenyl)-1H-imidazo[4,5-c]quinoline, 1-biphenyl-4-yl-1H-imidazo[4,5-c]quinoline, 2-(4-imidazo[4,5-c]quinolin-1-yl-phenyl)-ethanol, (4-imidazo[4,5-c]quinolin-1-yl-phenyl)-acetonitrile, 2-imidazo[4,5-c]quinolin-1-yl-ethanol, 4-imidazo[4,5-c]quinolin-1-yl-cyclohexanol (cis-compound or cis/trans mixture), 4-imidazo[4,5-c]quinolin-1-yl-phenylamine, 2-(4-imidazo[4,5-c]quinolin-1-yl-phenyl)-ethylamine, 7-chloro-1-(4-fluoro-phenyl)-1H-imidazo[4,5-c]quinoline, 7-chloro-1-(3-trifluoromethyl-phenyl)-1H-imidazo[4,5-c]quinoline, 4-(7-chloro-imidazo[4,5-c]quinolin-1-yl)-phenol, 7-chloro-1-(3,4-dimethoxy-phenyl)-1H-imidazo[4,5-c]quinoline, 8-fluoro-1-(2-fluoro-phenyl)-1H-imidazo[4,5-c]quinoline, 1-(2-chloro-phenyl)-8-fluoro-1H-imidazo[4,5-c]quinoline, 8-fluoro-1-(2-iodo-phenyl)-1H-imidazo[4,5-c]quinoline, [2-(8-fluoro-imidazo[4,5-c]quinolin-1-yl)-phenyl]-acetonitrile, 8-chloro-1-phenyl-1H-imidazo[4,5-c]quinoline, 8-chloro-1-o-tolyl-1H-imidazo[4,5-c]quinoline, 8-chloro-1-(2-chloro-phenyl)-1H-imidazo[4,5-c]quinoline, 1-(2-bromo-phenyl)-8-chloro-1H-imidazo[4,5-c]quinoline, 8-chloro-1-(2-iodo-phenyl)-1H-imidazo[4,5-c]quinoline, 2-(8-chloro-imidazo[4,5-c]quinolin-1-yl)-benzonitrile, 8-chloro-1-(2-methoxy-phenyl)-1H-imidazo[4,5-c]quinoline, 8-chloro-1-(2-ethyl-phenyl)-1H-imidazo[4,5-c]quinoline, [2-(8-chloro-imidazo[4,5-c]quinolin-1-yl)-phenyl]-acetonitrile, [3-(8-chloro-imidazo[4,5-c]quinolin-1-yl)-2-methyl-phenyl]-methanol, 8-chloro-1-((S)-1-phenyl-ethyl)-1H-imidazo[4,5-c]quinoline, 8-chloro-1-((R)-1-phenyl-ethyl)-1H-imidazo[4,5-c]quinoline, 3-(8-chloro-imidazo[4,5-c]quinolin-1-yl)-benzonitrile, 3-(8-chloro-imidazo[4,5-c]quinolin-1-yl)-phenylamine, 2-[4-(8-chloro-imidazo[4,5-c]quinolin-1-yl)-phenyl]-ethanol, [4-(8-chloro-imidazo[4,5-c]quinolin-1-yl)-phenyl]-methanol, [4-(8-chloro-imidazo[4,5-c]quinolin-1-yl)-phenyl]-acetonitrile, [3-(8-chloro-imidazo[4,5-c]quinolin-1-yl)-phenyl]-methanol, 8-chloro-1-(2-fluoro-phenyl)-1H-imidazo[4,5-c]quinoline, 3-(8-chloro-imidazo[4,5-c]quinolin-1-yl)-benzylamine, 2-[4-(8-chloro-imidazo[4,5-c]quinolin-1-yl)-phenyl]-ethylamine, 1-(2-chloro-phenyl)-8-methoxy-1H-imidazo[4,5-c]quinoline, 1-(2-fluoro-phenyl)-8-methoxy-1H-imidazo[4,5-c]quinoline, 8-methoxy-1-o-tolyl-1H-imidazo[4,5-c]quinoline, 3-(8-methoxy-imidazo[4,5-c]quinolin-1-yl)-phenylamine, 8-methoxy-1-phenyl-1H-imidazo[4,5-c]quinoline, 1-(2-chloro-phenyl)-8-ethyl-1H-imidazo[4,5-c]quinoline, 8-ethyl-1-(2-fluoro-phenyl)-1H-imidazo[4,5-c]quinoline, 8-ethyl-1-o-tolyl-1H-imidazo[4,5-c]quinoline, 3-(8-ethyl-imidazo[4,5-c]quinolin-1-yl)-phenylamine, 1-(2-bromo-phenyl)-8-phenyl-1H-imidazo[4,5-c]quinoline, 1-(2-fluoro-phenyl)-8-phenyl-1H-imidazo[4,5-c]quinoline, 1-(2-methoxy-phenyl)-8-phenyl-1H-imidazo[4,5-c]quinoline, 8-phenyl-1-(3-trifluoromethyl-phenyl)-1H-imidazo[4,5-c]quinoline, 8-phenyl-1-o-tolyl-1H-imidazo[4,5-c]quinoline, 3-(8-phenyl-imidazo[4,5-c]quinolin-1-yl)-phenylamine, 1-(2-ethyl-phenyl)-8-phenyl-1H-imidazo[4,5-c]quinoline, 1,8-diphenyl-1H-imidazo[4,5-c]quinoline, 1-(2-chloro-4-methyl-phenyl)-8-phenyl-1H-imidazo[4,5-c]quinoline, [3-(8-phenyl-imidazo[4,5-c]quinolin-1-yl)-phenyl]-methanol, 2-(8-phenyl-imidazo[4,5-c]quinolin-1-yl)-benzonitrile, [2-(8-phenyl-imidazo[4,5-c]quinolin-1-yl)-phenyl]-acetonitrile, 2-(8-phenyl-imidazo[4,5-c]quinolin-1-yl)-benzylamine, 2-[2-(8-phenyl-imidazo[4,5-c]quinolin-1-yl)-phenyl]-ethylamine, N-hydroxy-2-(8-phenyl-imidazo[4,5-c]quinolin-1-yl)-benzamidine, N-hydroxy-2-[2-(8-phenyl-imidazo[4,5-c]quinolin-1-yl)-phenyl]-acetamidine, 2-(8-phenyl-imidazo[4,5-c]quinolin-1-yl)-benzamidine, 2-[2-(8-phenyl-imidazo[4,5-c]quinolin-1-yl)-phenyl]-acetamidine, 8-chloro-1-(2-chloro-phenyl)-1H-imidazo[4,5-c]quinoline 5-oxide, N-[8-chloro-1-(2-chloro-phenyl)-1H-imidazo[4,5-c]quinolin-4-yl]-benzamide, 8-chloro-1-(2-chloro-phenyl)-1H-imidazo[4,5-c]quinolin-4-ylamine, 8-chloro-1-(2-chloro-phenyl)-1H-imidazo[4,5-c]quinoline-4-carbonitrile, 4,8-dichloro-1-(2-chloro-phenyl)-1H-imidazo[4,5-c]quinoline, [8-chloro-1-(2-chloro-phenyl)-1H-imidazo[4,5-c]quinolin-4-yl]-methyl-amine, butyl-[8-chloro-1-(2-chloro-phenyl)-1H-imidazo[4,5-c]quinolin-4-yl]-amine, 2-[8-chloro-1-(2-chloro-phenyl)-1H-imidazo[4,5-c]quinolin-4-ylamino]-ethanol, [8-chloro-1-(2-chloro-phenyl)-1H-imidazo[4,5-c]quinolin-4-yl]-phenyl-amine, [8-chloro-1-(2-chloro-phenyl)-1H-imidazo[4,5-c]quinolin-4-yl]-cyclopropyl-amine, 2-[8-chloro-1-(2-chloro-phenyl)-1H-imidazo[4,5-c]quinolin-4-ylamino]-ethanethiol, 2-bromo-8-chloro-1-(2-chloro-phenyl)-1H-imidazo[4,5-c]quinoline, 8-chloro-1-(2-chloro-phenyl)-1H-imidazo[4,5-c]quinoline-2-carboxylic acid amide, 8-chloro-1-(2-chlorophenyl)-1H-imidazo[4,5-c]quinoline-2-carbonitrile, [8-chloro-1-(2-chloro-phenyl)-1H-imidazo[4,5-c]quinolin-2-yl]-acetonitrile, 8-chloro-1-(2-chloro-phenyl)-N-hydroxy-1H-imidazo[4,5-c]quinoline-2-carboxamidine, 2-[8-chloro-1-(2-chloro-phenyl)-N H-imidazo[4,5-c]quinolin-2-yl]-N-hydroxy-acetamidine, 2-[8-chloro-1-(2-chloro-phenyl)-1H-imidazo[4,5-c]quinolin-2-yl]-acetamidine, 8-bromo-1-(2-chlorophenyl)-1H-imidazo[4,5-c]quinoline, 8-chloro-1-(2-chlorophenyl)-2-methyl-1H-imidazo[4,5-c]quinoline, 1,8-diphenyl1H-imidazo[4,5-c]quinoline, 1-(2-chlorophenyl)-8-(3-methoxy-phenyl)-1H-imidazo[4,5-c]quinoline, 8-ethyl-1-phenyl-1H-imidazo[4,5-c]quinoline, 1-(2-chlorophenyl)-8-(2-methoxy-phenyl)-1H-imidazo[4,5-c]quinoline, 1-(2-chlorophenyl)-8-(4-methoxy-phenyl)-1H-imidazo[4,5-c]quinoline, and 4-[1-(2-fluorophenyl)-1H-imidazo[4,5-c]quinolin-8-yl]-phenol, or a (especially pharmaceutically acceptable) salt thereof.

7. A compound according to claim 1 of the formula I, selected from the group consisting of: 1-(2-fluorophenyl)-1,3-dihydro-imidazo[4,5-c]quinolin-2-one, 1-(2-fluorophenyl)-1,3-dihydro-imidazo[4,5-c]quinolin-2-one, 8-chloro-1-(2-chloro-phenyl)-1,3-dihydro-imidazo[4,5-c]quinolin-2-one, 8-bromo-1-(2-chloro-phenyl)-1,3-dihydro-imidazo[4,5-c]quinolin-2-one, 1-(2-fluoro-phenyl)-8-methyl-1,3-dihydro-imidazo[4,5-c]quinolin-2-one, 1-(2-chloro-phenyl)-8-methyl-1,3-dihydro-imidazo[4,5-c]quinolin-2-one, 8-chloro-1-(2-chloro-phenyl)-3-phenyl-1,3-dihydro-imidazo[4,5-c]quinolin-2-one, 8-chloro-1-(2-fluoro-phenyl)-1,3-dihydro-imidazo[4,5-c]quinolin-2-one, 8-chloro-1-(2-chloro-phenyl)-3-(3-chloro-phenyl)-1,3-dihydro-imidazo[4,5-c]quinolin-2-one, 1-(2-chloro-phenyl)-8-methyl-3-phenyl-1,3-dihydro-imidazo[4,5-c]quinolin-2-one, 8-bromo-1-(2-chloro-phenyl)-3-phenyl-1,3-dihydro-imidazo[4,5-c]quinolin-2-one, 1-(2-chloro-phenyl)-8-methyl-3-(3-chloro-phenyl)-1,3-dihydro-imidazo[4,5-c]quinolin-2-one, 8-bromo-1-(2-chloro-phenyl)-3-(3-chloro-phenyl)-1,3-dihydro-imidazo[4,5-c]quinolin-2-one, 3-(3-aminophenyl)-8-chloro-1-(2-chloro-phenyl)-1,3-dihydro-imidazo[4,5-c]quinolin-2-one, 8-bromo-1-(2-chloro-phenyl)-3-methyl-1,3-dihydro-imidazo[4,5-c]quinolin-2-one, 8-chloro-1-(2-chloro-phenyl)-3-(3-methoxy-phenyl)-1,3-dihydro-imidazo[4,5-c]quinolin-2-one, 3-(3-amino-phenyl)-1-(2-chloro-phenyl)-8-methyl-1,3-dihydro-imidazo[4,5-c]quinolin-2-one, 3-(amino-phenyl)-8-bromo-1-(2-chloro-phenyl)-1,3-dihydro-imidazo[4,5-c]quinolin-2-one, 8-chloro-1-(2-chloro-phenyl)-3-ethyl-1,3-dihydro-imidazo[4,5-c]quinolin-2-one, 8-bromo-1-(2-chloro-phenyl)-3-(3-methoxy-phenyl)-1,3-dihydro-imidazo[4,5-c]quinolin-2-one, 1-(2-chloro-phenyl)-3-(3-methoxy-phenyl)-8-methyl-1,3-dihydro-imidazo[4,5-c]quinolin-2-one, 1-(2-chloro-phenyl)-8-methyl-3-(3-trifluoromethyl-phenyl)-1,3-dihydro-imidazo[4,5-c]quinolin-2-one, 8-chloro-1-(2-chloro-phenyl)-3-(3-trifluoromethyl-phenyl)-1,3-dihydro-imidazo[4,5-c]quinolin-2-one, 8-bromo-1-(2-chloro-phenyl)-3-ethyl-1,3-dihydro-imidazo[4,5-c]quinolin-2-one, 8-bromo-1-(2-chloro-phenyl)-3-isopropyl-1,3-dihydro-imidazo[4,5-c]quinolin-2-one, 8-chloro-1-(2-chloro-phenyl)-3-(3-nitrophenyl)-1,3-dihydro-imidazo[4,5-c]quinolin-2-one, 8-bromo-1-(2-chloro-phenyl)-3-(3-trifluoromethyl-phenyl)-1,3-dihydro-imidazo[4,5-c]quinolin-2-one, 8-chloro-1-(2-chloro-phenyl)-3-(2-methyl-propyl)-1,3-dihydro-imidazo[4,5-c]quinolin-2-one, 1-cyclohexyl-6-(n-hexyl)oxy-8-methyl-1,3-dihydro-imidazo[4,5-c]quinolin-2-one, 8-chloro-1-(2-chloro-phenyl)-3-(2,2-dimethyl-propyl)-1,3-dihydro-imidazo[4,5-c]quinolin-2-one, 3-(3-acetylamino-phenyl)-8-chloro-1-(2-chloro-phenyl)-1,3-dihydro-imidazo[4,5-c]quinolin-2-one, 3-(n-butyl)-8-chloro-1-(2-chloro-phenyl)-1,3-dihydro-imidazo[4,5-c]quinolin-2-one, 8-chloro-1-(2-chloro-phenyl)-3-(3-nitro-phenyl)-1,3-dihydro-imidazo[4,5-c]quinolin-2-one, 8-chloro-1-(2-chloro-phenyl)-3-(n-(2-ethyl)-butyl)-1,3-dihydro-imidazo[4,5-c]quinolin-2-one, 8-bromo-1-(2-chloro-phenyl)-3-(3-nitro-phenyl)-1,3-dihydro-imidazo[4,5-c]quinolin-2-one, 8-chloro-1-(2-chloro-phenyl)-3-(3-hydroxy-2,2-dimethyl)propyl-1,3-dihydro-imidazo[4,5-c]quinolin-2-one, 3-(3-acetylamino-phenyl)-1-(2-chloro-phenyl)-8-methyl-1,3-dihydro-imidazo[4,5-c]quinolin-2-one, 1-cyclohexyl-6-(n-hexyl)oxy-3-isopropyl-8-methyl-1,3-dihydro-imidazo[4,5-c]quinolin-2-one, 8-chloro-1-(2-chloro-phenyl)-3-(cyclopropyl-methyl)-1,3-dihydro-imidazo[4,5-c]quinolin-2-one, 3-(3-acetylamino-phenyl)-8-bromo-1-(2-chloro-phenyl)-1,3-dihydro-imidazo[4,5-c]quinolin-2-one, 8-chloro-1-(2-chloro-phenyl)-3-(n-heptyl)-1,3-dihydro-imidazo[4,5-c]quinolin-2-one, 8-chloro-1-(2-chloro-phenyl)-3-(cyclohexyl-methyl)-1,3-dihydro-imidazo[4,5-c]quinolin-2-one, 8-chloro-1-(2-chloro-phenyl)-3-(2,3-dihydroxy-propyl)-1,3-dihydro-imidazo[4,5-c]quinolin-2-one, 8-chloro-1-(2-chloro-phenyl)-3-(3-furyl-methyl)-1,3-dihydro-imidazo[4,5-c]quinolin-2-one, and 1-cyclohexyl-6-(n-hexyl)oxy-8-methyl-3-(n-propyl)-1,3-dihydro-imidazo[4,5-c]quinolin-2-one, or a (especially pharmaceutically acceptable) salt thereof.

8. A pharmaceutical preparation comprising a compound of the formula I according to claim 1 or a pharmaceutically acceptable salt thereof, and a pharmaceutically acceptable carrier material.

9. A process for the preparation of a compound of the formula I according to claim 4, or a pharmaceutically acceptable salt thereof, characterized in that a compound of the formula II:

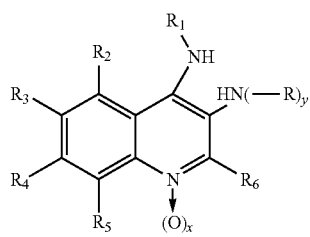
(II)

wherein x, y, R and $R_1$ to $R_6$ are as defined in claim 4, respectively, a) for the manufacture of a compound of the formula I according to claim 4 wherein X is C=O, is reacted with an active derivative of a compound of the formula III A-X-A (III) wherein X is C=O and wherein each A, independently of the other, is a carbonyl-activating group; b) for the manufacture of a compound of the formula I according to claim 4 wherein X is C=S, is reacted with CS2 or Cl—C(=S)—Cl; or c) for the manufacture of a compound of the formula I according to claim 4 wherein X is (CR$_7$) wherein R$_7$ is as defined in claim 4, is reacted with an activated derivative of a compound of the formula IV $R_7$—COOH          (IV)

wherein $R_7$ is as defined in claim 4;

wherein functional groups which are present in the starting compounds in processes a) to c) and are not intended to take part in the reaction, are present in protected form if necessary, and protecting groups that are present are cleaved, wherein said starting compounds may also exist in the form of salts provided that a salt-forming group is present and a reaction in salt form is possible;

and, if desired, an obtainable compound of formula I is transformed into a different compound of formula I, a salt of an obtainable compound of formula I is transformed into the free compound or a different salt, or an obtainable free compound of formula I is transformed into a salt.

\* \* \* \* \*